United States Patent
Iwakiri et al.

(10) Patent No.: US 11,206,366 B2
(45) Date of Patent: *Dec. 21, 2021

(54) RADIOGRAPHIC IMAGE DETECTION DEVICE AND METHOD FOR OPERATING THE SAME

(71) Applicant: FUJIFILM Corporation, Tokyo (JP)

(72) Inventors: Naoto Iwakiri, Kanagawa (JP); Kouichi Kitano, Kanagawa (JP); Syo Shimizukawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 146 days.

This patent is subject to a terminal disclaimer.

(21) Appl. No.: 16/726,958

(22) Filed: Dec. 26, 2019

(65) Prior Publication Data

US 2020/0145591 A1  May 7, 2020

Related U.S. Application Data

(63) Continuation of application No. PCT/JP2018/024251, filed on Jun. 26, 2018.

(30) Foreign Application Priority Data

Jun. 28, 2017 (JP) .............................. JP2017-126221
Feb. 20, 2018 (JP) .............................. JP2018-028297

(51) Int. Cl.
*A61B 6/00* (2006.01)
*G01T 1/24* (2006.01)
(Continued)

(52) U.S. Cl.
CPC ............. *H04N 5/32* (2013.01); *A61B 6/4233* (2013.01); *G01T 1/247* (2013.01); *G01T 7/00* (2013.01)

(58) Field of Classification Search
CPC ........ H04N 5/32; H04N 5/378; A61B 6/4233; G01T 1/247; G01T 7/00
See application file for complete search history.

(56) References Cited

U.S. PATENT DOCUMENTS 8,933,413 B2  1/2015 Kitano et al.
2013/0083897 A1  4/2013 Ohta et al.
(Continued)

FOREIGN PATENT DOCUMENTS

JP  2008172609  7/2008
JP  2012152235  8/2012
(Continued)

OTHER PUBLICATIONS

"International Search Report (Form PCT/ISA/210)"of PCT/JP2018/024251, dated Aug. 21, 2018, with English translation thereof, pp. 1-4.

(Continued)

*Primary Examiner* — Christine S. Kim
(74) *Attorney, Agent, or Firm* — JCIPRNET

(57) ABSTRACT

In a case where power P_C supplied to CA during the image reading operation is normal power PN_C, in an AED operation of detecting irradiation start of X-rays, a control unit of an electronic cassette causes at least one of non-detection CAs other than a detection CA that is the charge amplifier connected to a detection channel of a detection pixel for irradiation start detection, among the plurality of CAs connected to a MUX to be in a power saving state in which the supply power P_C is lower than the normal power PN_C during the image reading operation.

19 Claims, 62 Drawing Sheets

(51) Int. Cl.
*G01T 7/00* (2006.01)
*H04N 5/32* (2006.01)

(56) References Cited

U.S. PATENT DOCUMENTS

| | | |
|---|---|---|
| 2013/0140467 A1 | 6/2013 | Kitano et al. |
| 2014/0021365 A1 | 1/2014 | Oda |
| 2014/0347536 A1* | 11/2014 | Senda .................. H04N 5/3741 348/308 |
| 2015/0085980 A1 | 3/2015 | Kitano et al. |
| 2015/0338531 A1* | 11/2015 | Niekawa .............. H04N 5/3698 250/370.08 |
| 2018/0206805 A1* | 7/2018 | Onouchi .................. A61B 6/54 |
| 2018/0352639 A1* | 12/2018 | Carreau .................. H05G 1/10 |
| 2019/0391629 A1* | 12/2019 | Yokoyama ................ G01T 1/17 |

FOREIGN PATENT DOCUMENTS

| | | | |
|---|---|---|---|
| JP | 2013076679 | | 4/2013 |
| JP | 2014020880 | | 2/2014 |
| JP | 2016027889 | | 2/2016 |
| JP | 2016027889 A | * | 2/2016 |
| WO | 2012008229 | | 1/2012 |

OTHER PUBLICATIONS

"Written Opinion of the International Searching Authority (Form PCT/ISA/237)" of PCT/JP2018/024251, dated Aug. 21, 2018, with English translation thereof, pp. 1-15.

\* cited by examiner

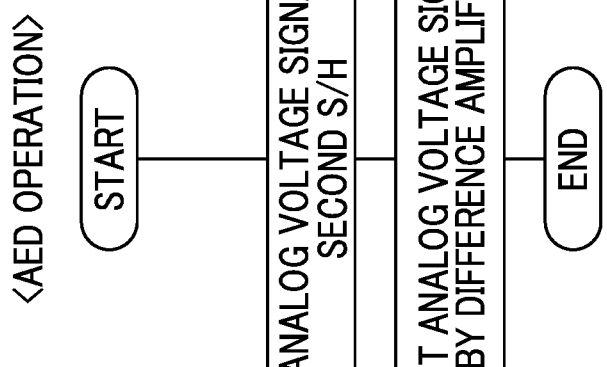

FIG. 33B

<AED OPERATION>

START → HOLD ANALOG VOLTAGE SIGNAL V(C) IN SECOND S/H (ST310) → OUTPUT ANALOG VOLTAGE SIGNAL V(C) BY DIFFERENCE AMPLIFIER (ST330) → END

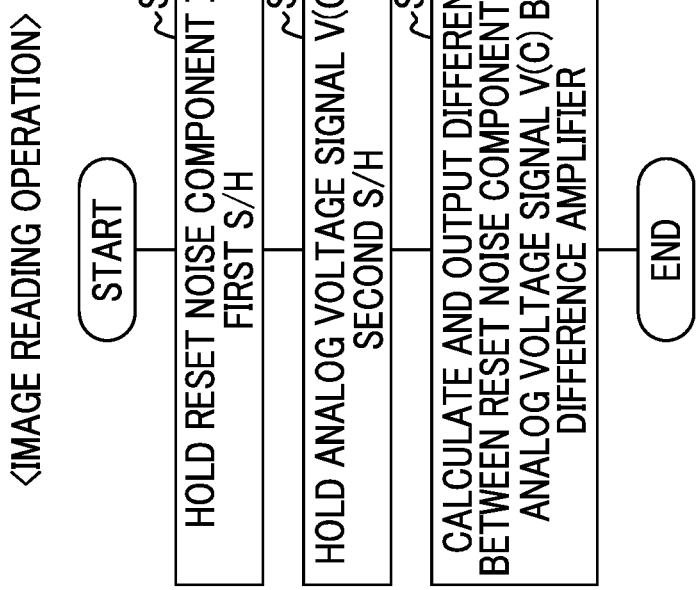

FIG. 33A

<IMAGE READING OPERATION>

START → HOLD RESET NOISE COMPONENT IN FIRST S/H (ST300) → HOLD ANALOG VOLTAGE SIGNAL V(C) IN SECOND S/H (ST310) → CALCULATE AND OUTPUT DIFFERENCE BETWEEN RESET NOISE COMPONENT AND ANALOG VOLTAGE SIGNAL V(C) BY DIFFERENCE AMPLIFIER (ST320) → END

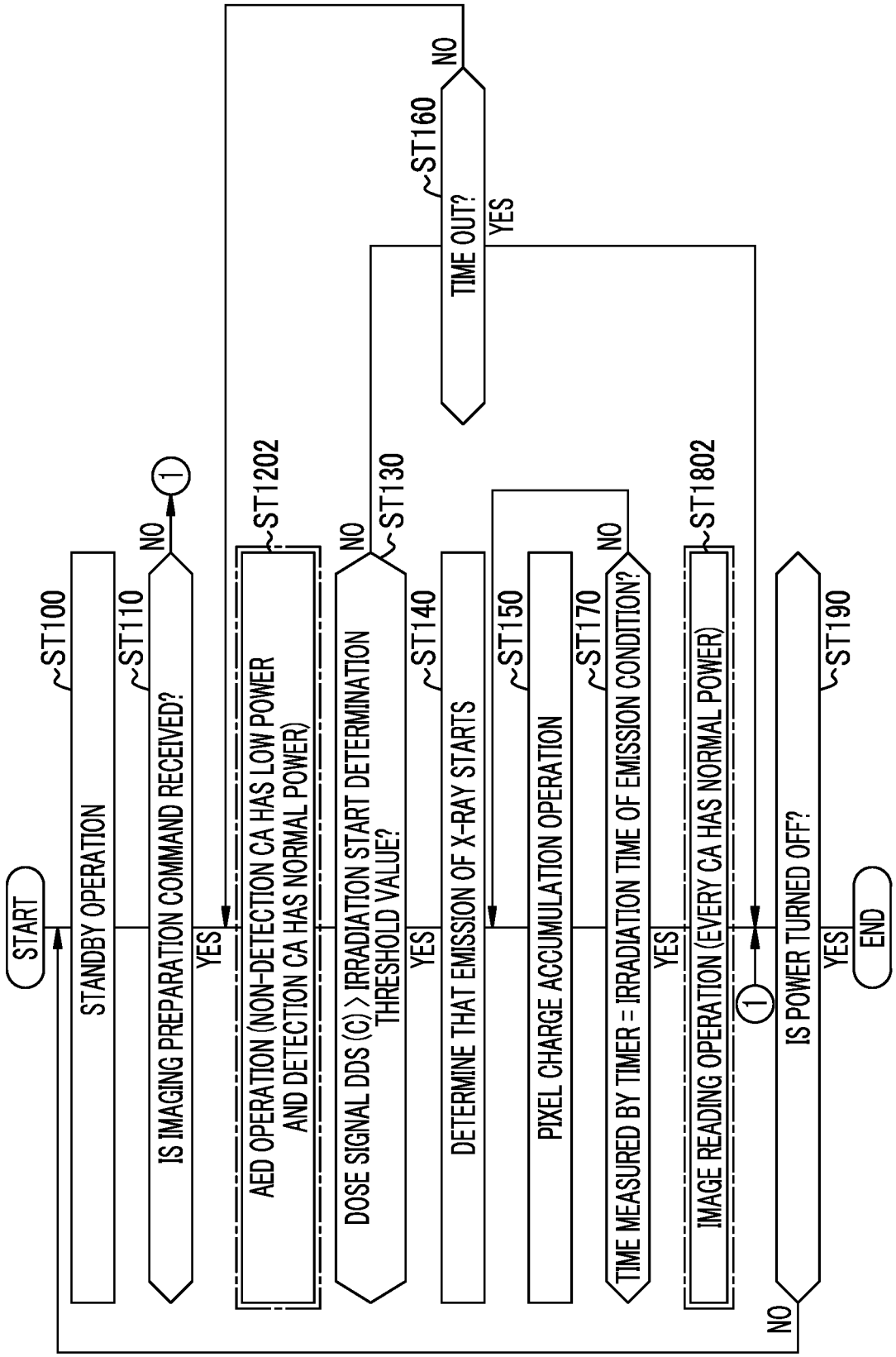

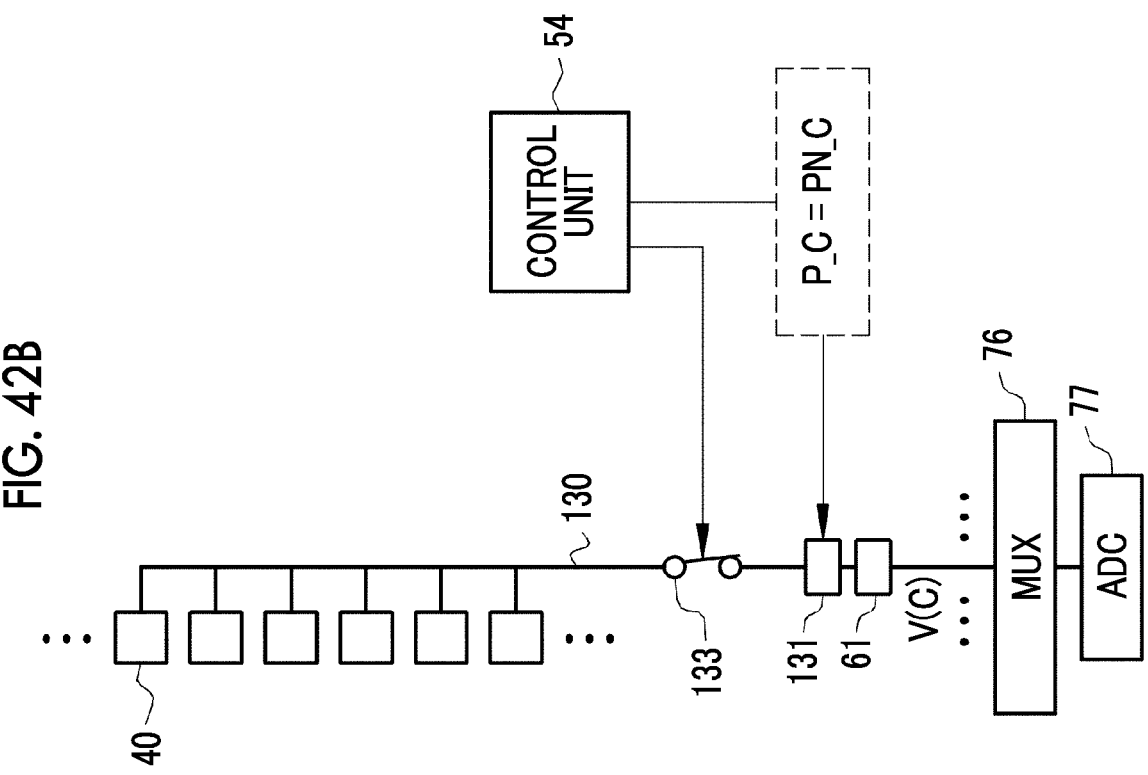
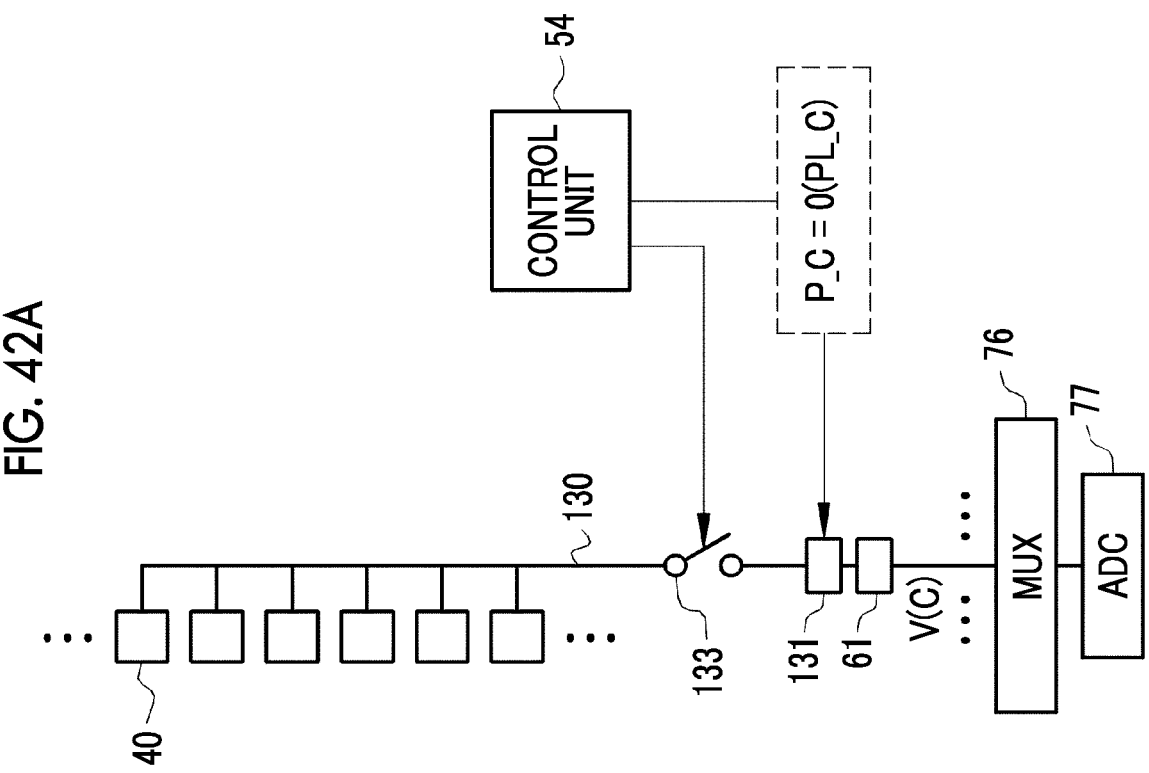

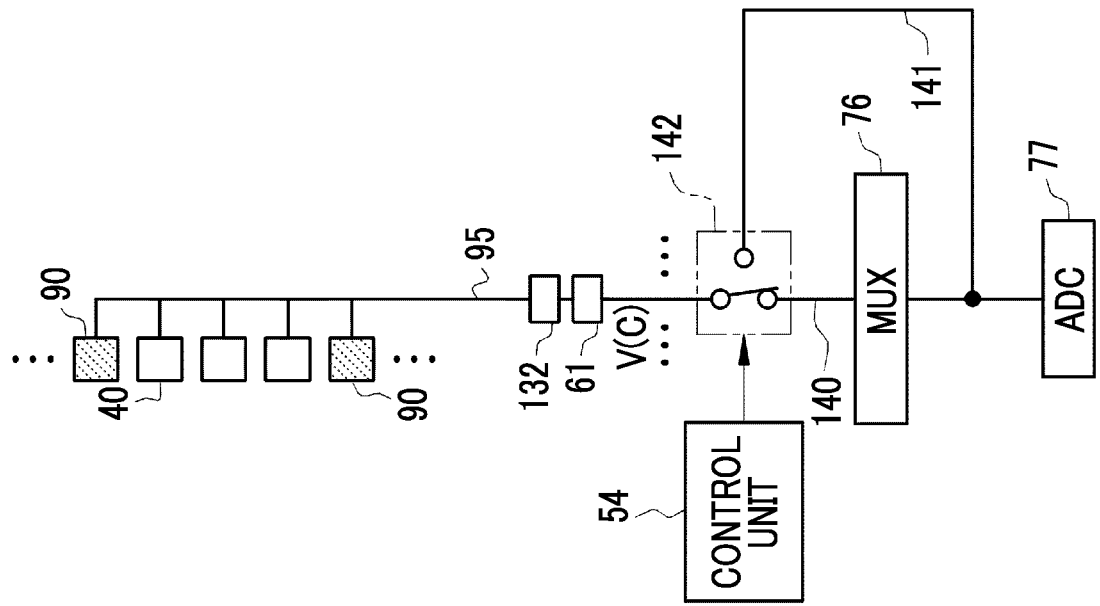
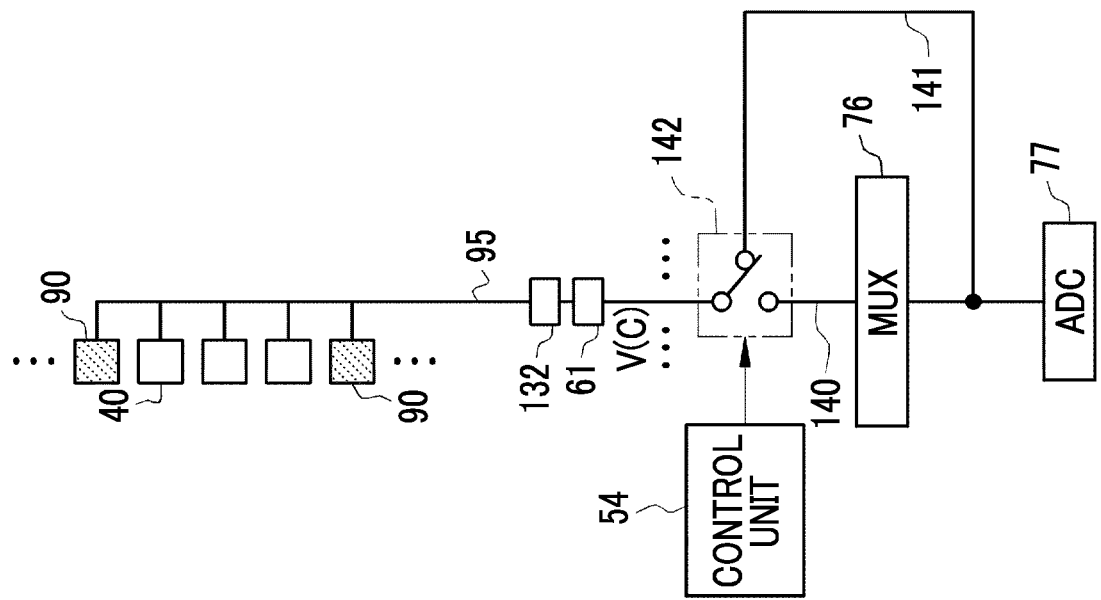

RADIOGRAPHIC IMAGE DETECTION DEVICE AND METHOD FOR OPERATING THE SAME

CROSS-REFERENCE TO RELATED APPLICATIONS

This application is a Continuation of PCT International Application No. PCT/JP2018/024251 filed on 26 Jun. 2018, which claims priority under 35 U.S.C § 119(a) to Japanese Patent Applications No. 2017-126221 filed on 28 Jun. 2017 and No. 2018-028297 filed on 20 Feb. 2018. The above application is hereby expressly incorporated by reference, in its entirety, into the present application.

BACKGROUND OF THE INVENTION

1. Field of the Invention

The present invention relates to a radiographic image detection device and a method for operating the same.

2. Description of the Related Art

In the medical field, diagnosis based on a radiographic image detected by a radiographic image detection device is actively performed. The radiographic image detection device includes a sensor panel and a circuit unit. In the sensor panel, a plurality of pixels that are sensitive to radiation which has been emitted from a radiation generation apparatus and transmitted through a subject (a patient) and accumulate charge are two-dimensionally arranged. The radiographic image detection device having the sensor panel is also called a flat panel detector (FPD). The circuit unit is provided with a signal processing circuit that converts charge accumulated in the pixels of the sensor panel into a digital signal and outputs the digital signal as a radiographic image.

The radiographic image detection devices are divided into a stationary type which is fixed to an imaging table installed in an imaging room and a portable type in which, for example, a sensor panel is accommodated in a portable housing. The portable radiographic image detection device is called an electronic cassette. The electronic cassettes are divided into a wired type that is supplied with power from a commercial power source through a cable and a wireless type that is supplied with power from a battery provided in a housing.

A switching element for selecting a pixel from which charge is read, such as a thin film transistor (TFT), is connected to each pixel. In the sensor panel, gate lines for driving the TFTs in units of rows of pixels and signal lines for reading charge from each pixel to a signal processing circuit are provided so as to intersect each other. That is, the gate lines extend in the row direction of the pixels and are arranged at predetermined pitches in the column direction of the pixels. In contrast, the signal lines extend in the column direction of the pixels and are arranged at predetermined pitches in the row direction of the pixels.

The signal processing circuit includes, for example, a charge amplifier (hereinafter, referred to as a CA), a multiplexer (hereinafter, referred to as a MUX), and an analog-to-digital (AD) converter (hereinafter, referred to as an ADC). The CA is provided for each signal line and is connected to one end of the signal line. The CA outputs an analog voltage signal corresponding to charge flowing from the pixel through the signal line. A plurality of CAs are connected to input terminals of the MUX and one ADC is connected to an output terminal. The MUX sequentially selects the analog voltage signals from the plurality of CAs connected to the input terminals and outputs the selected analog voltage signal to the ADC. The ADC performs an AD conversion process of converting the analog voltage signal from the MUX into the digital signal corresponding to the voltage value thereof.

In a case in which radiation is emitted, charge corresponding to the dose of the incident radiation is accumulated in each pixel. Since the radiation transmitted through the subject is attenuated according to the transmittance of the subject, the charge indicating the image information of the subject is accumulated in each pixel. The signal processing circuit reads the charge indicating the image information of the subject from the sensor panel, converts the charge into the digital signal, and outputs the digital signal as the radiographic image corresponding to one screen for diagnosis.

WO2012/008229A (corresponding to US2013/0140467A1) discloses a radiographic image detection device in which a sensor panel has 2880 rows of pixels and 2304 columns of pixels and a signal processing circuit has nine MUXs and nine ADCs. In WO2012/008229A, when a radiographic image corresponding to one screen is read from the sensor panel, the signal processing circuit performs the following image reading operation. That is, whenever gate pulses are sequentially applied to the gate lines corresponding to 2880 rows to sequentially turn on the rows of TFTs one by one, the charge of each of the pixels in one row in which the TFT has been turned on flows simultaneously to the signal line corresponding to each column. Then, the charge of each of the pixels in one row is read to each CA connected to each of the signal lines corresponding to 2304 columns and is then accumulated therein. Since the numbers of MUXs and ADCs are nine respectively, the number of columns of pixels that one block formed by one MUX and one ADC is in charge of is 256 (=2304/9). Nine blocks operate in parallel at the same timing. Each MUX sequentially selects the analog voltage signals from 256 CAs connected to the MUX and outputs the selected analog voltage signal to each ADC. Each ADC sequentially converts the analog voltage signal from each MUX into a digital signal and outputs the digital signal. The output of a digital signal corresponding to one row corresponds to the reading of an image corresponding to one row. In a case in which the reading of an image corresponding to one row ends, the same operation is repeated to read the next image. The image reading operation corresponding to one row is repeated 2880 times corresponding to 2880 rows and the radiographic image corresponding to one screen is output.

The radiographic image detection device disclosed in WO2012/008229A has an auto exposure detection (hereinafter, referred to as AED) function of detecting the start of the emission of radiation using the sensor panel. Specifically, the radiographic image detection device repeatedly performs the operation of reading the charge of the pixel as the digital signal from before start of the emission of radiation, similarly to the image reading operation. Hereafter, a series of operations which repeatedly performs the operation of converting the charge of the pixel into the digital signal and reading the digital signal and determines whether the emission of radiation has started on the basis of the digital signal from before start of the emission of radiation in order to detect the start of the emission of radiation is referred to as an AED operation in order to distinguish the operation from the image reading operation.

In a case in which the emission of radiation has started, the amount of charge generated in the pixel increases as compared to before the start of the emission of radiation. In WO2012/008229A, in the AED operation, similarly to the image reading operation, the read digital signal is compared with a preset irradiation start determination threshold value and it is determined that the emission of radiation has started in a case in which the digital signal is greater than the irradiation start determination threshold value. In a case in which it is determined that the emission of radiation has started, a pixel charge accumulation operation of accumulating charge in the pixel is performed while radiation is being emitted and then the image reading operation is performed. The AED function makes it possible for the sensor panel to start the pixel charge accumulation operation in synchronization with the radiation emission start timing even in a case in which a timing signal indicating the radiation emission start timing is not communicated between the radiographic image detection device and the radiation generation apparatus, for example, for the reason that the radiographic image detection device and the radiation generation apparatus are produced by different manufacturers.

In the AED operation disclosed in WO2012/008229A, nine MUXs and ADCs each of which is in charge of 256 columns of pixels operate in parallel at the same timing to read charge from all of the columns. This point is the same as that in the image reading operation.

SUMMARY OF THE INVENTION

The image reading operation ends in a case in which it reads a radiographic image corresponding to one screen once. In contrast, the AED operation is continued from before the start of the emission of radiation until the emission of radiation starts in order to wait for the start of the emission of radiation whose timing is indefinite. For example, the image reading operation ends on the order of several hundreds of milliseconds. In contrast, the AED operation is continued for a period of several seconds to several tens of seconds until an operator presses an irradiation switch for instructing the start of the emission of radiation after setting radiation emission conditions in the radiation generation apparatus.

In WO2012/008229A, while the AED operation is continued, the signal processing circuit repeats the same operation as the image reading operation that reads the charge from the pixels in all of the columns. Therefore, there is a problem that power consumption is very high for the period of the AED operation having a longer operation time than the image reading operation. In particular, in a case in which the radiographic image detection device is an electronic cassette driven by a battery and has high power consumption, since a battery having a limited charging capacity is used, the battery needs be frequently charged. Therefore, imaging efficiency is reduced.

An object of the invention is to provide a radiographic image detection device that can reduce the power consumption of a signal processing circuit in an irradiation start detection operation of detecting the start of the emission of radiation and a method for operating the radiographic image detection device.

In order to solve the above described problems, there is provided a radiographic image detection device comprising a sensor panel in which pixels that are sensitive to radiation which has been emitted from a radiation generation apparatus and transmitted through a subject and accumulate charge are two-dimensionally arranged and a plurality of signal lines for reading the charge are arranged, a signal processing circuit that reads an analog voltage signal corresponding to the charge from the pixel through the signal line to perform signal processing, a plurality of charge amplifiers that are included in the signal processing circuit and each of which is provided for each signal line, is connected to one end of the signal line, and converts the charge from the pixel into the analog voltage signal, a multiplexer that is included in the signal processing circuit, has a plurality of input terminals to which the plurality of charge amplifiers are respectively connected, sequentially selects the analog voltage signals from the plurality of charge amplifiers, and outputs the selected analog voltage signal, an AD converter that is included in the signal processing circuit, is connected to a stage behind the multiplexer, and performs an AD conversion process of converting the analog voltage signal output from the multiplexer into a digital signal corresponding to a voltage value, and a control unit that controls the signal processing circuit such that an irradiation start detection operation and an image reading operation are performed, in which the irradiation start detection operation reads the charge through a detection channel which is the signal line connected to a preset detection pixel among the pixels from before start of the emission of the radiation starts and detects the start of the emission of the radiation on the basis of the digital signal corresponding to the read charge, the image reading operation reads the charge from the pixel through the signal line after a pixel charge accumulation period for which the charge is accumulated in the pixel elapses after the start of the emission of the radiation and outputs a radiographic image which is indicated by the digital signal corresponding to the read charge and is provided for diagnosis, and in a case where power supplied to the charge amplifier in the image reading operation is normal power, in the irradiation start detection operation, the control unit causes at least one of non-detection charge amplifiers other than a detection charge amplifier that is the charge amplifier connected to the detection channel, among the plurality of charge amplifiers connected to the multiplexer to be in a power saving state in which the supply power is lower than the normal power, and drives at least one of a plurality of the detection charge amplifiers in a low power state in which power lower than the normal power and greater than 0 is supplied.

It is preferable that the power saving state is the low power state. Alternatively, it is preferable that the power saving state is a power-off state in which the supply of power is stopped.

It is preferable that the control unit causes all of the non-detection charge amplifiers to be in the power saving state during the irradiation start detection operation.

It is preferable that the radiographic image detection device further comprises a first path through which the charge is input to the charge amplifier, a second path through which the charge is output to the multiplexer without passing through the charge amplifier, and a switch that selectively switches between the first path and the second path, and the control unit controls the switch to select the second path for the non-detection charge amplifier in the power saving state.

It is preferable that in a case where the power saving state is a power-off state in which the supply of power is stopped, the control unit applies a bias voltage for stabilizing a potential of an input stage to the non-detection charge amplifier in the power-off state.

It is preferable that a plurality of blocks each of which includes one multiplexer to which at least one of the detection charge amplifiers is connected and one AD converter connected to a stage behind the one multiplexer are further comprised, in which the control unit has a function of switching a power supply state of the block between a first state in which first power is supplied and a second state in which second power lower than the first power per unit time is supplied, and periodically switches the power supply state of at least one of the plurality of blocks during the irradiation start detection operation.

It is preferable that in a case where the number of blocks whose power supply state is periodically switched is two or more, the control unit shifts a switching timing of the power supply state of at least two of the two or more blocks.

It is preferable that the two or more blocks are divided into groups, and the control unit shifts the switching timing of the power supply state for each group. In this case, it is preferable that at least one block is disposed between two blocks belonging to the same group.

It is preferable that the control unit shifts the switching timing of the power supply state of all of the two or more blocks.

It is preferable that the control unit causes at least one of the blocks including the multiplexer to which only the non-detection charge amplifier is connected to be in the second state at all the times among the plurality of blocks during the irradiation start detection operation.

It is preferable that the block is provided for each area that is formed by the pixels connected to a plurality of the adjacent signal lines. In this case, it is preferable that a plurality of the adjacent blocks that are in charge of the areas adjacent to each other are mounted on the same chip, and a plurality of the chips are provided.

It is preferable that the control unit switches the power supply state of the block in units of the blocks that are in charge of the areas or in units of the chips.

It is preferable that a temperature drift correction unit that corrects a temperature drift of the digital signal which is generated by a bias in a temperature distribution in the signal processing circuit due to the switching of the power supply state of the block is further comprised.

It is preferable that the detection pixel is a dedicated pixel which is specialized for the irradiation start detection operation.

It is preferable that the radiographic image detection device is an electronic cassette that is configured by accommodating the sensor panel and the signal processing circuit in a portable housing and is supplied with power from a battery provided in the housing.

There is provided a method for operating a radiographic image detection device comprising a sensor panel in which pixels that are sensitive to radiation which has been emitted from a radiation generation apparatus and transmitted through a subject and accumulate charge are two-dimensionally arranged and a plurality of signal lines for reading the charge are arranged, a signal processing circuit that reads an analog voltage signal corresponding to the charge from the pixel through the signal line to perform signal processing, a plurality of charge amplifiers that are included in the signal processing circuit and each of which is provided for each signal line, is connected to one end of the signal line, and converts the charge from the pixel into the analog voltage signal, a multiplexer that is included in the signal processing circuit, has a plurality of input terminals to which the plurality of charge amplifiers are respectively connected, sequentially selects the analog voltage signals from the plurality of charge amplifiers, and outputs the selected analog voltage signal, an AD converter that is included in the signal processing circuit, is connected to a stage behind the multiplexer, and performs an AD conversion process of converting the analog voltage signal output from the multiplexer into a digital signal corresponding to a voltage value, and a control unit that controls the signal processing circuit such that an irradiation start detection operation and an image reading operation are performed, the method comprising an irradiation start detection step of performing an irradiation start detection operation that reads the charge through a detection channel which is the signal line connected to a preset detection pixel among the pixels from before start of the emission of the radiation and detects the start of the emission of the radiation on the basis of the digital signal corresponding to the read charge, and an image reading step of performing an image reading operation that reads the charge from the pixel through the signal line after a pixel charge accumulation period for which the charge is accumulated in the pixel elapses from the start of the emission of the radiation and outputs a radiographic image which is indicated by the digital signal corresponding to the read charge and is provided for diagnosis, in which in a case where power supplied to the charge amplifier during the image reading step is normal power, in the irradiation start detection step, at least one of non-detection charge amplifiers other than a detection charge amplifier that is the charge amplifier connected to the detection channel, among the plurality of charge amplifiers connected to the multiplexer is caused to be in a power saving state in which the supply power is lower than the normal power, and at least one of a plurality of the detection charge amplifiers is driven in a low power state in which power lower than the normal power and greater than 0 is supplied.

According to the invention, during an irradiation start detection operation of detecting the start of the emission of radiation, at least one of non-detection charge amplifiers other than a detection charge amplifier that is the charge amplifier connected to the detection channel of a detection pixel for irradiation start detection, among the plurality of charge amplifiers connected to the multiplexer is caused to be in a power saving state in which the supply power is lower than the normal power, and at least one of a plurality of the detection charge amplifiers is driven in a low power state in which power lower than the normal power and greater than 0 is supplied. Accordingly it is possible to provide a radiographic image detection device that can reduce the power consumption of the signal processing circuit in irradiation start detection operation and a method for operating the same.

BRIEF DESCRIPTION OF THE DRAWINGS

FIG. 33A is a flowchart illustrating the procedure of driving the CDS in the image reading operation.

FIG. 33B is a flowchart illustrating the procedure of driving the CDS in the AED operation.

FIG. 40 is a flowchart illustrating the procedure of the operation of an electronic cassette according to the (2-1)-th embodiment.

FIG. 42A is a diagram illustrating the configuration of a non-detection channel in a case in which a non-detection CA is changed to a power-off state in the AED operation.

FIG. 42B is a diagram illustrating the configuration of the non-detection channel in a case in which the non-detection CA is changed to the power-off state in the image reading operation.

FIG. 49A is a diagram illustrating a circuit configuration of a detection channel in the AED operation in a (3-2)-th embodiment.

FIG. 49B is a diagram illustrating a circuit configuration of a detection channel in the image reading operation in the (3-2)-th embodiment.

DESCRIPTION OF THE PREFERRED EMBODIMENTS

1. First Invention

(1-1)-th Embodiment

Figure 1:
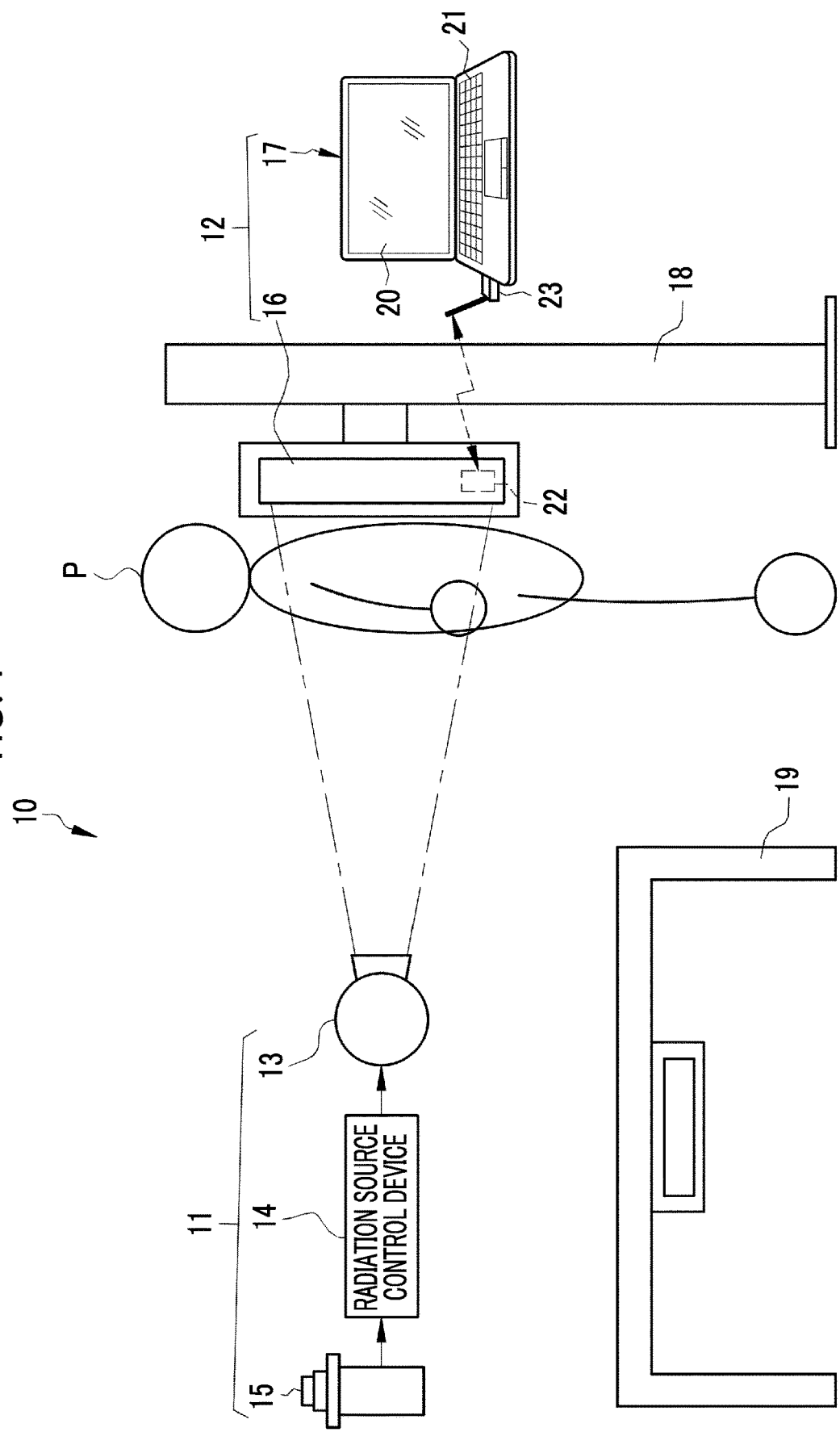
FIG. 1 is a diagram illustrating an X-ray imaging system.

In FIG. 1, an X-ray imaging system 10 that performs imaging using X-rays as radiation comprises an X-ray generation apparatus 11 and an X-ray imaging apparatus 12 and is installed in, for example, an imaging room of a radiology department in a medical facility. The X-ray generation apparatus 11 includes an X-ray source 13, a radiation source control device 14 that controls the X-ray source 13, and an irradiation switch 15 that is connected to the radiation source control device 14. The X-ray imaging apparatus 12 includes an electronic cassette 16 which is a radiographic image detection device and a console 17.

In addition to the X-ray imaging system 10, an upright imaging table 18 for capturing an image of a patient P that is a subject at an upright posture and a decubitus imaging table 19 for capturing an image of the patient P at a decubitus posture are installed in the imaging room. The X-ray source 13 is shared by the upright imaging table 18 and the decubitus imaging table 19. In addition, FIG. 1 illustrates an aspect in which the electronic cassette 16 is set in the upright imaging table 18 and an X-ray image of the patient P is captured at the upright posture.

As is well known, the X-ray source 13 includes an X-ray tube that generates X-rays and an irradiation field limiter (also referred to as a collimator) that limits the irradiation field of the X-rays generated by the X-ray tube to the patient P. The radiation source control device 14 controls the tube voltage, tube current, and X-ray emission time of the X-ray tube. The radiation source control device 14 stores in advance a plurality of types of X-ray emission conditions including the tube voltage, the tube current, and the irradiation time according to an imaging part, such as the chest or the abdomen, such that an operator selects a desired irradiation condition from the stored irradiation conditions and inputs the selected irradiation condition. The operator can finely adjust the irradiation conditions considering, for example, the body shape of the patient P.

The irradiation switch 15 is operated by the operator in a case in which the emission of X-rays starts. The irradiation switch 15 is a two-stage pressure type. In a case in which the irradiation switch 15 is pressed to the first stage (pressed halfway), the radiation source control device 14 instructs the X-ray source 13 to start a preparation operation before X-rays are emitted. In a case in which the irradiation switch 15 is pressed to the second stage (pressed fully), the radiation source control device 14 instructs the X-ray source 13 to start the emission of X-rays. The radiation source control device 14 includes a timer that starts to measure time in a case in which the emission of X-rays is started and stops the emission of X-rays by the X-ray source 13 in a case in which the time measured by the timer reaches the irradiation time set in the irradiation conditions.

The electronic cassette 16 detects an X-ray image based on the X-rays that have been emitted from the X-ray source 13 and then transmitted through the patient P. For example, the console 17 is configured by installing a control program, such as an operating system, or various application programs in a computer, such as a notebook personal computer. The console 17 includes a display 20 and an input device 21 such as a touch pad or a keyboard. The console 17 displays various operation screens provided with an operation function based on a graphical user interface (GUI) on the display 20 and receives various operation commands input from the input device 21 by the operator through the various operation screens.

The electronic cassette 16 and the console 17 comprise wireless communication units 22 and 23 for performing wireless communication therebetween, respectively. The electronic cassette 16 and the console 17 transmit and receive various kinds of information including an imaging menu or X-ray images through the wireless communication units 22 and 23, using wireless communication.

Each of the wireless communication units 22 and 23 includes, for example, an antenna, a modulation and demodulation circuit, and a transmission control unit. The modulation and demodulation circuit performs modulation for imposing data to be transmitted onto a carrier wave (also referred to as a carrier) and demodulation for extracting data from the carrier wave received by the antenna. The transmission control unit performs transmission control based on a wireless local area network (LAN).

The console 17 receives the input of an imaging order to command the operator to perform X-ray imaging. For example, the imaging order is input from a radiology information system (RIS) (not illustrated) to the console 17.

Figure 2:
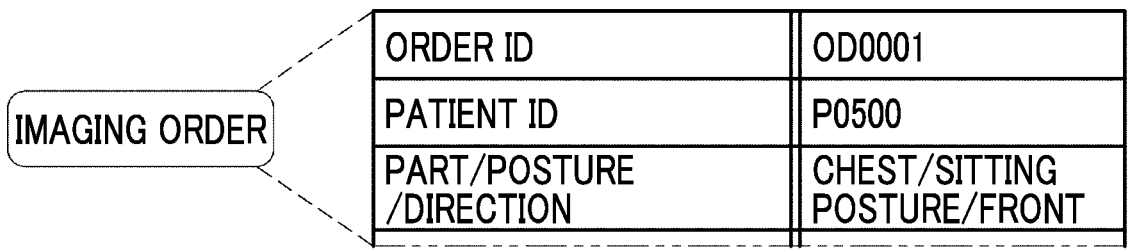
FIG. 2 is a diagram illustrating an imaging order.

In FIG. 2, the imaging order has items, such as an order ID (identification data), a patient ID, and an imaging part/posture/direction. The order ID is a symbol or a number for identifying each imaging order and is automatically assigned by the RIS. A patient ID of the patient P that is an imaging target is written in the patient ID item. The patient ID is a symbol or a number for identifying each patient P.

The imaging part, posture, and imaging direction designated by the doctor who has issued the imaging order are written in the imaging part/posture/direction item. The imaging part is a part of the human body, such as the head, the cervical vertebra, the chest, the abdomen, a hand, a finger, the elbow, or the knee. The posture is the posture of the patient P, such as an upright posture, a decubitus posture, or a sitting posture and the imaging direction is the direction of the patient P with respect to X-rays, such as the front, the side, and the back. The imaging order includes patient information items (not illustrated), such as the name, sex, age, height, and weight of the patient P, in addition to the above-mentioned items. In addition, items including a diagnosis and treatment department that has issued the imaging order, the doctor who has issued the imaging order, the date and time when the imaging order was received by the RIS, the purpose of imaging, such as postoperative follow-up or therapeutic effect evaluation, and items to be handed over from the doctor to the operator may be provided.

One imaging order may be issued for one patient P or a plurality of imaging orders may be issued for one patient P at the same time. In a case in which a plurality of imaging orders are issued for one patient P at the same time, an identification code indicating that the imaging orders are for one patient P is attached to the order IDs of the plurality of imaging orders.

Figure 3:
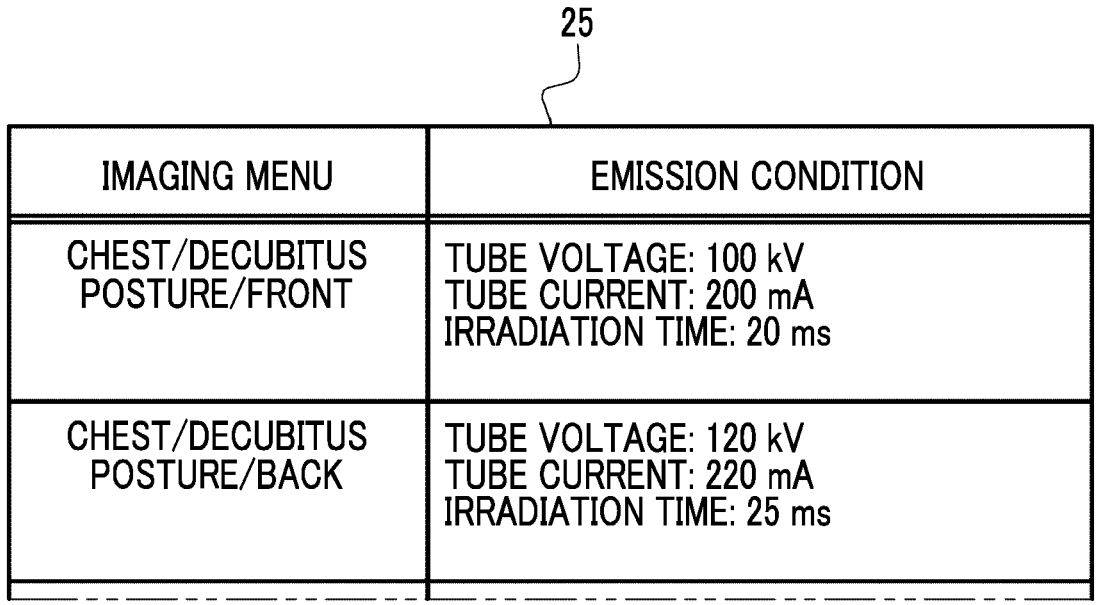
FIG. 3 is a diagram illustrating a menu and condition table.

The console 17 stores a menu and condition table 25 illustrated in FIG. 3. An imaging menu having a set of the imaging part, the posture, and the imaging direction and irradiation conditions corresponding to the imaging menu are registered in the menu and condition table 25 so as to be association with each other. In addition, an imaging menu having a set of the imaging part and the imaging direction obtained by excluding the posture from the above-mentioned imaging menu or an imaging menu corresponding to special imaging, such as tomosynthesis imaging, may be provided.

The console 17 displays an imaging order list which is a list of the content of the imaging order illustrated in FIG. 2 on the display in response to the operation of the operator. The operator browses the imaging order list and checks the content of the imaging order. Then, the console 17 displays the content of the menu and condition table 25 on the display in a form in which the imaging menu can be set. The operator selects an imaging menu matched with the imaging part/posture/direction designated by the imaging order and sets the imaging menu. In addition, the operator sets the irradiation conditions matched with the irradiation conditions corresponding to the selected imaging menu in the radiation source control device 14.

The console 17 transmits various kinds of information, such as the imaging menu set by the operator, the irradiation conditions corresponding to the set imaging menu, the order ID, and a console ID which is a symbol or a number for identifying the console, as imaging preparation commands to the electronic cassette 16 through the wireless communication unit 23.

In addition, the console 17 converts the X-ray image from the electronic cassette 16 into an image file with a format based on, for example, the Digital Imaging and Communication in Medicine (DICOM) standard and transmits the image file to a picture archiving and communication system (PACS) (not illustrated). In the image file, the X-ray image and image accessory information including, for example, an order ID, patient information, an imaging menu, irradiation conditions, and a cassette ID which is a symbol or a number for identifying the electronic cassette 16 are associated with one image ID. The doctor in the diagnosis and treatment department that has issued the imaging order can access the PACS with a terminal in the diagnosis and treatment department, download the image file, and browse the X-ray image.

Figure 4:
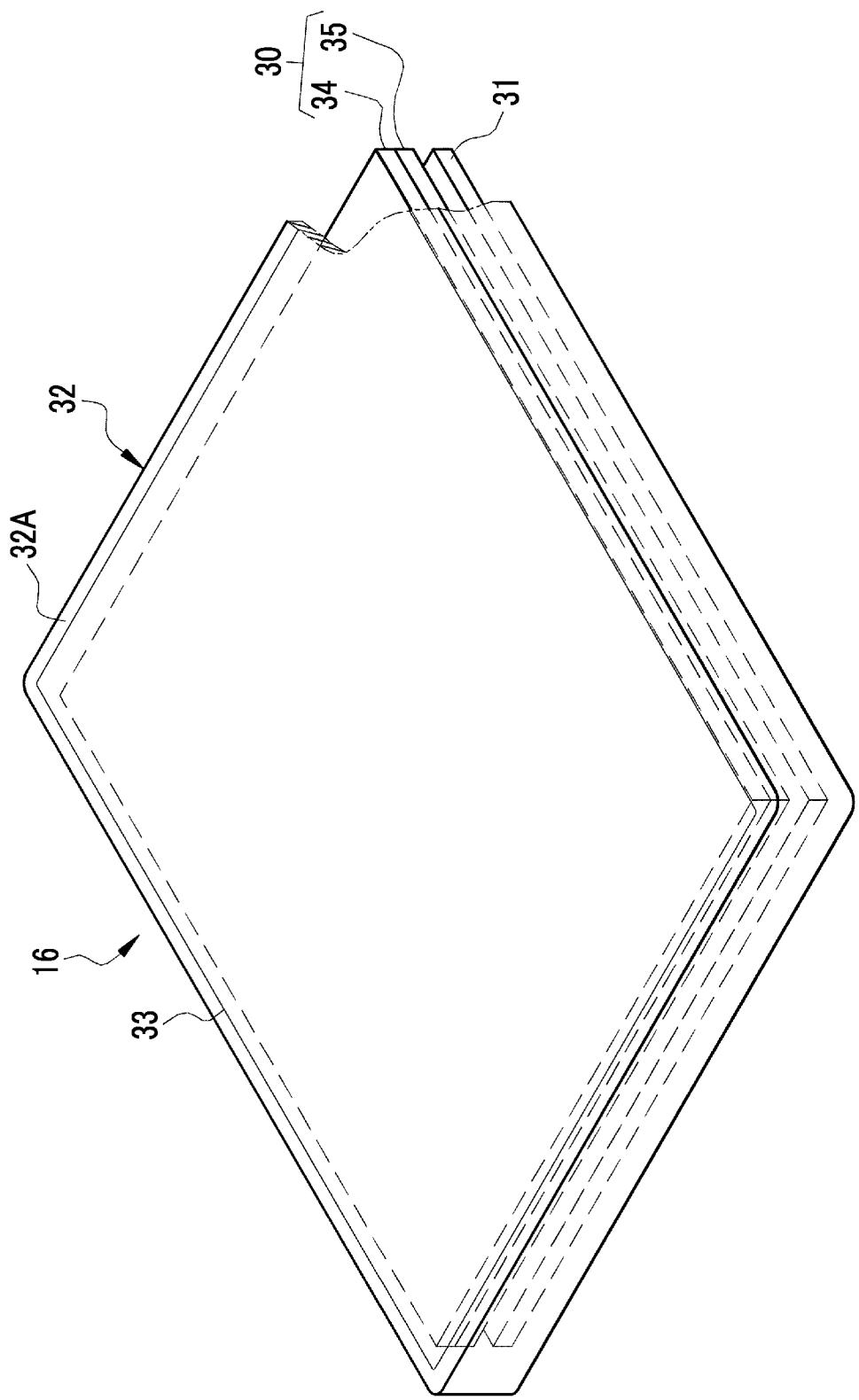
FIG. 4 is an external perspective view illustrating an electronic cassette.

In FIG. 4, the electronic cassette 16 includes a sensor panel 30, a circuit unit 31, and a portable housing 32 that has a rectangular parallelepiped shape and accommodates the sensor panel 30 and the circuit unit 31. The housing 32 has a size that is based on the International Organization for Standardization (ISO) 4090:2001 and is almost the same as that of, for example, a film cassette, an imaging plate (IP) cassette, or a computed radiography (CR) cassette. The housing 32 accommodates, for example, a battery 65 (see FIG. 5) that supplies power to the wireless communication unit 22 and each unit of the electronic cassette 16 and a wired communication unit 66 (see FIG. 5) that is connected to the console 17 through a cable in a wired manner, in addition to the sensor panel 30 and the circuit unit 31. In a case in which the wireless communication unit 22 is used, the electronic cassette 16 is driven by power from the battery 65 and can be used in a so-called wireless manner.

A rectangular opening is formed in a front surface 32A of the housing 32 and a transmission plate 33 that transmits X-rays is attached to the opening. The electronic cassette 16 is positioned at a posture where the front surface 32A faces the X-ray source 13. The housing 32 is provided with a switch for switching between turn-on and the turn-off the power supply or an indicator for indicating an operation state of the electronic cassette 16 such as the remaining usage time of the battery 65 or an imaging preparation completion state.

The sensor panel 30 includes a scintillator 34 and a light detection substrate 35. The scintillator 34 and the light detection substrate 35 are stacked in the order of the scintillator 34 and the light detection substrate 35 as viewed from the front surface 32A on which X-rays are incident. The scintillator 34 includes a phosphor, such as thallium activated cesium iodide (CsI:Tl) or terbium activated gadolinium oxysulfide ($Gd_2O_2S$:Tb (GOS)), converts X-rays incident through the transmission plate 33 into visible light, and emits the visible light. In addition, a sensor panel in which the light detection substrate 35 and the scintillator 34 are stacked in this order as viewed from the front surface 32A on which X-rays are incident may be used. Further, a direct-conversion-type sensor panel may be used which directly converts X-rays into charge using a photoconductive film such as amorphous selenium.

The light detection substrate 35 detects the visible light emitted from the scintillator 34 and converts the visible light into charge. The circuit unit 31 controls the driving of the light detection substrate 35 and generates an X-ray image on the basis of the charge output from the light detection substrate 35.

Figure 5:
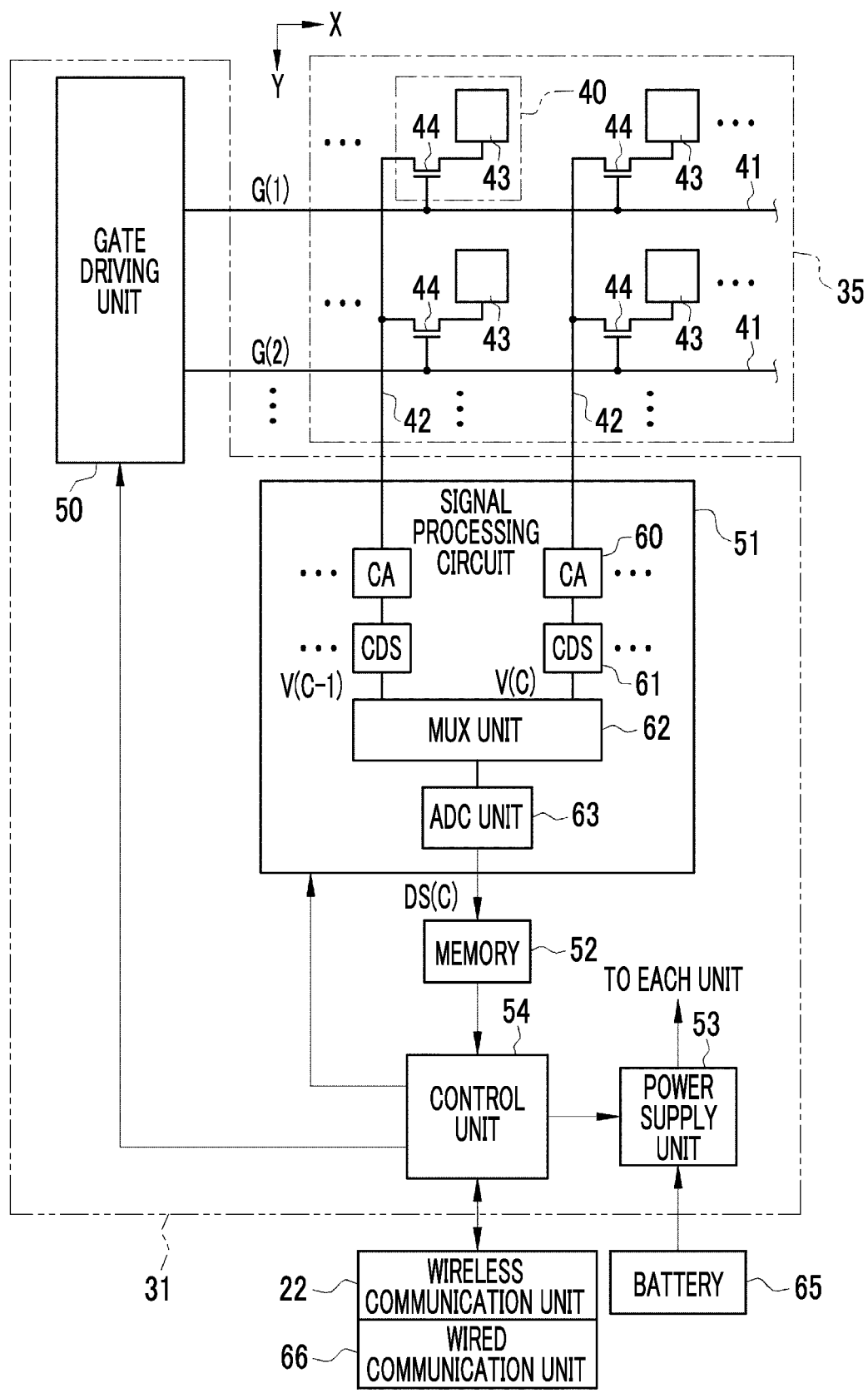
FIG. 5 is a block diagram illustrating an electrical configuration of the electronic cassette.

In FIG. 5, the light detection substrate 35 is configured by providing pixels 40 which are arranged in a two-dimensional matrix of N rows and M columns, N gate lines 41, and M signal lines 42 on a glass substrate (not illustrated). The gate lines 41 extend in the X direction along the row direction of the pixels 40 and are arranged at predetermined pitches in the Y direction along the column direction of the pixels 40. The signal lines 42 extend in the Y direction and are arranged at predetermined pitches in the X direction. The gate lines 41 and the signal lines 42 are orthogonal to each other and the pixels 40 are provided at the intersection points between the gate lines 41 and the signal lines 42.

Here, N and M are integers equal to or greater than 2. In this example, a case in which N is 2880 and M is 2304 (see FIG. 7) will be described. The numbers of rows and columns of the pixels 40 are not limited thereto. The array of the pixels 40 may not be a square array as illustrated in FIG. 5. Alternatively, the pixels 40 may be inclined at an angle of 45° and may be arranged in zigzag.

As is well known, each pixel 40 comprises a photoelectric conversion unit 43 on which visible light is incident and which generates charge (electronic-hole pair) and accumulates the charge and a thin film transistor (TFT) 44 which is a switching element. The photoelectric conversion unit 43 has a structure in which an upper electrode and a lower electrode are provided on the upper and lower sides of a semiconductor layer that generates charge. The semiconductor layer is, for example, a p-intrinsic-n (PIN) type. An N-type layer is formed on the upper electrode side and a P-type layer is formed on the lower electrode side. The TFT 44 has a gate electrode connected to the gate line 41, a source electrode connected to the signal line 42, and a drain electrode connected to the lower electrode of the photoelectric conversion unit 43. Instead of the TFT type, a complementary metal oxide semiconductor (CMOS) sensor panel may be used as the switching element.

A bias line (not illustrated) is connected to the upper electrode of the photoelectric conversion unit 43. A positive bias voltage is applied to the upper electrode through the bias line. The electric field is generated in the semiconductor layer by the application of the positive bias voltage. Therefore, among the electronic-hole pairs generated in the semiconductor layer by photoelectric conversion, the electron is moved to the upper electrode and is then absorbed to the bias line and the hole is moved to the lower electrode and is collected as charge.

The circuit unit 31 is provided with a gate driving unit 50, a signal processing circuit 51, a memory 52, a power supply unit 53, and a control unit 54 that controls these units.

The gate driving unit 50 is connected to the end of each gate line 41 and generates a gate pulse G(R) (R=1 to N) for driving the TFT 44. The control unit 54 drives the TFT 44 through the gate driving unit 50 and controls the signal processing circuit 51 so as to perform a pixel reset operation which reads dark charge from the pixel 40 and resets (discard) the dark charge, a pixel charge accumulation operation which accumulates charge corresponding to the amount of incident X-rays in the pixel 40, an image reading operation which reads an X-ray image for diagnosis, and an AED operation which detects the start of the emission of X-rays.

The image reading operation is an operation which reads charge from the pixel 40 through the signal line 42 after a pixel charge accumulation period elapses from the start of the emission of X-rays and outputs an X-ray image represented by a digital signal corresponding to the read charge. The AED operation is an operation which reads the charge from the pixel 40 through the signal line 42 from before the start of the emission of X-rays and detects the start of the emission of X-rays on the basis of a digital signal corresponding to the read charge.

The signal processing circuit 51 reads an analog voltage signal V(C) (C=1 to M) corresponding to the charge from the pixel 40 through the signal line 42 to perform signal processing. The signal processing circuit 51 includes a CA 60, a correlated double sampling circuit (hereinafter, referred to as a CDS) 61, a MUX unit 62, and an ADC unit 63.

The CA 60 is provided for each signal line 42 and is connected to one end of the signal line 42. The CA 60 outputs the analog voltage signal V(C) corresponding to the charge input from the pixel 40 through the signal line 42. The CDS 61 is provided for each signal line 42, similarly to the CA 60. The CDS 61 performs a known correlated double sampling process for the analog voltage signal V(C) from the CA 60 to remove a reset noise component of the CA 60 from the analog voltage signal V(C).

The CA 60 is connected to the MUX unit 62. The CDS 61 is provided between the CA 60 and the MUX unit 62. In addition, the ADC unit 63 is connected to a stage behind the MUX unit 62. The MUX unit 62 sequentially selects the analog voltage signals V(C) input from a plurality of CAs 60 through the CDSs 61 and outputs the selected analog voltage signal V(C) to the ADC unit 63. The ADC unit 63 performs an AD conversion process that converts the analog voltage signal V(C) from the MUX unit 62 into a digital signal DS(C) corresponding to the voltage value of the analog voltage signal V(C). Then, the ADC unit 63 outputs the converted digital signal DS(C) to the memory 52. The memory 52 stores the digital signal DS(C) from the ADC unit 63. The memory 52 has a capacity to store an X-ray image corresponding to at least one screen.

The power supply unit 53 supplies power from the battery 65 to each unit under the control of the control unit 54. For example, the battery 65 is attachably and detachably provided on the rear surface opposite to the front surface 32A of the housing 32.

The control unit 54 receives various kinds of information from the console 17 through the wireless communication unit 22 or the wired communication unit 66 and performs control corresponding to the various kinds of information. For example, the control unit 54 changes the processing conditions of the signal processing circuit 51 according to the irradiation conditions.

Figure 6:
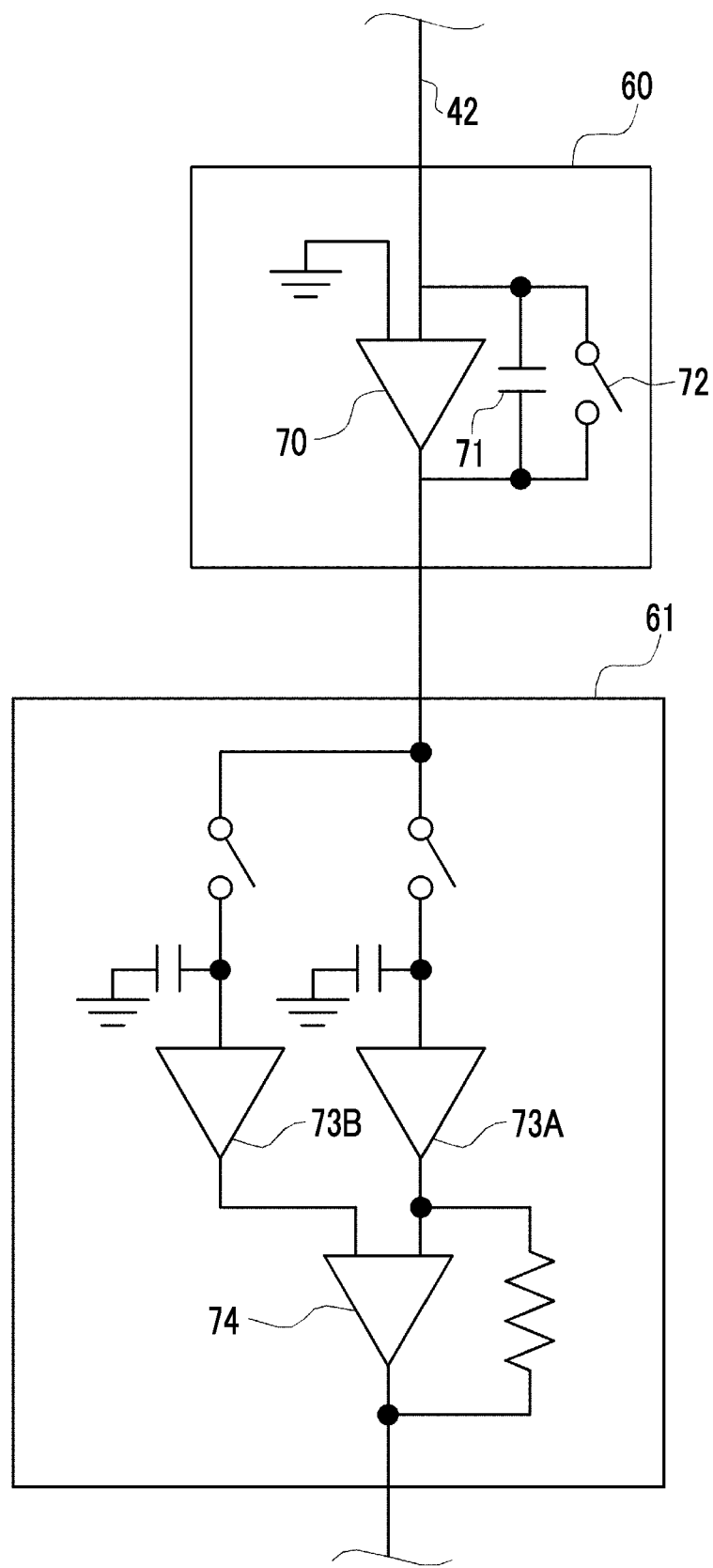
FIG. 6 is a circuit diagram illustrating a CA and a CDS.

In FIG. 6, the CA 60 includes an operational amplifier 70, a capacitor 71, and an amplifier reset switch 72. The operational amplifier 70 has two input terminals and one output terminal. The signal line 42 is connected to one of the two input terminals and a ground line is connected to the other input terminal. The capacitor 71 and the amplifier reset switch 72 are connected in parallel between the input terminal to which the signal line 42 is connected and the output terminal.

The CA 60 accumulates the charge input from the signal line 42 in the capacitor 71 to integrate the charge and outputs a voltage value corresponding to the integrated value, that is, the analog voltage signal V(C). The driving of the amplifier reset switch 72 is controlled by the control unit 54. The amplifier reset switch 72 is turned on to reset (discard) the charge accumulated in the capacitor 71.

The CDS 61 includes a first sample-and-hold circuit (hereinafter, abbreviated to S/H) 73A, a second S/H 73B, and a difference amplifier 74. The first S/H 73A samples and holds the reset noise component of the CA 60 in a case in which the TFT 44 is in an off state. The second S/H 73B samples and holds the analog voltage signal V(C) output from the CA 60 on the basis of the charge input in a case in which the TFT 44 is in an on state. The difference amplifier 74 calculates the difference between the reset noise components held in the S/Hs 73A and 73B and the analog voltage signal V(C). Therefore, the analog voltage signal V(C) from which noise has been removed is output.

Figure 7:
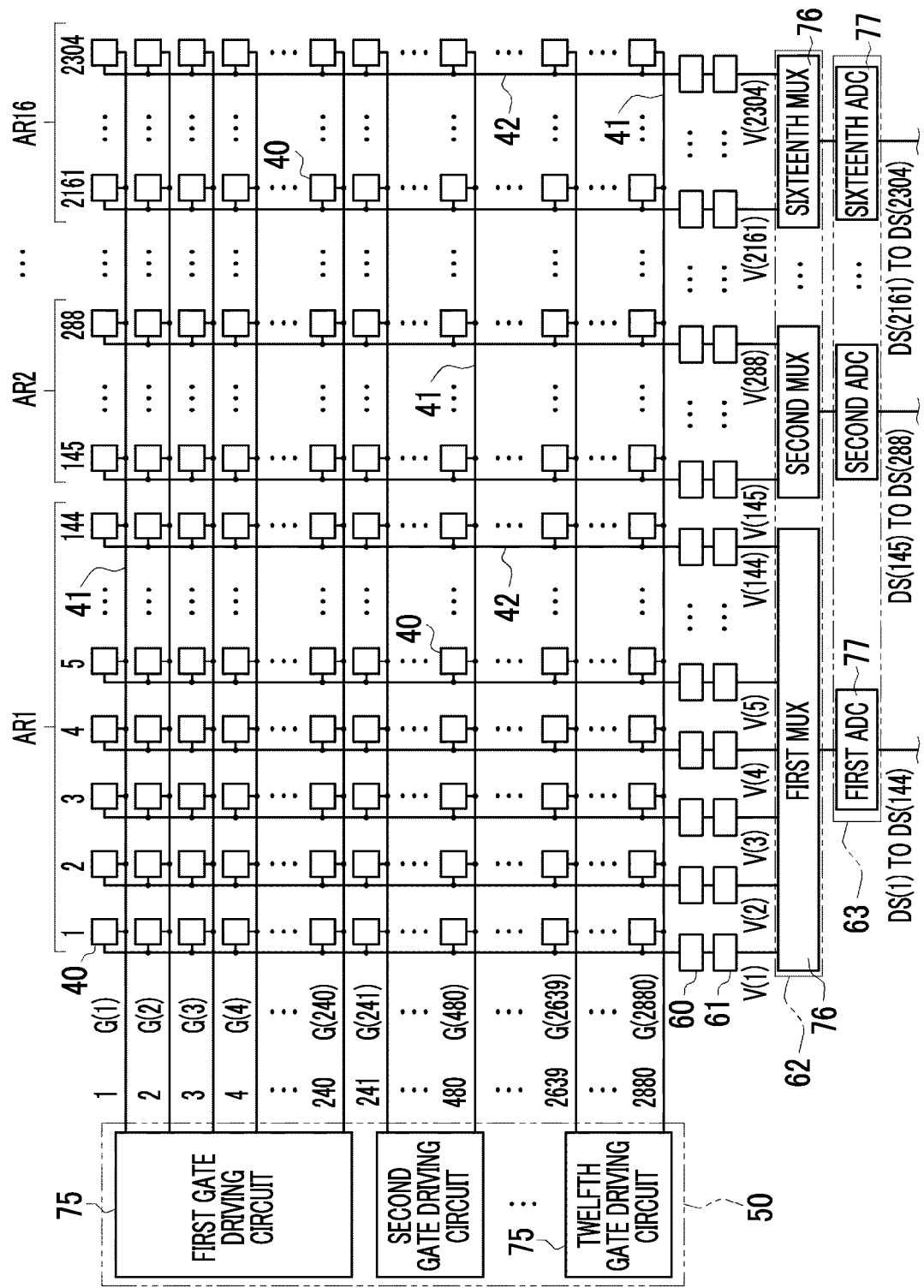
FIG. 7 is a block diagram illustrating a gate driving unit, a MUX unit, and an ADC unit in detail.

In FIG. 7, the gate driving unit 50 includes, for example, a total of 12 gate driving circuits 75, that is, the first to twelfth gate driving circuits 75. Each gate driving circuit 75 corresponds to each gate line 41. Since N which is the number of rows of pixels 40 is 2880, 240 (=2880/12) gate lines 41 are connected to one gate driving circuit 75. For example, the gate lines 41 corresponding to the first to 240th rows of the pixels 40 are connected to the first gate driving circuit 75 and the gate lines 41 corresponding to the 241st to 480th rows of the pixels 40 are connected to the second gate driving circuit 75. One gate driving circuit 75 is in charge of reading charge from 240 rows of the pixels 40.

The MUX unit 62 includes, for example, a total of 16 MUXs 76, that is, the first to sixteenth MUXs 76. Each MUX 76 corresponds to each signal line 42. Since M which is the number of columns of the pixels 40 is 2304, 144 (=2304/16) signal lines 42 are connected to one MUX 76. For example, the signal lines 42 corresponding to the first to 144th columns of the pixels 40 are connected to the first MUX 76 and the signal lines 42 corresponding to the 145th to 288th columns of the pixels 40 are connected to the second MUX 76. Therefore, one MUX 76 selectively outputs the analog voltage signals V(C) based on the charge from 144 columns of the pixels 40. Hereinafter, an area formed by the pixels 40 connected to a plurality of adjacent signal lines 42 is referred to as an area AR (AR1 to AR16).

Each MUX 76 includes a plurality of input terminals. A plurality of CAs 60 are connected to the plurality of input terminals with the CDSs 61 interposed therebetween.

The ADC unit 63 includes a total of 16 ADCs 77, that is, the first to sixteenth ADCs 77, similarly to the first to sixteenth MUXs 76 of the MUX unit 62. The first to sixteenth ADCs 77 are connected to a stage behind the first to sixteenth MUXs 76. Since the first to sixteenth MUXs 76 are provided so as to correspond to the areas AR1 to AR16, respectively, the first to sixteenth ADCs 77 are also provided so as to correspond to the areas AR1 to AR16, respectively.

One ADC 77 is in charge of an AD conversion process into the digital signals DS(V) based on the charge from 144 columns of the pixels 40. For example, the first ADC 77 converts the analog voltage signals V(1) to V(144) sequentially output from the first MUX 76 into the digital signals DS(1) to DS(144) and the second ADC 77 converts the analog voltage signals V(145) to V(288) sequentially output from the second MUX 76 into the digital signal DS(145) to DS(288).

Figure 8:
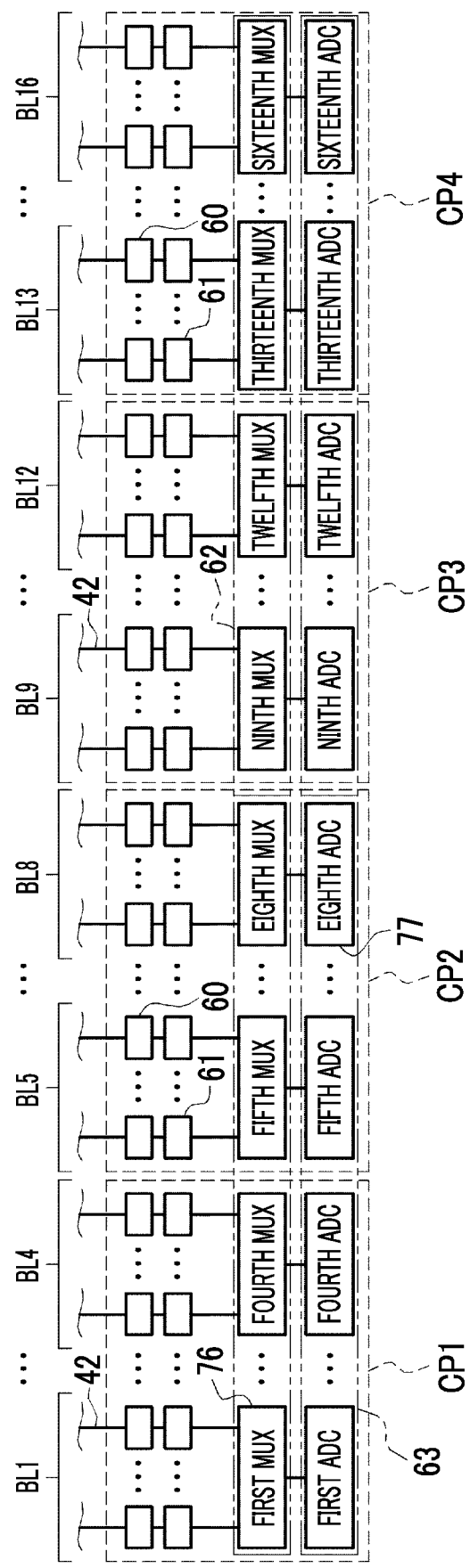
FIG. 8 is a diagram illustrating a chip on which four adjacent ADCs that are in charge of adjacent areas are mounted.

As illustrated in FIG. 8, one MUX 76, a plurality of CAs 60 and CDSs 61 connected to the input terminals of the MUX 76, and one ADC 77 connected to the output terminal of the MUX 76 form one block BL. There are 16 blocks BL whose number is the same as the number of areas AR.

As represented by a dashed line, blocks BL1 to BL4 formed by the CAs 60, the CDSs 61, the MUXs (first to fourth MUXs) 76, and the ADCs (first to fourth ADCs) 77 that take charge of each of four adjacent areas AR1 to AR4 are mounted on the same chip CP1. Similarly, blocks BL5 to BL8 formed by the CAs 60, the CDSs 61, the MUXs (fifth to eighth MUXs) 76, and the ADCs (fifth to eighth ADCs) 77 that take charge of each of areas AR5 to AR8 are mounted on a chip CP2. Blocks BL9 to BL12 formed by the CAs 60, the CDSs 61, the MUXs (ninth to twelfth MUXs) 76, and the ADCs (ninth to twelfth ADCs) 77 that take charge of each of areas AR9 to AR12 are mounted on a chip CP3. Blocks BL13 to BL16 formed by the CAs 60, the CDSs 61, the MUXs (thirteenth to sixteenth MUXs) 76, and the ADCs (thirteenth to sixteenth ADCs) 77 that take charge of each of areas AR13 to AR16 are mounted on a chip CP4. These chips CP1 to CP4 are physically completely separated from each other.

The number of gate driving circuits 75 and the number of rows of the pixels 40 that one gate driving circuit 75 is in charge of are not limited to 12 and 240 in this example, respectively. Similarly, the number of MUXs 76 and ADCs 77 (the number of blocks BL), the number of columns of the pixels 40 that one MUX 76 and one ADC 77 are in charge of (the number of columns of the pixels 40 included in one block BL), and the number of blocks BL forming one chip CP are not limited to this example and may be any values. For example, the number of columns of the pixels 40 included in one block BL may be 256 and the number of blocks BL may be 9. In addition, the number of columns of the pixels 40 included in one block BL may be 128 and the number of blocks BL may be 18.

Figure 9:
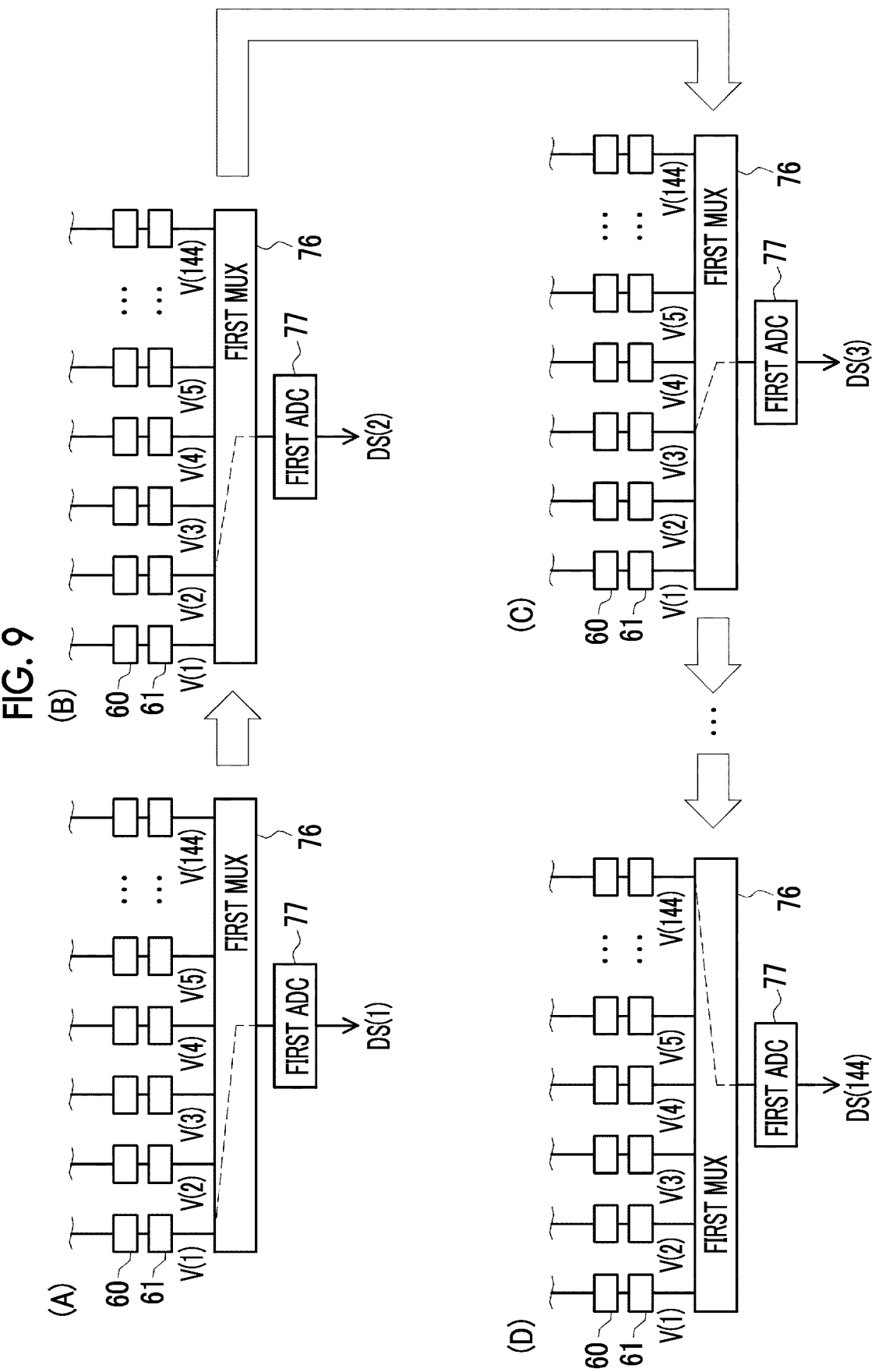
FIG. 9 is a diagram illustrating the procedure of the reading of a digital signal by a first MUX and a first ADC. (A) of FIG. 9 illustrates an aspect in which a digital signal corresponding to a first column is read, (B) of FIG. 9 illustrates an aspect in which a digital signal corresponding to a second column is read, (C) of FIG. 9 illustrates an aspect in which a digital signal corresponding to a third column is read, and (D) of FIG. 9 illustrates an aspect in which a digital signal corresponding to a 144th column is read.

FIG. 9 illustrates, for example, a procedure of reading the digital signals DS(1) to DS(144) in the area AR1 corresponding to the first to 144th columns. FIG. 9 illustrates a state in which the analog voltage signals V(1) to V(144), from which reset noise has been removed and which correspond to the charge read from the pixels 40 through the signal lines 42, appear in the output terminals of the CDSs 61.

In this state, first, as illustrated in (A) of FIG. 9, the first MUX 76 selects the analog voltage signal V(1) corresponding to the first column. Then, the analog voltage signal V(1) is input to the first ADC 77 and the first ADC 77 converts the analog voltage signal V(1) into the digital signal DS(1). Then, as illustrated in (B) of FIG. 9, the first MUX 76 selects the analog voltage signal V(2) corresponding to the second column. Then, the analog voltage signal V(2) is input to the first ADC 77 and the first ADC 77 converts the analog voltage signal V(2) into the digital signal DS(2). Then, as illustrated in (C) of FIG. 9, the first MUX 76 selects the analog voltage signal V(3) corresponding to the third column. Then, the analog voltage signal V(3) is input to the first ADC 77 and the first ADC 77 converts the analog voltage signal V(3) into the digital signal DS(3).

This series of operations is repeatedly performed in the first MUX 76 and the first ADC 77. Finally, as illustrated in (D) of FIG. 9, the analog voltage signal V(144) corresponding to the 144th column is converted into the digital signal DS(144) and the reading of the digital signals DS(1) to DS(144) in the area AR1 corresponding to the first to 144th columns ends. This holds for each MUX 76 and each ADC 77 in the other areas AR2 to AR16.

Figure 10:
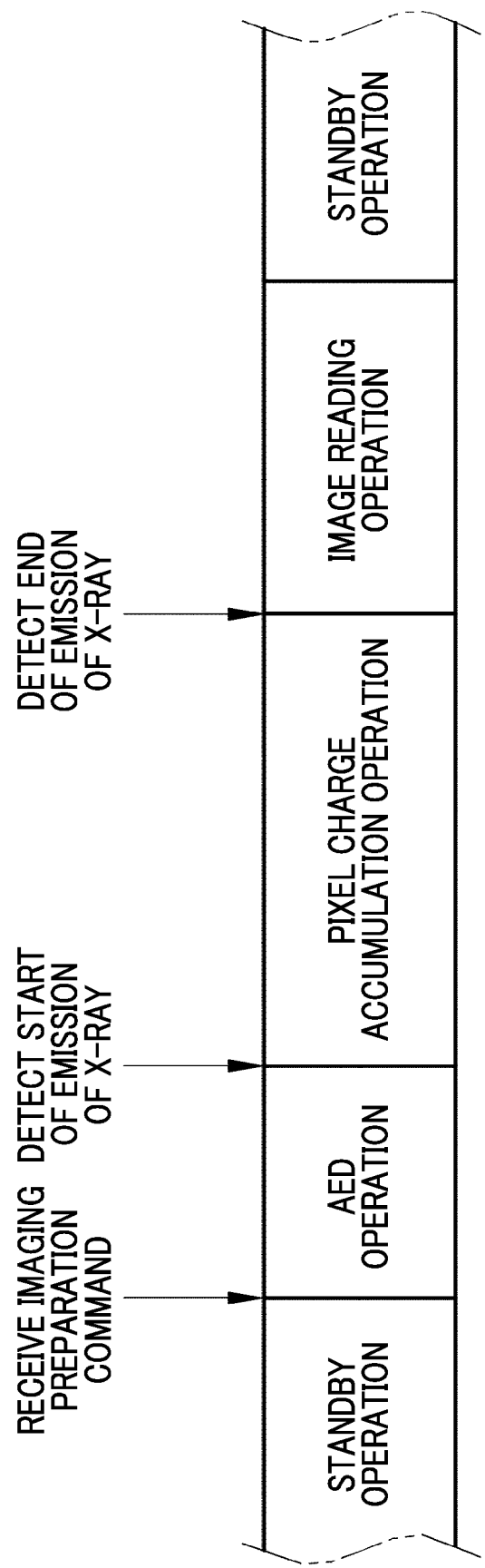
FIG. 10 is a diagram illustrating the flow of an operation performed by a control unit.

As illustrated in FIG. 10, the control unit 54 starts the AED operation in a case in which it receives an imaging preparation command in various kinds of information including the imaging menu from the console 17 from the wireless communication unit 22 or the wired communication unit 66. In the AED operation, the charge generated by the photoelectric conversion unit 43 of the pixel 40 is converted into the digital signal DS(C) by the signal processing circuit 51 and is then stored in the memory 52. Hereinafter, the digital signal DS(C) stored in the memory 52 by the AED operation is referred to as a dose signal DDS(C). The control unit 54 performs a standby operation before it receives the imaging preparation command. The standby operation is a state in which only a bias voltage is applied to the upper electrode of the photoelectric conversion unit 43 and no power is supplied to, for example, the signal processing circuit 51.

The dose signal DDS(C) is repeatedly read at predetermined intervals. The dose signal DDS(C) obtained by one reading operation corresponds to the incident dose of X-rays per unit time. In a case in which the emission of X-rays starts, the incident dose of X-rays per unit time increases gradually. Therefore, the value of the dose signal DDS (C) also increases with the increase in the incident dose.

Whenever the dose signal DDS(C) is stored in the memory 52, the control unit 54 reads the dose signal DDS(C) from the memory 52 and compares the dose signal DDS(C) with a predetermined irradiation start determination threshold value. In a case in which the dose signal DDS(C) is greater than the irradiation start determination threshold value, the control unit 54 determines that the emission of X-rays has started. Therefore, the electronic cassette 16 can detect the start of the emission of X-rays, without receiving the timing signal for indicating the emission start timing of X-rays from the radiation source control device 14.

In a case in which the start of the emission of X-rays has been detected, the control unit 54 performs a pixel reset operation (not illustrated in FIG. 10) and then performs a pixel charge accumulation operation. The control unit 54 includes a timer that starts the measurement of time in a case in which the start of the emission of X-rays has been detected, similarly to the radiation source control device 14, and determines that the emission of X-rays has ended in a case in which the time measured by the timer has reached the irradiation time of the irradiation conditions set in the console 17. In a case in which the control unit 54 detects the end of the emission of X-rays, it ends the pixel charge accumulation operation and performs an image reading operation. In this way, one X-ray imaging operation for obtaining an X-ray image corresponding to one screen ends. After the image reading operation ends, the control unit 54 returns to the standby operation again.

Figure 11:
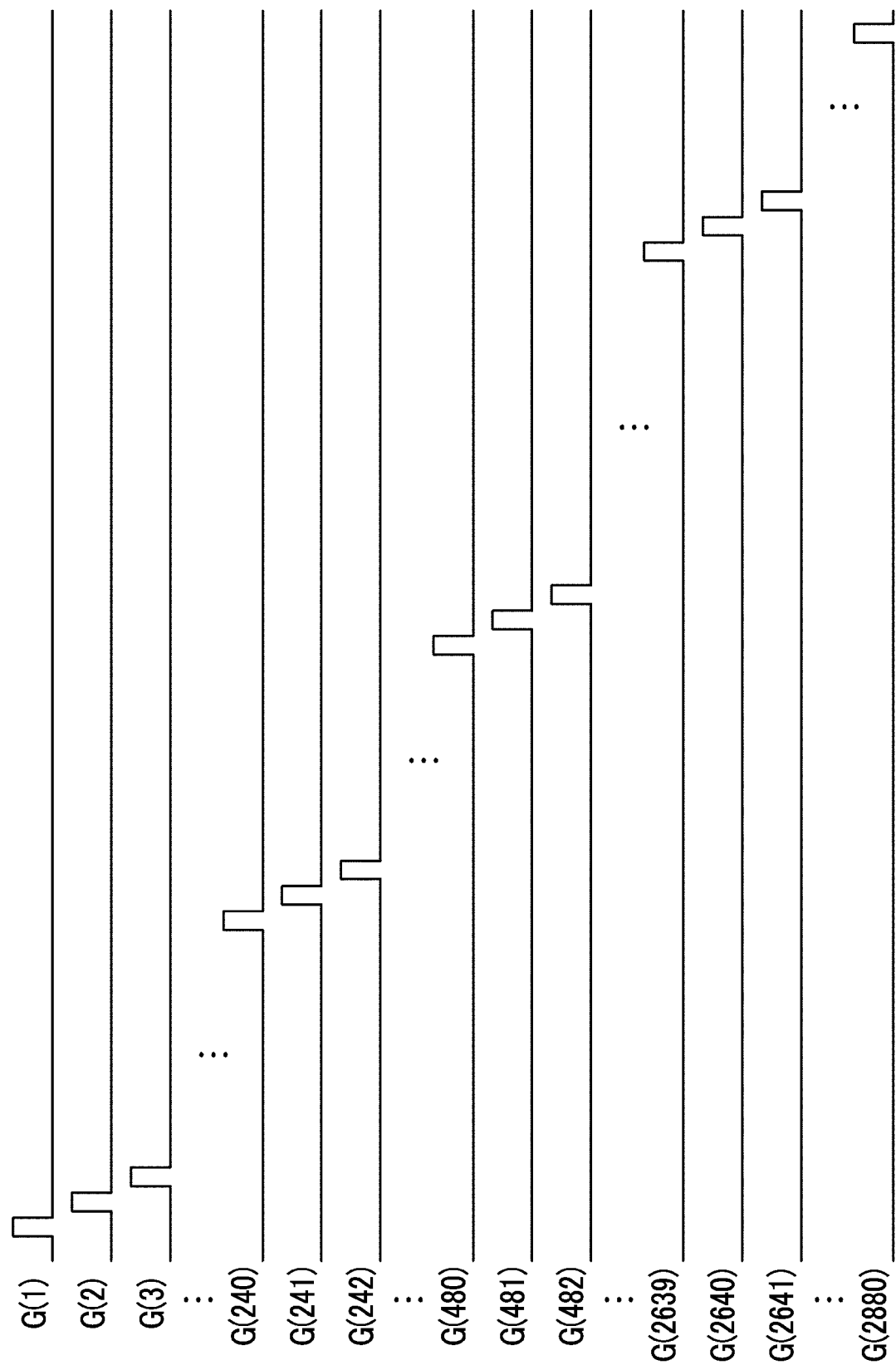
FIG. 11 is a diagram illustrating gate pulses in a pixel reset operation and an image reading operation.

As illustrated in FIG. 11, in the pixel reset operation and the image reading operation, the gate driving circuit 75 sequentially applies the gate pulse G(R) to each of the first to 2880th gate lines 41. In the pixel reset operation, charge flows from the pixel 40 to the capacitor 71 of the CA 60 through the signal line 42 and is accumulated in the capacitor 71. The charge is discarded by the amplifier reset switch 72 without being read.

In contrast, in the image reading operation, as illustrated in FIG. 9, the digital signal DS(C) based on the charge from the pixel 40 is read and stored as an X-ray image provided for diagnosis in the memory 52. Hereinafter, the digital signal DS(C) read by the image reading operation is represented by an image signal DIS(C) so as to be distinguished from the dose signal DDS(C) in the AED operation.

Figure 12:
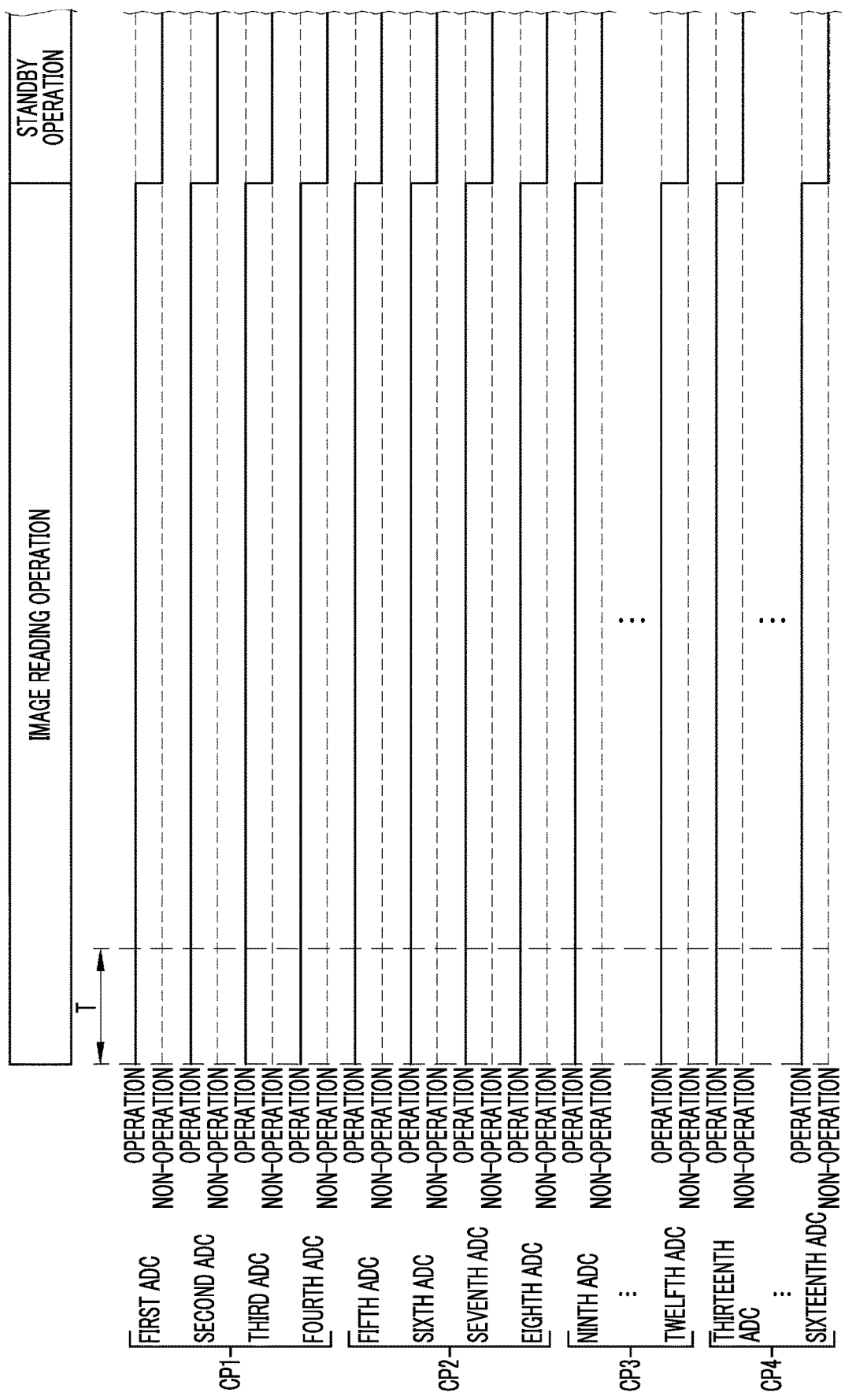
FIG. 12 is a diagram illustrating a power supply state of the ADC in the image reading operation.

As illustrated in FIG. 12, the control unit 54 changes all of the first to sixteenth ADCs 77 to an operating state (corresponding to a first state) during the image reading operation. Then, the control unit 54 operates the first to sixteenth ADCs 77 in parallel at the same timing during the image reading operation. The control unit 54 also changes the first to sixteenth MUXs 76 connected to the first to sixteenth ADCs 77 to the operating state during the image reading operation and operates the first to sixteenth MUXs 76 in parallel at the same time. Therefore, in the image reading operation, the image signals DIS(C) corresponding to the same columns are sequentially read at the same timing from the first column to the last column in each of the areas AR1 to AR16. For example, the image signals DIS(1), DIS(145), DIS(289), . . . , DIS(2161) corresponding to the first column, the 145th column, the 289th column, . . . , the 2161st column which are the first columns in the areas AR1 to AR16 are read at the same timing. In addition, all of the CAs 60 and the CDSs 61 connected to the first to sixteenth MUXs 76 are also changed to the operating state during the image reading operation.

In the standby operation after the image reading operation ends, the control unit 54 changes all of the first to sixteenth ADCs 77 to a non-operating state (corresponding to a second state). All of the first to sixteenth MUXs 76, the CAs 60, and the CDSs 61 are changed to the non-operating state during the standby operation.

Figure 13:
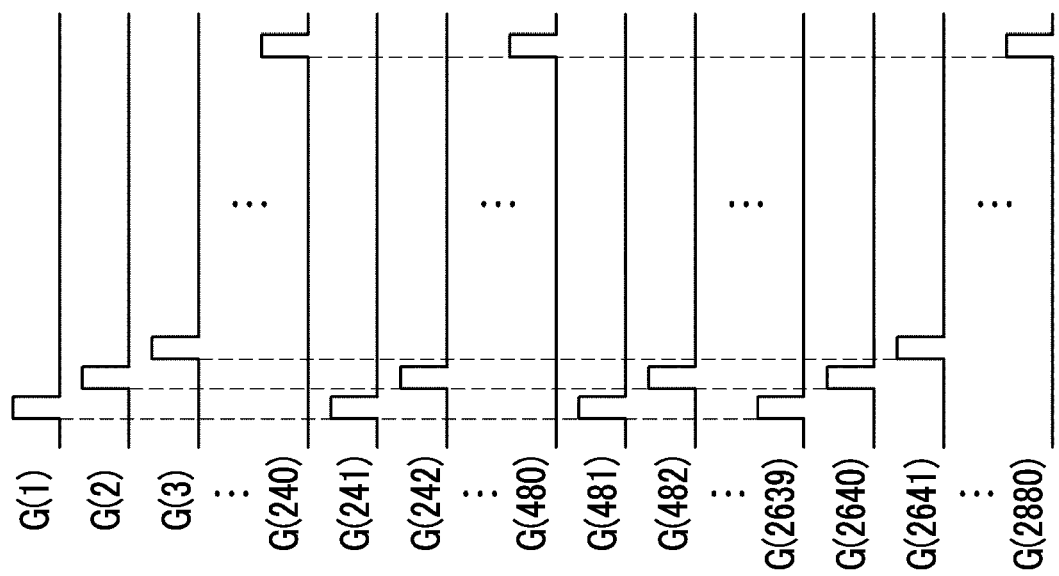
FIG. 13 is a diagram illustrating gate pulses in an AED operation.

As illustrated in FIG. 13, in the AED operation, the gate pulses G(R) are sequentially applied to the gate lines 41 corresponding to the same rows at the same time from the first row to the last row that each of the first to twelfth gate driving circuits 75 is in charge of. For example, the gate pulses G(1), G(241), G(481), . . . , G(2639) are applied to the gate lines 41 corresponding to the first row which is the first row of the first gate driving circuit 75, the 241st row which is the first row of the second gate driving circuit 75, the 481st row which is the first row of the third gate driving circuit 75, . . . , the 2639th row which is the first row of the twelfth gate driving circuit 75 at the same time. Then, the gate pulses G(2), G(242), G(482), . . . , G(2640) are applied to the gate lines 41 corresponding to the second, 242nd, 482nd, . . . , 2640th rows which are the rows following the first row at the same time.

As such, in the AED operation, the gate pulse G(R) is applied to the gate lines 41 corresponding to a total of 12 rows which are arranged at an interval of 240 rows. Therefore, the TFTs 44 in 12 rows are simultaneously turned on and charge from the pixels 40 in 12 rows is added in the signal line 42 corresponding to each column and is then input to the CA 60. Therefore, in a case in which the same charge is generated in each pixel 40, the dose signal DDS(C) obtained by the AED operation is approximately 12 times the image signal DIS(C) obtained by the image reading operation. As a result, it is possible to improve the signal-to-noise (S/N) ratio of the dose signal DDS(C).

Whenever the dose signal DDS(C) based on the charge corresponding to 12 rows is stored in the memory 52, the control unit 54 compares the dose signal DDS(C) with the irradiation start determination threshold value to determine whether the emission of X-rays has started. The dose signals DDS(C) corresponding to 2304 columns are output. The control unit 54 compares one representative value among 2304 dose signals with the irradiation start determination threshold value. The representative value is, for example, an average value, a maximum value, or a mode value of 2304 dose signals.

In the pixel charge accumulation operation, the gate driving circuit 75 does not apply the gate pulse G(R) to the gate line 41 and all of the TFTs 44 of the pixels 40 are in an off state.

In the pixel reset operation, the gate pulse G(R) may not be sequentially applied to each gate line 41 unlike FIG. 11 and the first to twelfth gate driving circuits 75 may sequentially apply the gate pulses G(R) to the corresponding first to last rows such that the gate pulse G(R) is applied to the gate lines 41 corresponding to the same rows at the same time, as illustrated in FIG. 13. Alternatively, the gate pulses G(R) is applied to each gate line 41 at the same time to collectively read charge from all of the pixels 40.

Figure 14:
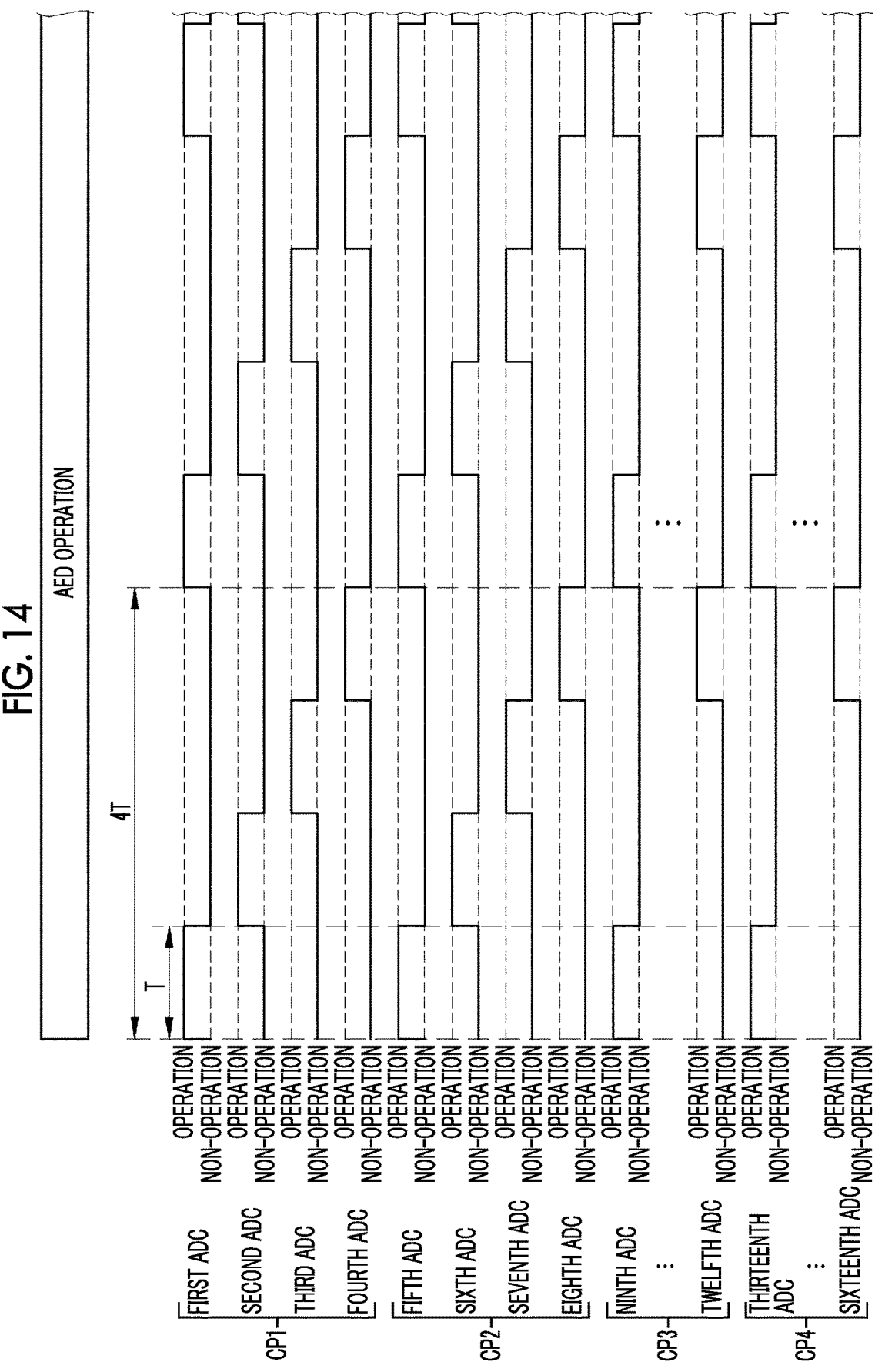
FIG. 14 is a diagram illustrating the power supply state of the ADC in the AED operation.

As illustrated in FIG. 14, the control unit 54 periodically switches the power supply state of the first to sixteenth ADCs 77, specifically, the operating state and the non-operating state during the AED operation. In addition, the control unit 54 shifts the switching timing of the power supply state of the first to sixteenth ADCs 77. Specifically, first, the control unit 54 changes the first, fifth, ninth, and thirteenth ADCs 77 which are the first ADCs in the chips CP1 to CP4 to the operating state and then switches the operating state to the non-operating state after the lapse of a time T. The control unit 54 changes the second, sixth, tenth, and fourteenth ADCs 77 adjacent to the above-mentioned ADCs to the operating state at the same time as the switching and similarly switches the operating state to the non-operating state after the lapse of the time T. Then, the control unit 54 operates the third, seventh, eleventh, and fifteenth ADCs 77 for the time T and then operates the fourth, eighth, twelfth, and sixteenth ADCs 77 which are the last ADCs in the chips CP1 to CP4 for the time T. Then, the control unit 54 repeats the series of power supply state switching operations.

Since the first to sixteenth ADCs 77 are provided for the areas AR1 to AR16, respectively, FIG. 14 illustrates a case in which the power supply state of the ADC 77 is switched in units of the ADCs 77 that are in charge of the areas AR. The first, fifth, ninth, and thirteenth ADCs 77, the second, sixth, tenth, and fourteenth ADCs 77, the third, seventh, eleventh, and fifteenth ADCs 77, and the fourth, eighth, twelfth, and sixteenth ADCs 77 correspond to groups in which the power supply state is switched at the same timing. In the groups, the timing of the power supply state is shifted. In addition, three ADCs 77 are disposed between two ADCs 77 belonging to the same group. For example, a total of three ADCs 77, that is, the second to fourth ADCs 77 are disposed between the first and fifth ADCs 77 forming the same group.

The time T is the time required to read the dose signals DDS(C) from all of 144 columns of the pixels 40 that each ADC 77 is in charge of in the AED operation. The time (hereinafter, referred to as a reading period of the dose signal DDS(C)) required to read the dose signal DDS(C) from all of 2304 columns is 4T (=T'4) since the dose signals DDS(C) are read four times by the chips CP1 to CP4.

The dose signal DDS(C) obtained by the AED operation is not used as the image information of the patient P unlike the image signal DIS(C) obtained by the image reading operation. Therefore, in the AED operation, as illustrated in FIG. 13, the gate pulse G(R) is applied to the gate lines 41 corresponding to a total of 12 rows at the same time and charge from the pixels 40 in 12 rows is added in the signal line 42 corresponding to each column. As illustrated in FIG. 14, in the AED operation, the first to sixteenth ADCs 77 are not always in the operating state unlike the image reading operation and the power supply state is periodically switched.

Figure 15:
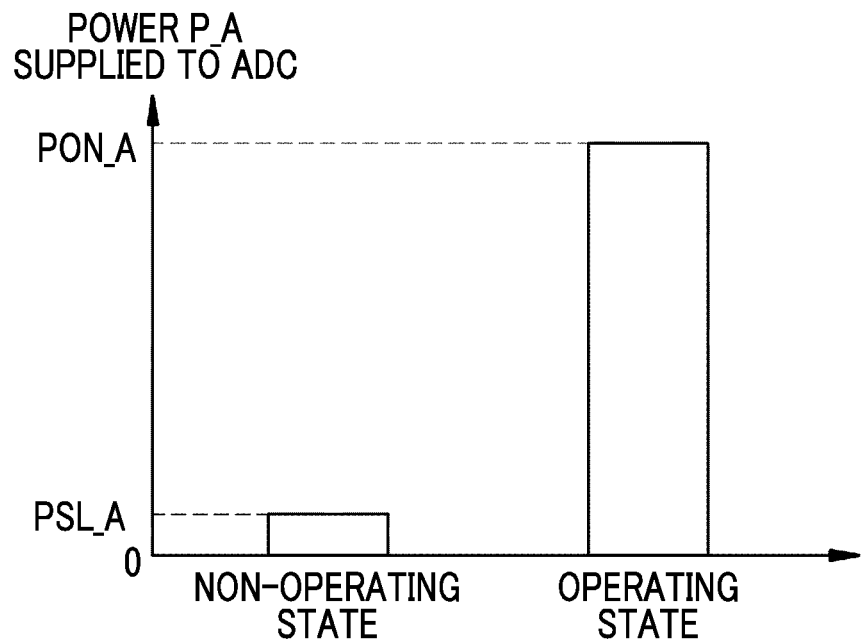
FIG. 15 is a graph illustrating the supply of power to the ADC.

Here, the operating state is a state in which power PON_A required to fulfill the function of the ADC 77 is supplied to the ADC 77 as illustrated on the right side in FIG. 15. The power PON_A corresponds to first power. That is, the operating state corresponds to the first state as described above. In contrast, the non-operating state is a state in which power PSL_A which is lower than the power PON_A and at which the ADC 77 is not capable of fulfilling its function is supplied to the ADC 77 as illustrated on the right side in FIG. 15. The power PSL_A corresponds to second power. That is, the non-operating state corresponds to the second state as described above.

As illustrated in FIGS. 12 and 14, the control unit 54 has a function of switching the power supply state to the ADC 77 between the operating state which is the first state and the non-operating state which is the second state.

Specifically, the power PON_A required to fulfill the function of the ADC 77 is power required for the image reading operation. In addition, the operating state may be a state in which power which is lower than the power required for the image reading operation and at which the ADC 77 can fulfill the function is supplied.

In FIG. 15, the power PSL_A has a value equal to or greater than 0. However, the power PSL_A may be 0. That is, the non-operating state may be a power-off state in which no power is supplied to the ADCs 77. In addition, the non-operating state may be a state in which the supply of a clock signal defining the operation timing of the ADC 77 is stopped such that the power consumption of the ADC 77 is substantially zero.

Figure 16:
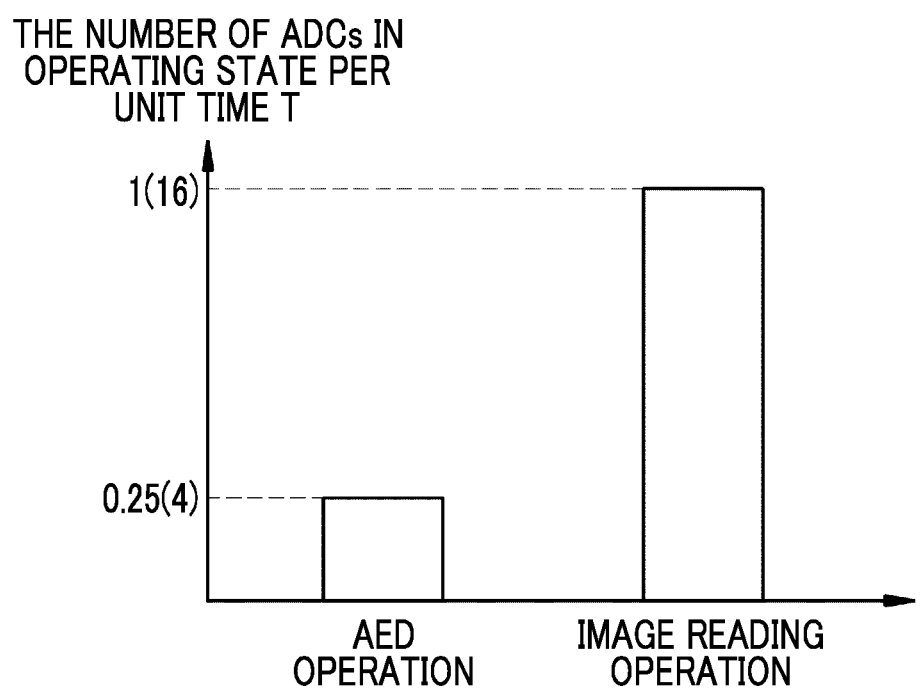
FIG. 16 is a graph illustrating the number of ADCs in a first state per unit time in the AED operation and the image reading operation.

As illustrated in FIG. 12, in the image reading operation, all of the first to sixteenth ADCs 77 are always in the operating state. Therefore, in a case in the unit time is T, the number of ADCs 77 in the operating state (first state) per unit time T is 16. In contrast, as illustrated in FIG. 14, in the AED operation, since four of the first to sixteenth ADCs 77 are operated at the same timing, the number of ADCs 77 in the operating state per unit time T is 4. Therefore, as illustrated in FIG. 16, in a case in which 16, which is the number of ADCs 77 per unit time T in the image reading operation, is normalized to 1, the number of ADCs 77 per unit time T in the AED operation is 0.25 (=4/16), which is less than that in the image reading operation.

The control unit 54 switches the power supply state of the CA 60, the CDS 61, and the MUX 76 that form the block BL together with the ADC 77 in operative association with the ADC 77, which is not illustrated and whose description will be omitted.

Figure 17:
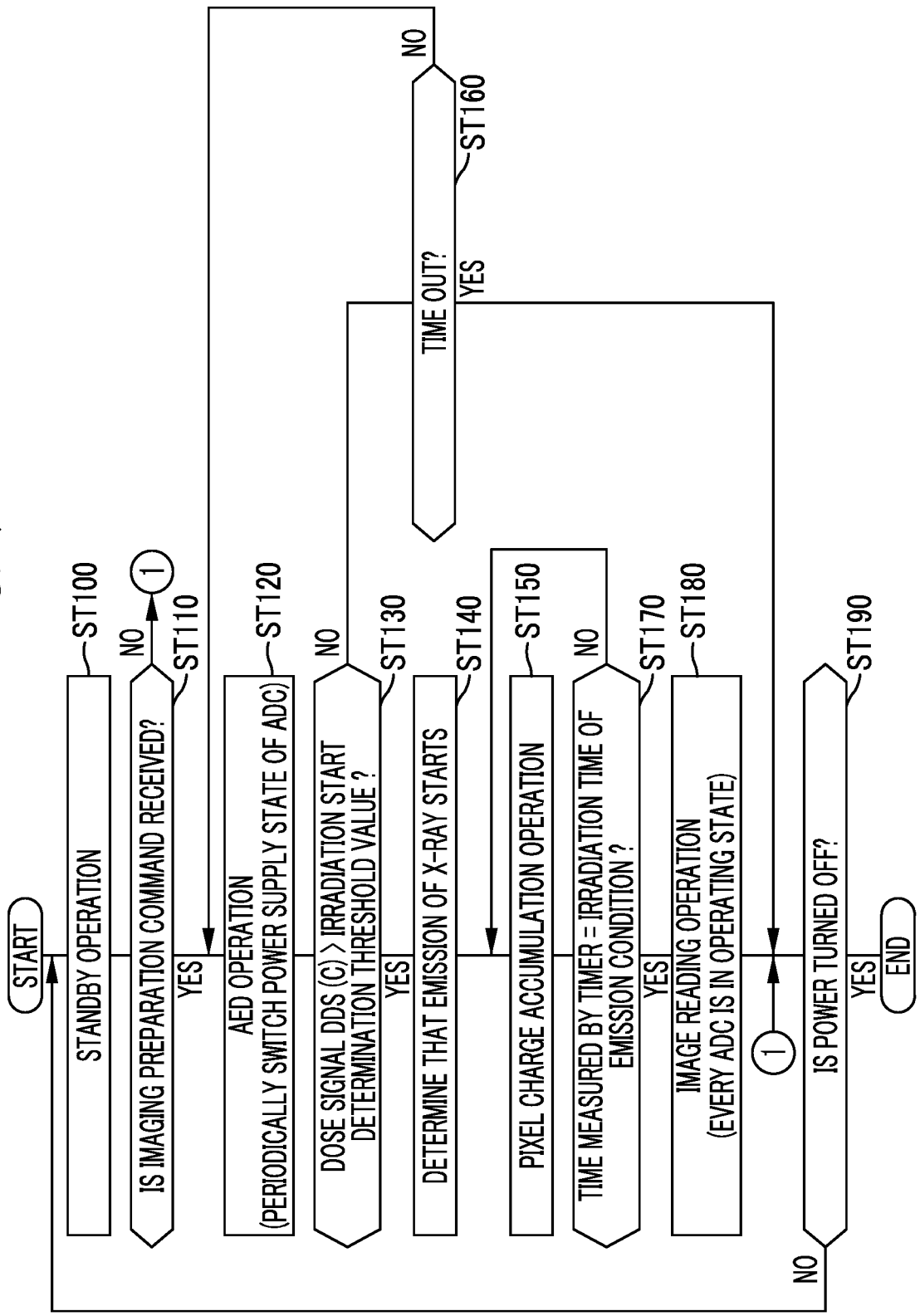
FIG. 17 is a flowchart illustrating the procedure of the operation of the electronic cassette.

Next, the operation of the configuration will be described with reference to a flowchart illustrated in FIG. 17. In a case in which the operator takes an X-ray image with the X-ray imaging system 10, the operator turns on the electronic cassette 16. The control unit 54 performs the standby operation (Step ST100).

The operator sets a desired imaging menu through the input device 21 of the console 17. Then, various kinds of information, such as the set imaging menu and the irradiation conditions corresponding to the set imaging menu, are transmitted as an imaging preparation command from the console 17 to the electronic cassette 16.

After setting the imaging menu, the operator sets the same irradiation conditions as the irradiation conditions corresponding to the set imaging menu or irradiation conditions obtained by finely adjusting the irradiation conditions corresponding to the set imaging menu according to, for example, the physique of the patient P in the radiation source control device 14. The operator sets the electronic cassette 16 in one of the upright imaging table 18 and the decubitus imaging table 19 and locates the X-ray source 13, the electronic cassette 16, and the patient P at desired positions. Then, the operator presses the irradiation switch 15 to drive the X-ray source 13 such that X-rays are emitted to the patient P. In addition, the order of the setting of the imaging menu, the setting of the irradiation conditions, and the positioning of, for example, the patient P may be reversed.

The imaging preparation command which is various kinds of information including the imaging menu is received by the wireless communication unit 22 or the wired communication unit 66 and is then received by the control unit 54 (YES in Step ST110). After receiving the imaging preparation command, the control unit 54 performs the AED operation. During the AED operation, as illustrated in FIG. 14, the power supply state of the first to sixteenth ADCs 77 is periodically switched (Step ST120, an irradiation start detection step).

The control unit 54 compares the dose signal DDS(C) obtained by the AED operation with the irradiation start determination threshold value (Step ST130). With the emission of X-rays, the value of the dose signal DDS(C) increases. In a case in which the dose signal DDS(C) is greater than the irradiation start determination threshold value (YES in Step ST130), the control unit 54 determines that the emission of X-rays has started (Step ST140). The control unit 54 performs the pixel charge accumulation operation (Step ST150). In a case in which the dose signal DDS(C) is not larger than the irradiation start determination threshold value within a predetermined time (YES in Step ST160) and power is not turned off (NO in Step ST190), the control unit 54 returns to the standby operation again (Step ST100).

In a case in which the control unit 54 detects the start of the emission of X-rays, the timer starts the measurement of time. Until the time measured by the timer reaches the irradiation time in the irradiation conditions set by the console 17, the pixel charge accumulation operation is continuously performed. In a case in which the time measured by the timer reaches the irradiation time in the irradiation conditions (YES in Step ST170), the control unit 54 performs the image reading operation. During the image reading operation, as illustrated in FIG. 12, all of the first to sixteenth ADCs 77 are always in the operating state (Step ST180, an image reading step). This series of operations is continuously performed until power is turned off (YES in Step ST190).

The image signal DIS(C) obtained by the image reading operation is transmitted as an X-ray image from the wireless communication unit 22 or the wired communication unit 66 to the console 17. The X-ray image is displayed on the display 20 such that the operator browses the X-ray image.

The number of ADCs 77 in the operating state per unit time T in the AED operation is less than that in the image reading operation by the switching of the power supply state of the first to sixteenth ADCs 77. Therefore, it is possible to reduce the power consumption of the signal processing circuit 51 in the AED operation.

In the related art, even in the AED operation, the first to sixteenth ADCs 77 are always in the operating state as in the image reading operation and the number of ADCs 77 in the operating state per unit time is equal to that in the image reading operation. Therefore, power consumption is significantly high in the AED operation whose operating time is longer than that of the image reading operation which ends in a case in which an X-ray image corresponding to one screen is read once. In particular, in the electronic cassette 16 driven by the battery 65, in a case in which power consumption is high, the battery 65 needs to be charged frequently. As a result, imaging efficiency is reduced.

However, in the first invention, it is possible to reduce the power consumption of the signal processing circuit 51 in the AED operation. Therefore, the battery 65 lasts longer than that in the related art. As a result, the number of times the battery 65 is charged is reduced. Thus, it is possible to improve imaging efficiency.

A method that performs control such that a specific ADC 77 is always in the non-operating state is considered as a method for reducing the number of operating ADCs 77 in the operating state per unit time T in the AED operation to be less than that in the image reading operation. However, in a case in which a specific ADC 77 is always in the non-operating state, the dose signal DDS(C) of the area AR that the specific ADC 77 is in charge of is not read. That is, there is an area AR that is not coverable by the AED operation.

In contrast, in this embodiment, as illustrated in FIG. 14, the power supply state of all of the first to sixteenth ADCs 77 is periodically switched to reduce the number of operating ADCs 77 in the operating state per unit time T in the AED operation so to be less than that in the image reading operation. Therefore, it is possible to obtain the effect of reading the dose signals DDS(C) from all of the areas AR1 to AR16 and covering all of the areas AR1 to AR16 in addition to the effect of reducing the power consumed of the signal processing circuit 51 in the AED operation.

A method that performs control such that a specific ADC 77 is always in the operating state and the other ADCs 77 are always in the non-operating state is considered as another method for reducing the number of operating ADCs 77 in the operating state per unit time T in the AED operation to be less than that in the image reading operation. However, in a case in which the power supply state is periodically switched as in the first to sixteenth ADCs 77 according to this embodiment, without performing control such that a specific ADC 77 is always in the operating state, it is clear that the power consumption of the signal processing circuit 51 can be further reduced.

As can be seen from the above, the periodical switching of the power supply state of at least one of a plurality of ADCs 77 in the AED operation is more effective than that in a case in which control is performed such that a specific ADC 77 is always in the non-operating state or a case in which control is performed such that a specific ADC 77 is always in the operating state and the other ADCs 77 are always in the non-operating state.

Since all of the ADCs 77 are changed to the operating state in the image reading operation, it is possible to obtain a high-quality X-ray image.

(1-2)-th Embodiment

Figure 18:
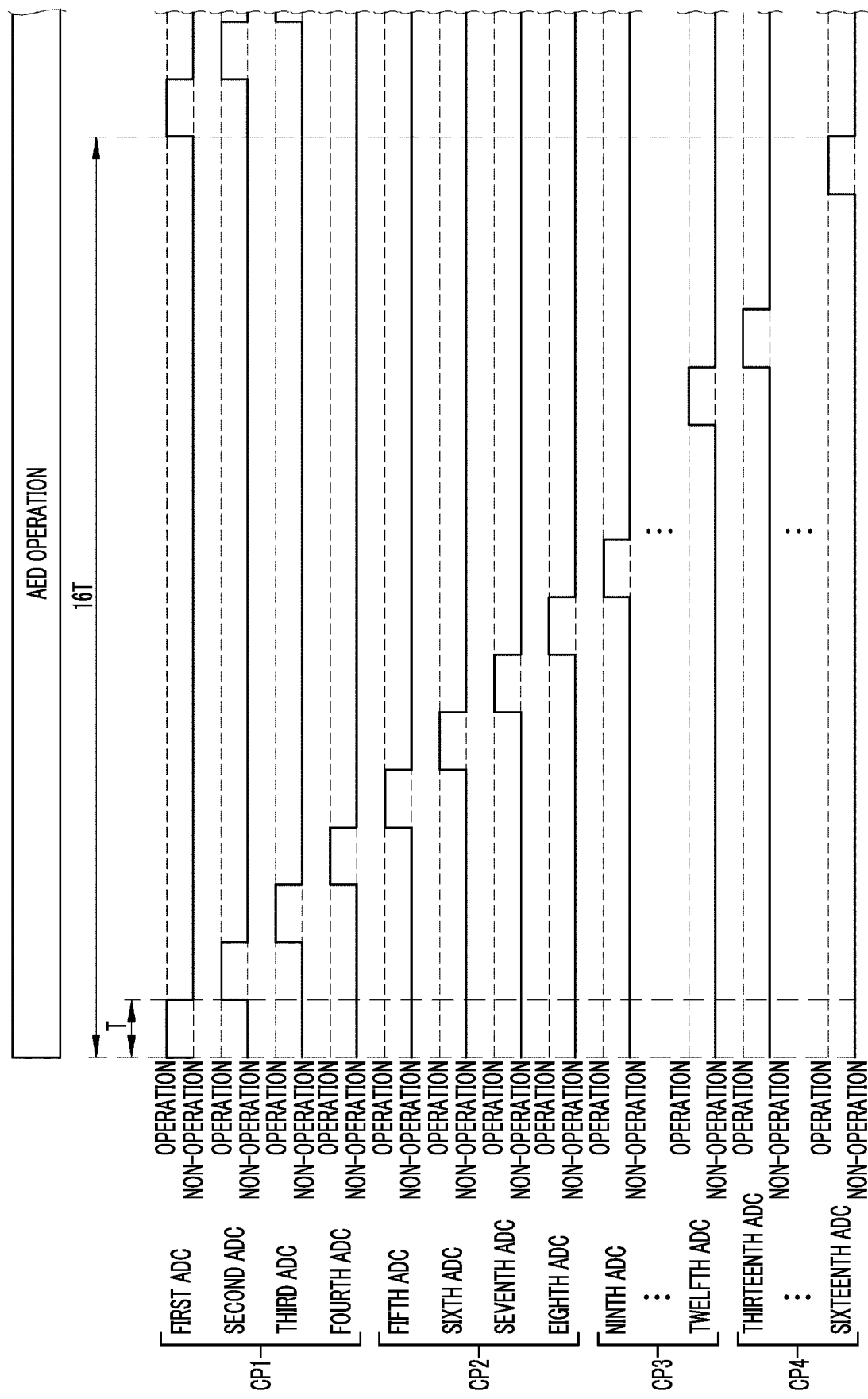
FIG. 18 is a diagram illustrating the power supply state of the ADC in the AED operation in a (1-2)-th embodiment.

In a (1-2)-th embodiment illustrated in FIG. 18, the control unit 54 shifts the switching timing of the power supply state of all of the first to sixteenth ADCs 77. That is, first, the control unit 54 operates the first ADC 77 for the time T. Then, the control unit 54 operates the second ADC 77 for the time T and operates the third ADC 77 for the time T. The control unit 54 continuously performs the switching of the power supply state up to the sixteenth ADC 77. After operating the sixteenth ADC 77 for the time T, the control unit 54 returns to the first ADC 77 and operates the first ADC 77 for the time T again. Then, the control unit 54 repeats the series of power supply state switching operations.

In this case, the reading period of the dose signal DDS(C) is 16T (=T'16) which is longer than 4T in the (1-1)-th embodiment. However, since the number of ADCs 77 in the operating state per unit time T is 1, the number of ADCs 77 per unit time T in the AED operation in a case in which 16 which is the number of ADCs 77 per unit time T in the image reading operation is normalized to 1 is 1/16=0.0625, which is less than 0.25 in the (1-1)-th embodiment.

(1-3)-th Embodiment

Figure 19:
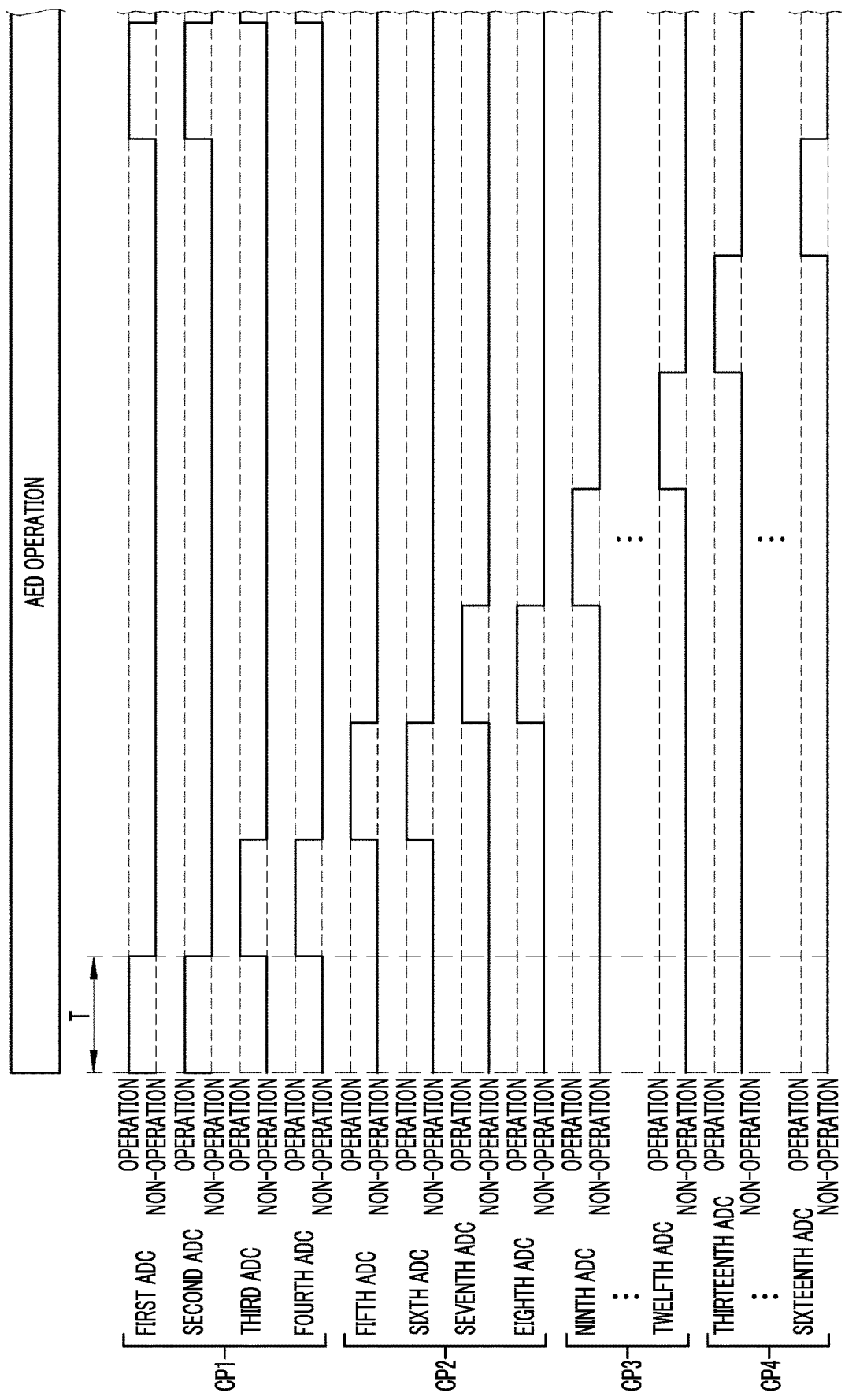
FIG. 19 is a diagram illustrating the power supply state of the ADC in the AED operation in a (1-3)-th embodiment.

FIG. 19 illustrates a (1-3)-th embodiment. In the (1-1)-th embodiment, the example in which three ADCs 77 are disposed between two ADCs 77 in the same group has been described. However, as in the (1-3)-th embodiment, there is no ADC 77 between two ADCs 77 in the same group. In other words, two ADCs 77 in the same group may be adjacent to each other.

In FIG. 19, each of the first and second ADCs 77, the third and fourth ADCs 77, the fifth and sixth ADCs 77, the seventh and eighth ADCs 77, . . . , the thirteenth and fourteenth ADCs 77, and the fifteenth and sixteenth ADCs 77 form a group in which the power supply state is switched at the same timing. However, there is no ADC 77 between two ADCs 77 belonging to the same group and the two ADCs 77 are adjacent to each other.

(1-4)-th Embodiment

Figure 20:
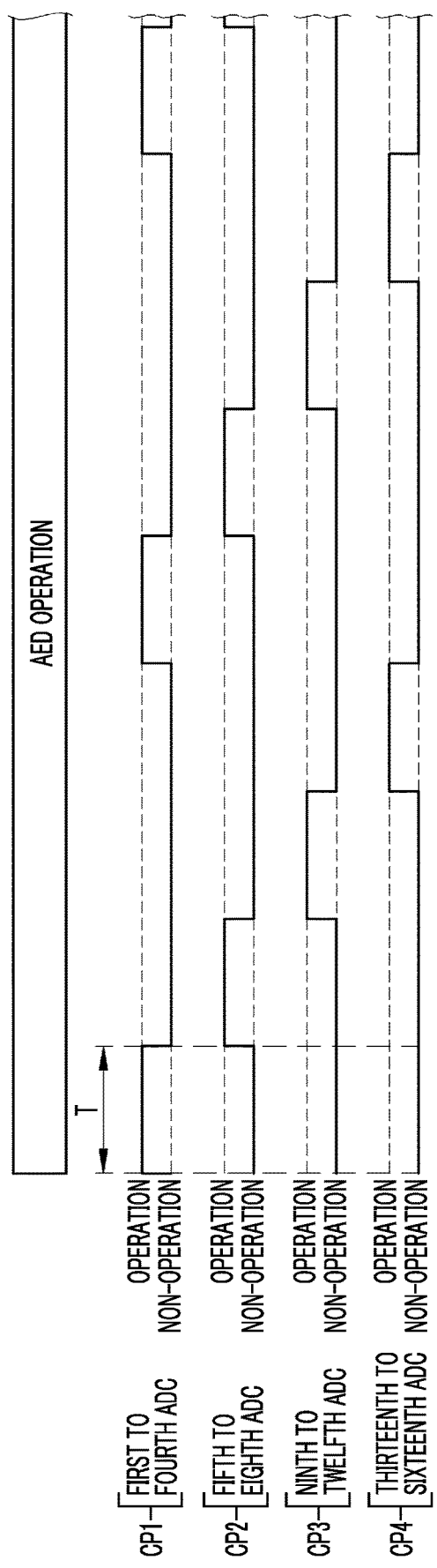
FIG. 20 is a diagram illustrating the power supply state of the ADC in the AED operation in a (1-4)-th embodiment.

FIG. 20 illustrates a (1-4)-th embodiment. In each of the above-described embodiments, the power supply state of the ADCs 77 is switched in units of the areas AR. However, as in the (1-4)-th embodiment, the control unit 54 may switch the power supply state of the ADCs 77 in units of the chips CP. Specifically, first, the control unit 54 changes the first to fourth ADCs 77 in the chip CP1 to the operating state and changes them to the non-operating state after the lapse of the time T. Then, similarly, the control unit 54 changes the fifth to eighth ADCs 77 in the chip CP2 to the operating state and changes them to the non-operating state after the lapse of the time T. Then, the control unit 54 operates the ninth to twelfth ADCs 77 in the chip CP3 for the time T and then operates the thirteenth to sixteenth ADCs 77 in the chip CP4 for the time T. Then, the control unit 54 repeats the series of power supply state switching operations.

As such, in a case in which the power supply state of the ADCs 77 is switched in units of the chips CP, control is simpler than that in a case in which the power supply state is switched in units of the areas AR. In addition, it is possible to respond to the chip CP without a function of switching the power supply state for each block BL.

(1-5)-th Embodiment

Figure 21:
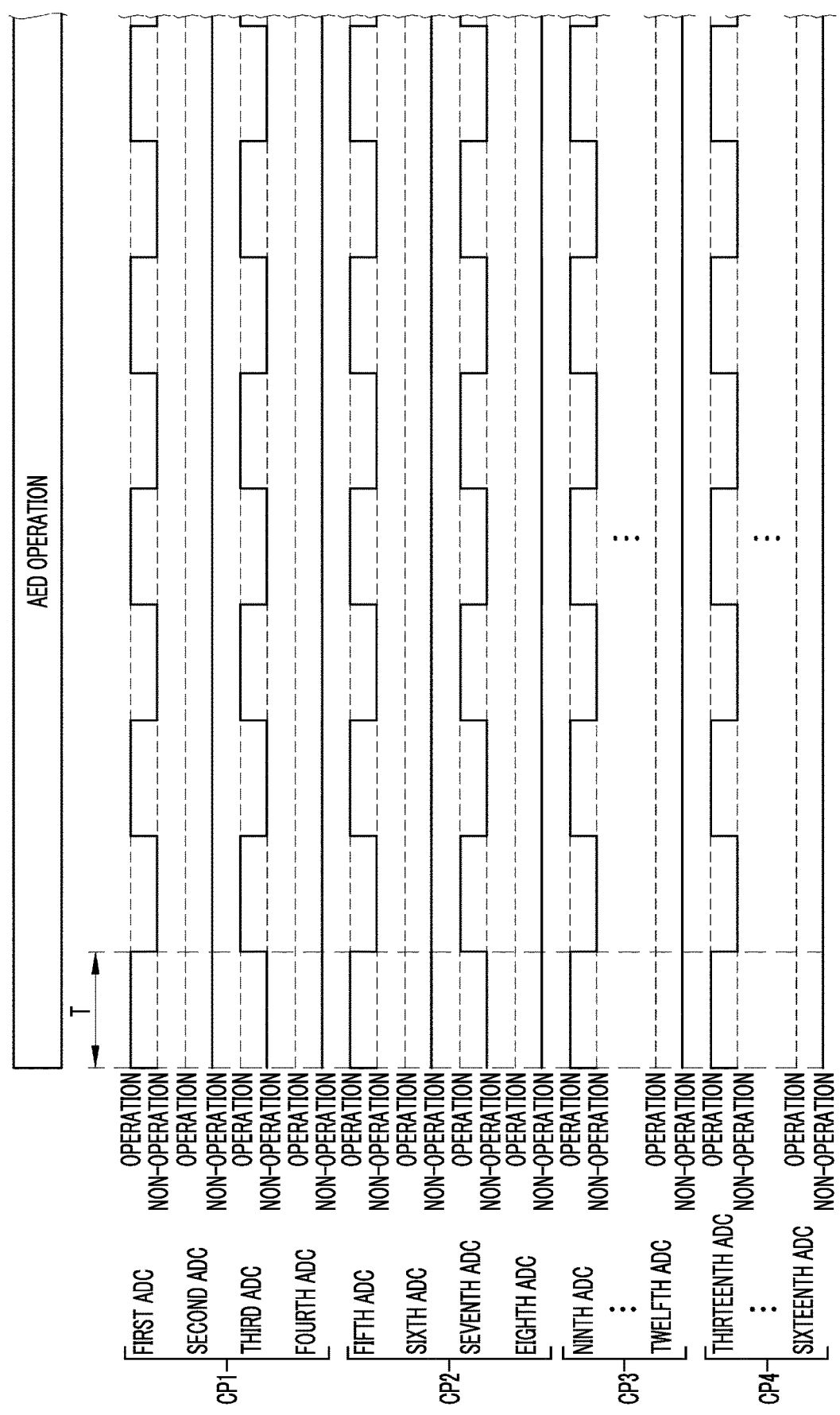
FIG. 21 is a diagram illustrating the power supply state of the ADC in the AED operation in a (1-5)-th embodiment.

FIG. 21 illustrates a (1-5)-th embodiment. In each of the above-described embodiments, the power supply state of all of the ADCs 77 is periodically switched. However, the invention is not limited thereto. As in the (1-5)-th embodiment, control may be performed such that at least one ADC 77 is always in the non-operating state.

As illustrated in FIG. 21, in the (1-5)-th embodiment, the control unit 54 performs control such that the even-numbered ADCs 77, such as the second, fourth, sixth, . . . , sixteenth ADCs 77, are always in the non-operating state during the AED operation. In contrast, the power supply state of the odd-numbered ADCs 77, such as the first, third, fifth, . . . , fifteenth ADCs 77, is periodically switched as in each of the above-described embodiments. As such, there may be an ADC 77 that is always in the non-operating state during the AED operation. In a case in which attention is focused on one ADC 77 and the ADC 77 is always in the non-operating state, power consumption can be lower than that in a case in which the power supply state is periodically switched.

Figure 27:
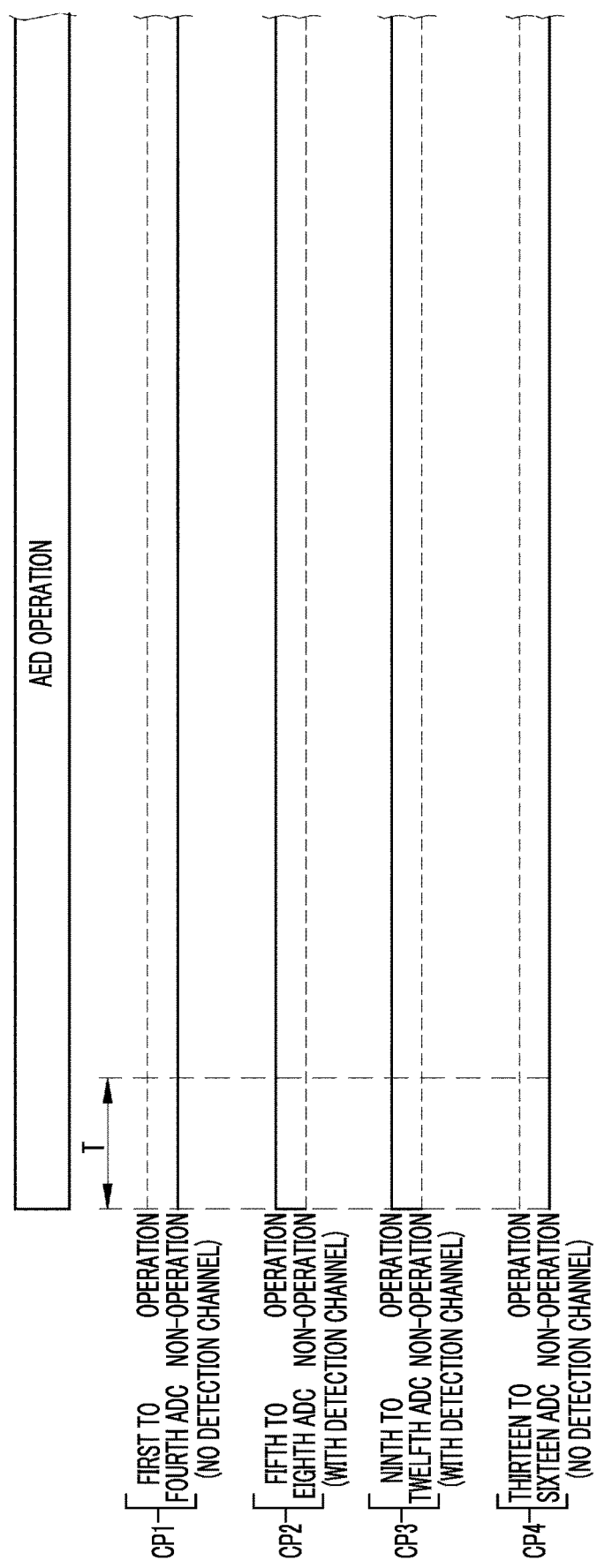
FIG. 27 is a diagram illustrating another example of the power supply state of the ADC in the AED operation in the (1-8)-th embodiment.

In contrast, there may be an ADC 77 that is always in the operating state during the AED operation as in the image reading operation (see FIG. 27). However, in this case, at least one ADC 77 that is in the non-operating state during the AED operation is required regardless of whether the power supply state is periodically switched or is fixed. The reason is as follows. In a case in which all of the ADCs 77 are always in the operating state, they are in the same state as that in the image reading operation and the number of ADCs 77 in the operating state per unit time in the AED operation is not less than that in the image reading operation.

(1-6)-th Embodiment

Figure 22:
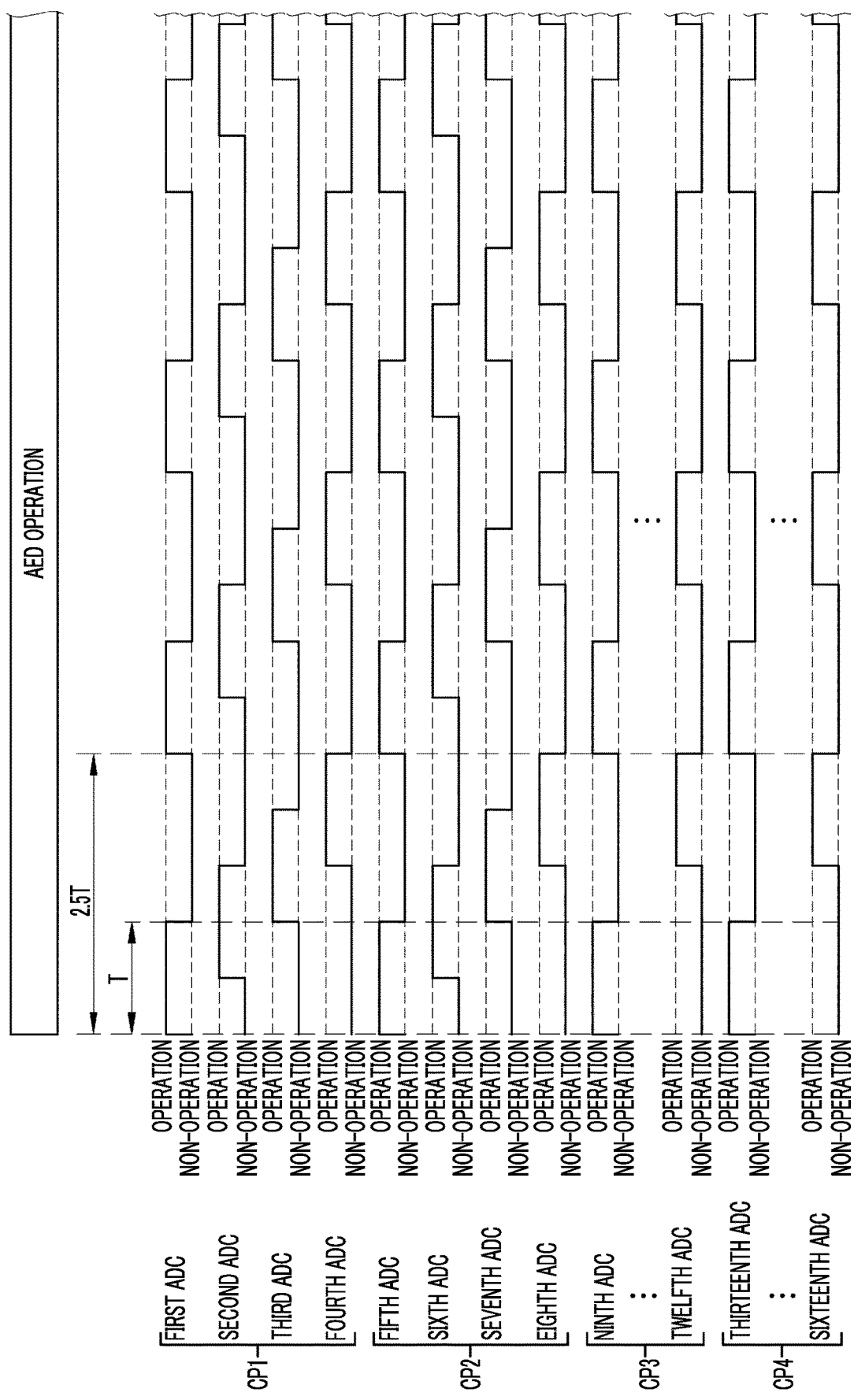
FIG. 22 is a diagram illustrating the power supply state of the ADC in the AED operation in a (1-6)-th embodiment.
Figure 23:
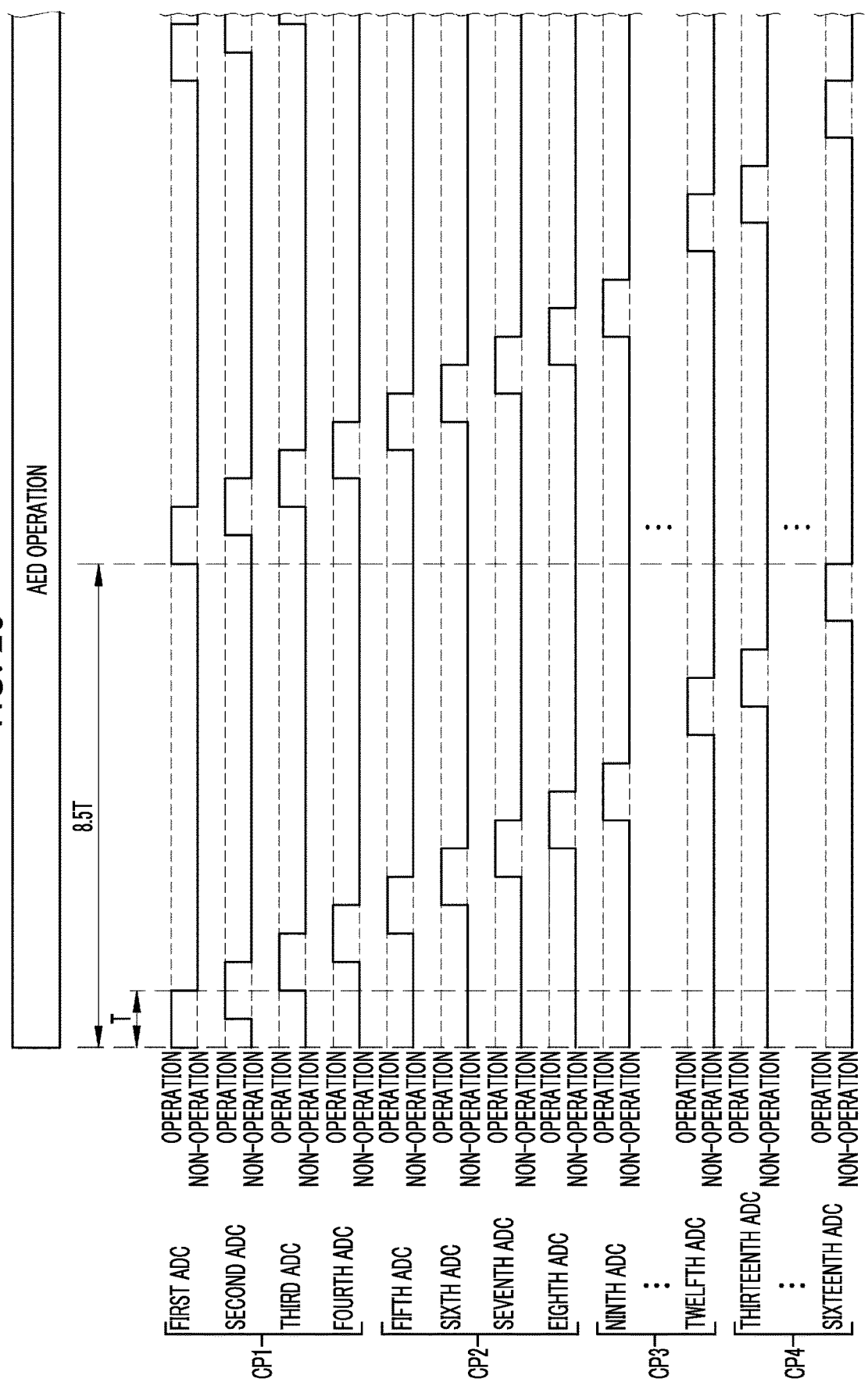
FIG. 23 is a diagram illustrating another example of the power supply state of the ADC in the AED operation in the (1-6)-th embodiment.

FIGS. 22 and 23 illustrate a (1-6)-th embodiment. In each of the above-described embodiments, for example, as the first, fifth, ninth, and thirteenth ADCs 77 and the second, sixth, tenth, and fourteenth ADCs 77 in the (1-1)-th embodiment illustrated in FIG. 14, at the timing when one ADC 77 is switched from the operating state to the non-operating state, the other ADC 77 is switched from the non-operating state to the operating state. However, the invention is not limited thereto. As in the (1-6)-th embodiment, the timing when one ADC 77 is switched from the operating state to the non-operating state may deviate from the timing when the other ADC 77 is switched from the non-operating state to the operating state.

The (1-6)-th embodiment illustrated in FIG. 22 is the same as the (1-1)-th embodiment illustrated in FIG. 14 in that the first, fifth, ninth, and thirteenth ADCs 77, the second, sixth, tenth, and fourteenth ADCs 77, the third, seventh, eleventh, and fifteenth ADCs 77, and the fourth, eighth, twelfth, and sixteenth ADCs 77 form groups in which the power supply state is switched at the same timing. However, before one ADC 77 is switched from the operating state to the non-operating state, another ADC 77 is switched from the non-operating state to the operating state. For example, while the first, fifth, ninth, and thirteenth ADCs 77 are in the operating state, the second, sixth, tenth, and fourteenth ADCs 77 are switched to the operating state, specifically, at a timing T/2.

As such, since the timing when one ADC 77 is switched from the operating state to the non-operating state deviates from the timing when the other ADC 77 is switched from the non-operating state to the operating state, it is possible to reduce the reading period of the dose signal DDS(C). Specifically, while the reading period of the dose signal DDS(C) is 4T in the (1-1)-th embodiment, the reading period is 2.5T in FIG. 22. Therefore, the reading period is reduced in this embodiment.

In this case, the number of ADCs 77 in the operating state per unit time T is 6 (=4+(4' 0.5)) since four ADCs 77 are in the operating state for the time T and four ADCs 77 in the operating state for the time T/2.

FIG. 22 illustrates an example based on the (1-1)-th embodiment illustrated in FIG. 14. FIG. 23 illustrates an example based on the (1-2)-th embodiment illustrated in FIG. 18, in which the switching timings of the power supply state of all of first to sixteenth ADCs 77 deviate from each other. In this case, similarly to the case illustrated in FIG. 22, before one ADC 77 is switched from the operating state to the non-operating state, the other ADC 77 is switched from the non-operating state to the operating state. For example, while the first ADC 77 is in the operating state, the second ADC 77 is switched to the operating state, specifically, at a timing T/2. In this case, it is also possible to reduce the reading period of the dose signal DDS(C) from 16T illustrated in FIGS. 18 to 8.5T. In this case, the number of ADCs 77 in the operating state per unit time T is 1.5.

(1-7)-th Embodiment

Figure 24:
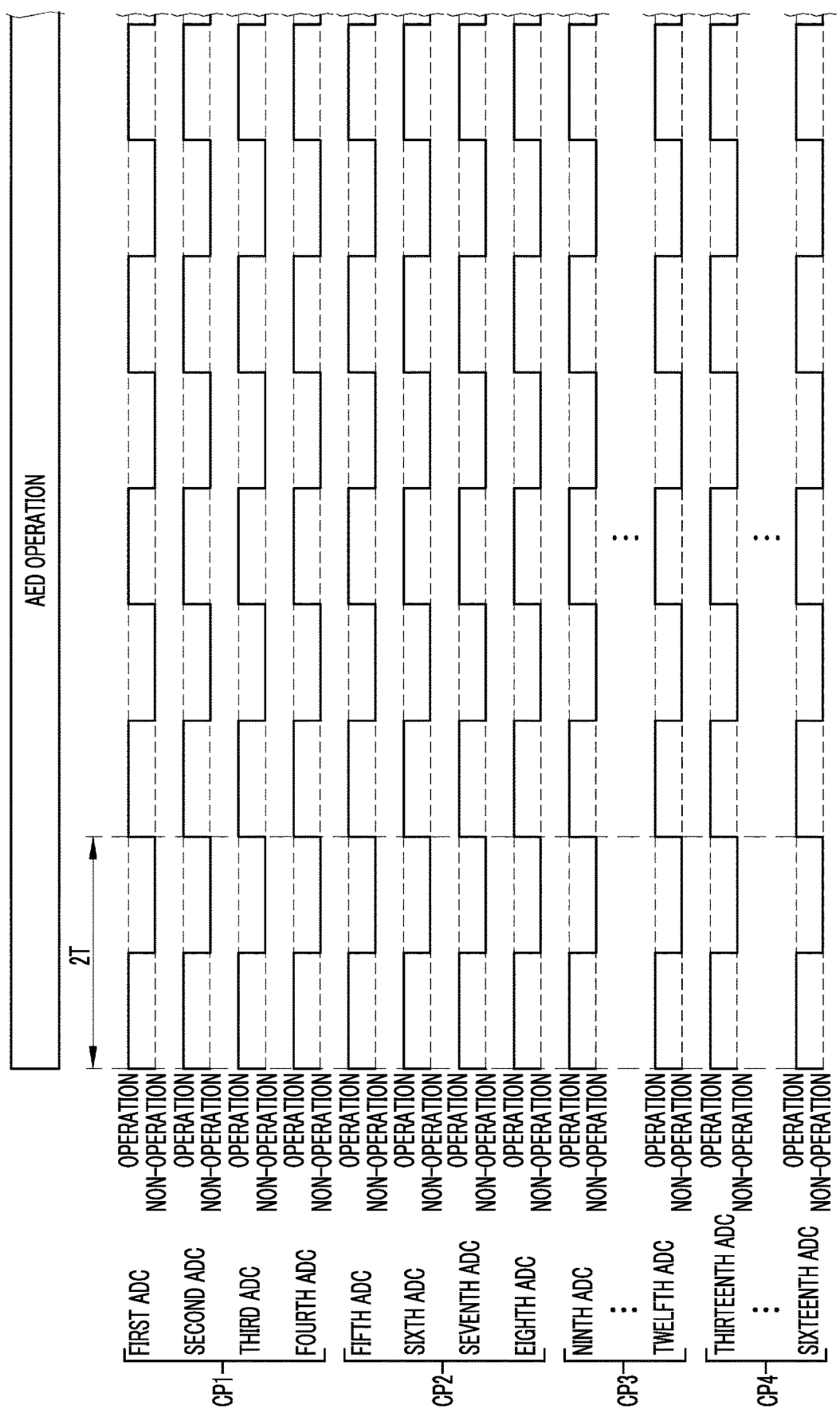
FIG. 24 is a diagram illustrating the power supply state of the ADC in the AED operation in a (1-7)-th embodiment.

FIG. 24 illustrates a (1-7)-th embodiment. In each of the above-described embodiments, the switching timings of the power supply state of a plurality of ADCs 77 deviate from each other. However, in the (1-7)-th embodiment, the control unit 54 matches the switching timings of the power supply state of all of the first to sixteenth ADCs 77.

In this case, the reading period of the dose signal DDS(C) is 2T which is obtained by adding the first half time T for which all of the ADCs 77 are in the operating state and the second half time T for which all of the ADCs 77 are in the non-operating state. In this case, the unit time is not T, but is 2T. The number of ADCs 77 in the operating state per unit time 2T is 8 (=16/2) since all of 16 ADCs 77 are in the operating state for the first time T and no ADCs 77 are in the operating state for the next time T.

(1-8)-th Embodiment

Figure 25:
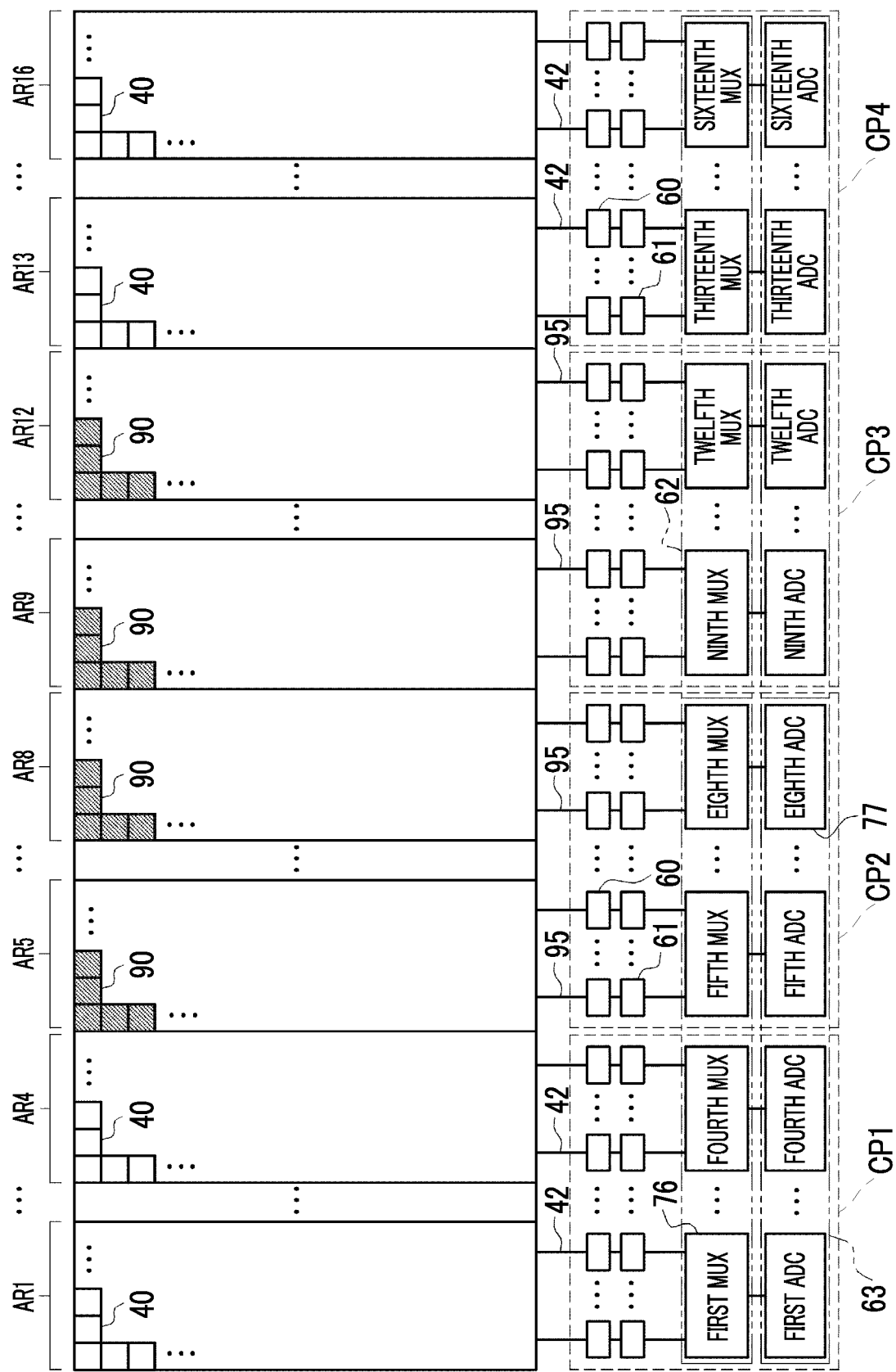
FIG. 25 is a block diagram illustrating a (1-8)-th embodiment in which a detection channel that is a signal line connected to a detection pixel used for the AED operation is set.
Figure 26:
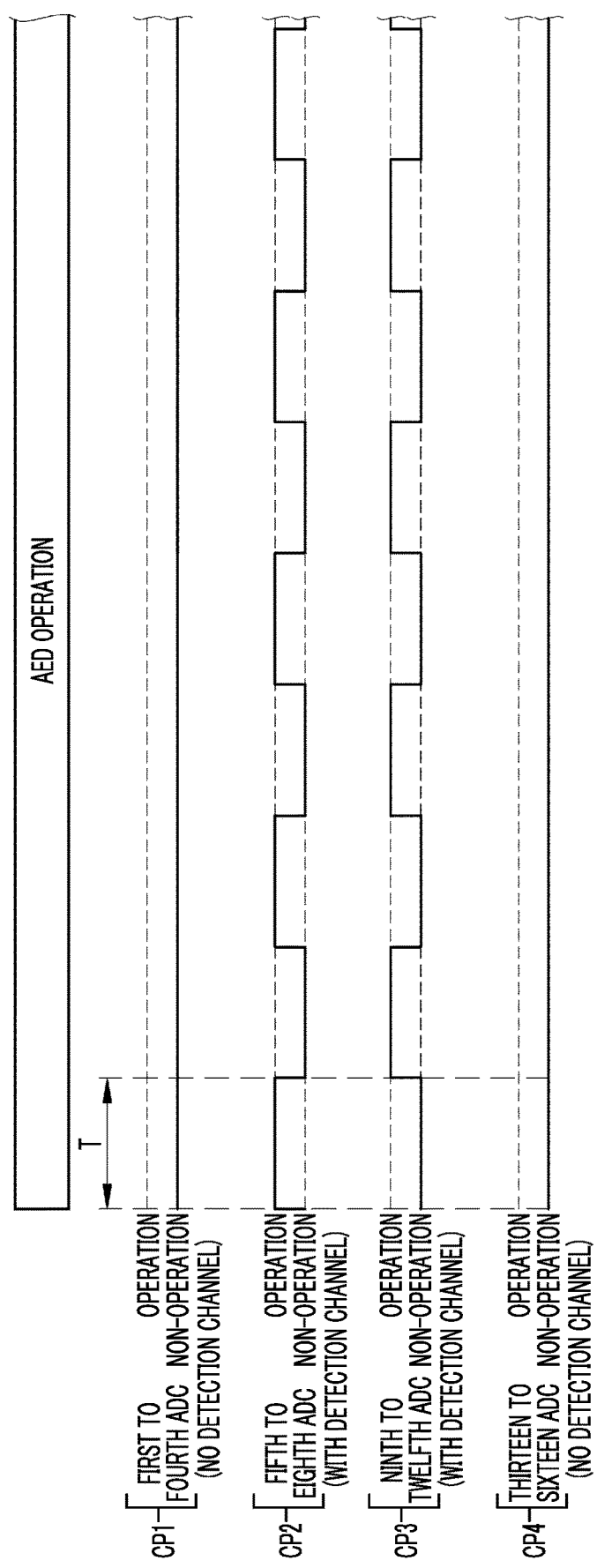
FIG. 26 is a diagram illustrating the power supply state of the ADC in the AED operation in the (1-8)-th embodiment.

FIGS. 25 to 27 illustrate a (1-8)-th embodiment. In each of the above-described embodiments, in the AED operation, the dose signals DDS(C) based on the charge from all of the pixels 40 are read. That is, all of the pixels 40 function as detection pixels for reading the dose signals DDS(C). However, instead of all of the pixels 40, some of a plurality of pixels 40 may be preset as the detection pixels. Hereinafter, a reference numeral is assigned to the detection pixel and the detection pixel is referred to as a detection pixel 90 (see FIG. 25). Hereinafter, the signal line 42 to which the detection pixel 90 is connected is referred to as a detection channel 95 (see FIG. 25).

FIG. 25 illustrates an example in which all of the pixels 40 belonging to a total of eight areas AR from the area AR5 to the area AR12 that are covered by the chips CP2 and CP3 among the chips CP1 to CP4 are set as the detection pixels 90 (which are hatched). In this case, the detection channels 95 are the signal lines 42 which are connected to the fifth to eighth MUXs 76 in the chip CP2 and the ninth to twelfth MUXs 76 in the chip CP3.

For example, as illustrated in FIG. 26, during the AED operation, the control unit 54 performs control such that the first to fourth ADCs 77 of the chip CP1 and the thirteenth to sixteenth ADCs 77 of the chip CP4 which are not in charge of the detection channels 95 are always in the non-operating state. In addition, the control unit 54 periodically switches the power supply state of the fifth to eighth ADCs 77 of the chip CP2 and the ninth to twelfth ADCs 77 of the chip CP3 which are in charge of the detection channels 95.

In a case in which the detection channel 95 is set, the ADC 77 which is not in charge of the detection channel 95 is meaningless even though it is in the operating state in the AED operation. Therefore, the ADC 77 is always in the non-operating state during the AED operation. On the other hand, the power supply state of the ADC 77 which is in charge of the detection channel 95 is periodically switched during the AED operation. The number of ADCs 77 in the operating state per unit time T is reduced by the above-mentioned configuration.

FIG. 27 is the same as FIG. 26 in that the ADC 77 which is not in charge of the detection channel 95 is always in the non-operating state during the AED operation. However, in FIG. 27, the ADCs 77 (the fifth to eighth ADCs 77 of the chip CP2 and the ninth to twelfth ADCs 77 of the chip CP3) which are in charge of the detection channels 95 are always in the operating state. As can be seen from the example illustrated in FIG. 27, the first invention includes a case in which the power supply state of the ADC 77 is not periodically switched.

In FIG. 25, all of the signal lines 42 in the areas AR5 to AR12 are set as the detection channels 95. However, the detection channels 95 may be set by any method. For example, four consecutive detection channels 95 may be set at intervals of 64 columns such that the first to fourth columns, the 65th to 68th columns, and the 129th to 132nd columns are set as the detection channels 95. In addition, the detection pixels 90 may be set in one detection channel 95 by any method. For example, all of the pixels 40 corresponding to one column may not be set as the detection pixels 90, but only the pixels 40 corresponding to the 481st to 960th rows that the third and fourth gate driving circuits 75 are in charge of may be set as the detection pixels 90.

(1-9)-th Embodiment

FIGS. 28 to 31 illustrate a (1-9)-th embodiment. In each of the above-described embodiments, the pixel 40 for obtaining the image signal DIS(C) in the image reading operation is also used as the detection pixel 90 for obtaining the dose signal DDS(C) in the AED operation. However, the invention is not limited thereto. A dedicated detection pixel 90X specialized for the AED operation may be provided separately from the pixel 40 for detecting an X-ray image.

Figure 28:
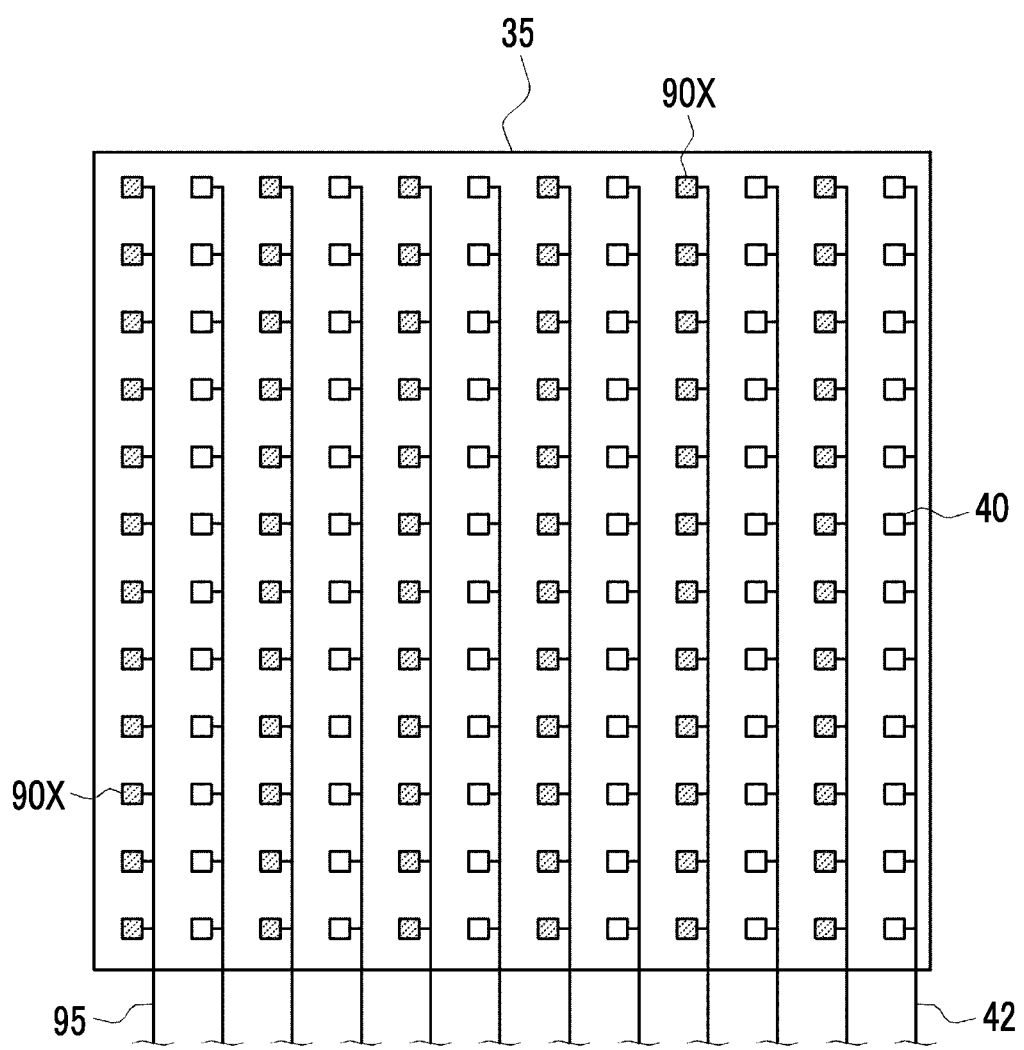
FIG. 28 is a diagram illustrating an example of the arrangement of the detection pixels.

In a case in which the detection pixel 90X used only for the AED operation is provided, the pixels 40 and the detection pixels 90X are mixed on the light detection substrate 35. The light detection substrate 35 is limited in size. Therefore, in a case in which an excessively large number of detection pixels 90X are provided, a space for the pixels 40 is reduced and the quality of the X-ray image is degraded. In addition, the following is considered: in a case in which the detection pixels 90X are provided so as to be concentrated on a region on the light detection substrate 35, the region is not irradiated with X-rays depending on the setting of the irradiation field. Therefore, for example, as illustrated in FIG. 28, it is preferable that several tens to several hundreds of detection pixels 90X are provided with respect to several millions of pixels 40 and the detection pixels 90X are dispersively provided on the light detection substrate 35. For example, the number of detection pixels 90X provided in one detection channel 95 is 12 among 2880 pixels.

Figure 29:
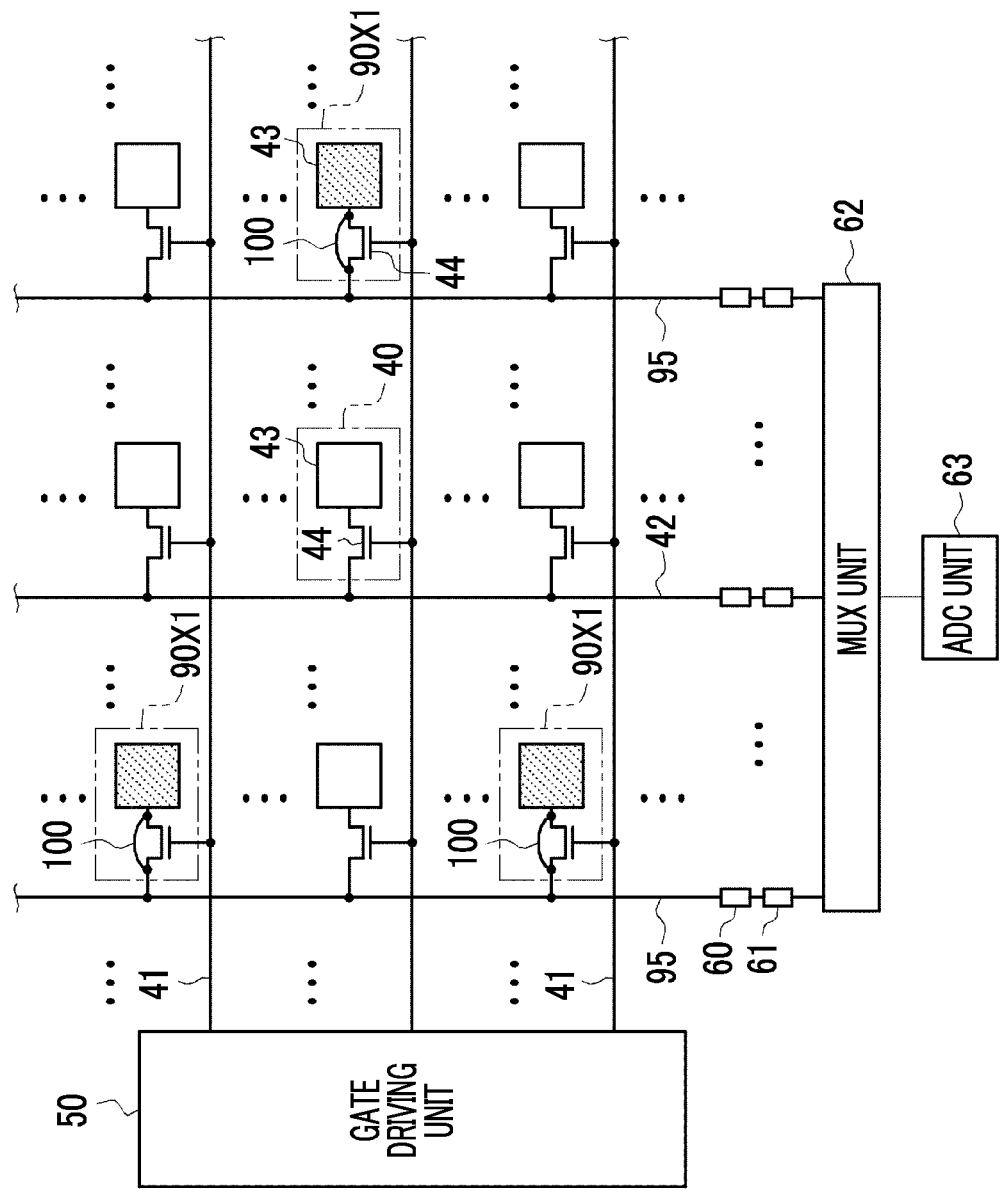
FIG. 29 is a block diagram illustrating an example of the detection pixel used for only the AED operation.

A detection pixel 90X1 illustrated in FIG. 29 has the same basic configuration comprising the photoelectric conversion unit 43 and the TFT 44 as the pixel 40. Therefore, the detection pixel 90X1 can be formed by almost the same manufacturing process as the pixel 40. The detection pixel 90X1 is different from the pixel 40 in that the source electrode and the drain electrode of the TFT 44 are short-circuited by a short-circuit line 100. That is, in the detection pixel 90X1 illustrated in FIG. 29, the photoelectric conversion unit 43 is directly connected to the signal line 42 by the short-circuit line 100. The signal line 42 becomes the detection channel 95.

In the detection channel 95, the charge generated in the photoelectric conversion unit 43 of the detection pixel 90X1 flows out regardless of the on/off state of the TFT 44. Therefore, for example, even in a case in which the TFTs 44 of the pixels 40 in the same row are turned off and the pixels 40 are in the pixel charge accumulation operation, the charge generated in the photoelectric conversion unit 43 of the detection pixel 90X1 always flows into the CA 60 through the detection channel 95.

In this case, similarly to the (1-8)-th embodiment illustrated in FIGS. 25 to 27, the ADC 77 that is not in charge of the detection channel 95 is always in the non-operating state during the AED operation. In addition, the power supply state of the ADC 77 that is in charge of the detection channel 95 is periodically switched or the ADC 77 is always in the operating state during the AED operation.

Figure 30:
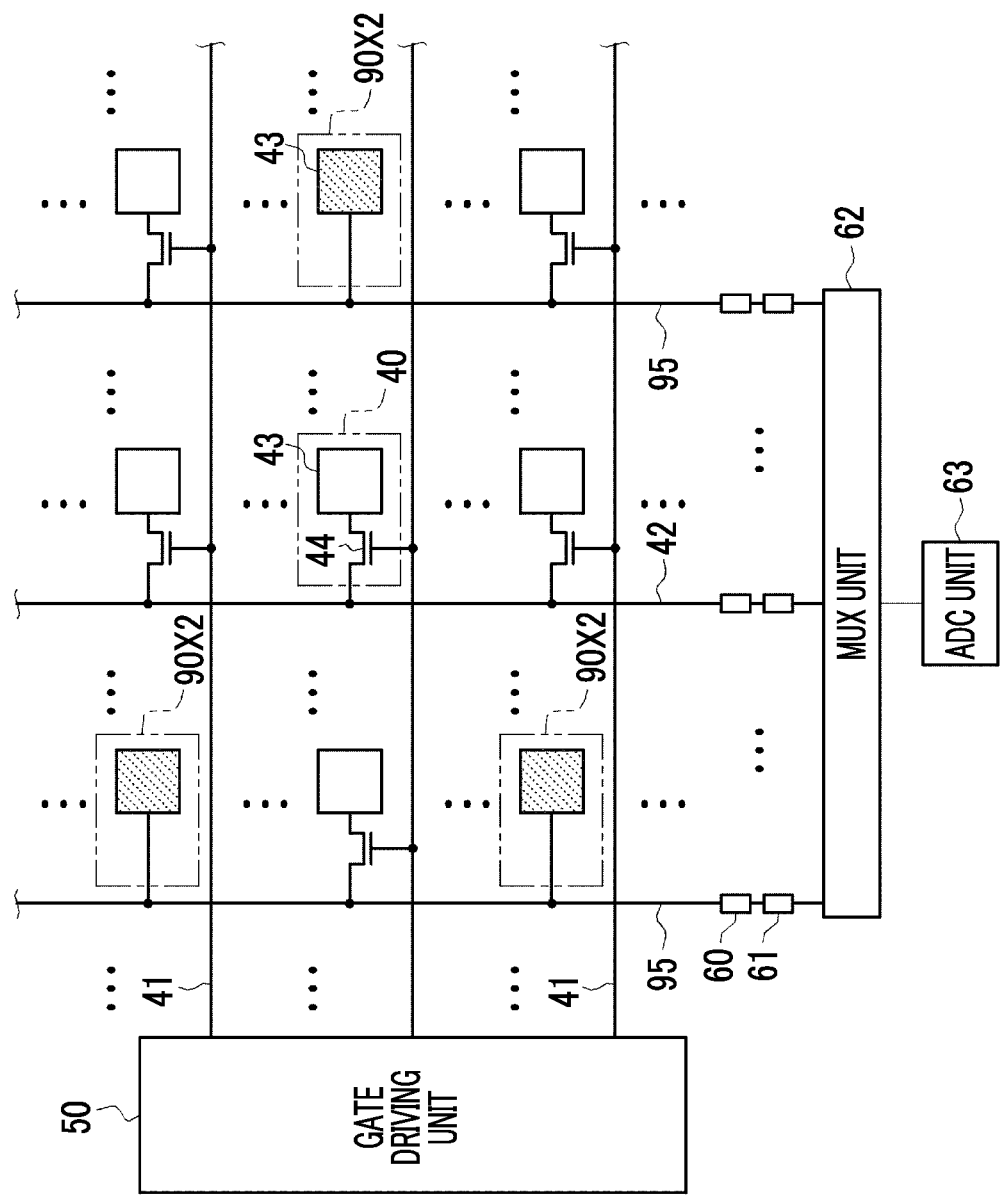
FIG. 30 is a block diagram illustrating another example of the detection pixel used for only the AED operation.

As a short-circuited pixel in which the photoelectric conversion unit 43 is directly connected to the signal line 42, a detection pixel 90X2 illustrated in FIG. 30 which does not include the TFT 44 and includes only the photoelectric conversion unit 43 may be used instead of the detection pixel 90X1 illustrated in FIG. 29. In the examples illustrated in FIGS. 29 and 30, the charge generated in the detection pixel 90X1 or 90X2 is always added to the charge generated in the pixel 40 in the same column as the detection pixel 90X1 or 90X2 which is a short-circuited pixel. As a result, it is difficult to use the pixel 40 in the same column as the detection pixel 90X1 or 90X2 as a pixel for acquiring the image signal DIS(C). Therefore, the pixel 40 and the detection pixel 90X1 or 90X2 in the column corresponding to the detection channel 95 are treated as defective pixels and are interpolated by the image signals DIS(C) of the pixels 40 in the neighboring column that is not the detection channel 95.

Figure 31:
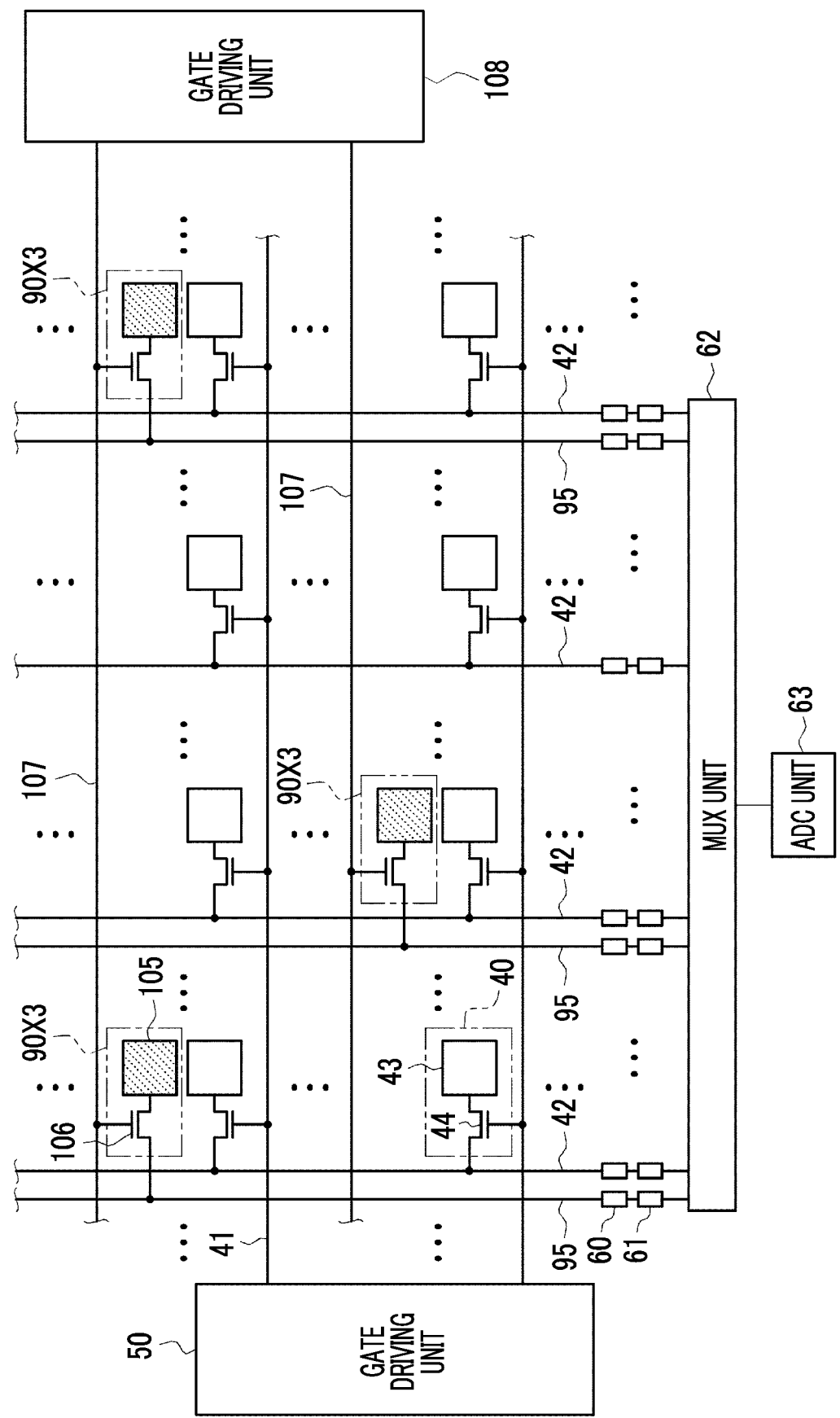
FIG. 31 is a block diagram illustrating still another example of the detection pixel used for only the AED operation.

FIG. 31 illustrates an example in which a detection pixel 90X3 used only for the AED operation is provided adjacent to a specific pixel 40. The detection pixel 90X3 comprises a photoelectric conversion unit 105 and a TFT 106 similarly to the pixel 40. A gate line 107 and a signal line (detection channel 95) different from the gate line 41 and the signal line 42 connected to the TFT 44 of the pixel 40 are connected to the TFT 106. The gate line 107 is connected to a gate driving unit 108 that performs driving independently of the gate driving unit 50. The detection channel 95 is connected to the MUX unit 62 together with the signal line 42.

During the AED operation, the gate driving unit 50 does not operate and only the gate driving unit 108 operates. As in the (1-1)-th embodiment, the gate driving unit 108 applies the gate pulses to the gate lines 107 corresponding to a plurality of rows at the same time to turn on the TFTs 106 connected to each gate line 107 in units of a plurality of rows. Alternatively, the gate driving unit 108 may sequentially apply the gate pulses to each gate line 107.

In this case, similarly to the (1-8)-th embodiment illustrated in FIGS. 25 to 27, the ADC 77 that is not in charge of the detection channel 95 is always in the non-operating state during the AED operation. In addition, the power supply state of the ADC 77 that is in charge of the detection channel 95 is periodically switched or the ADC 77 is always in the operating state during the AED operation. The MUX unit 62 has the same basic configuration as that in each of the above-described embodiments except that it is connected not only to the signal line 42 but also to the detection channel 95 connected to the detection pixel 90X3. In addition, the detection channel 95 different from the signal line 42 may not be provided only for the detection pixel 90X3. The TFT 106 of the detection pixel 90X3 may be connected to the signal line 42 such that the signal line 42 is also used as the detection channel 95.

In the case of FIG. 31, the pixel 40 and the detection pixel 90X3 can be driven independently by the gate driving units 50 and 108 and the signal line 42 and the detection channel 95 are separately provided. Therefore, as in FIGS. 29 and 30, the pixel 40 in the same column as the detection pixel 90X3 may not be treated as the defective pixel.

(1-10)-th Embodiment

Figure 32:
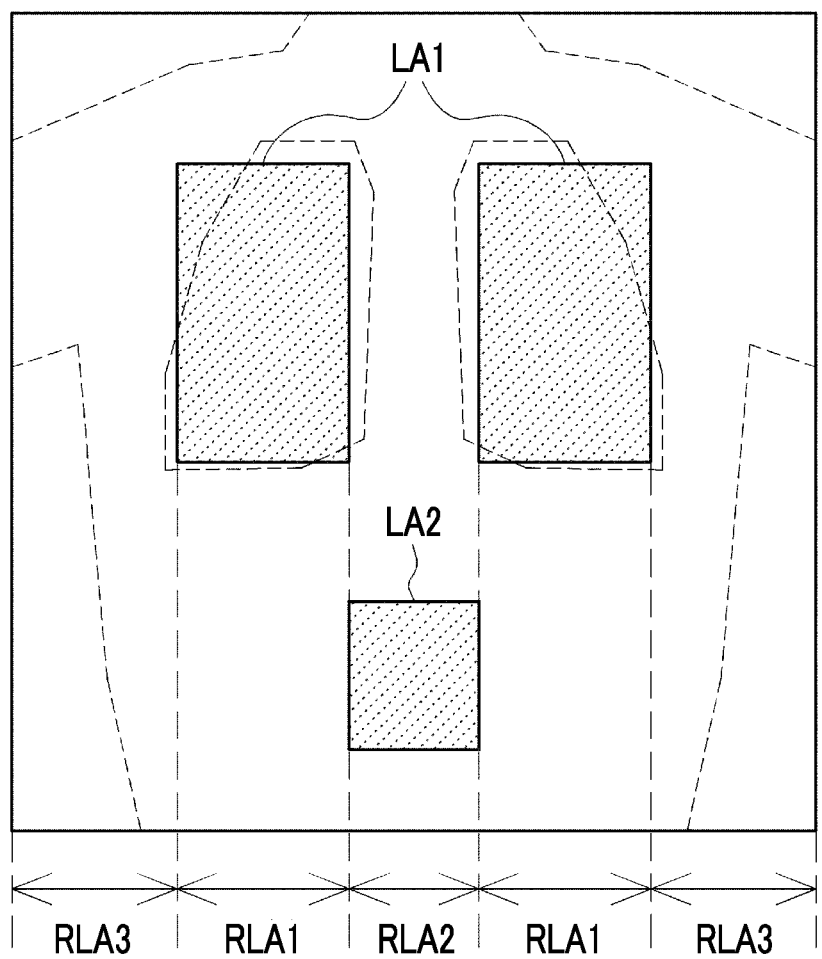
FIG. 32 is a diagram illustrating an example of the setting of the detection pixel.

FIG. 32 illustrates a (1-10)-th embodiment. The (1-10)-th embodiment is configured such that the operator can set the detection pixels 90 from which the dose signals DDS(C) are used to determine the start of the emission of X-rays among all of the detection pixels 90. For example, in a case in which the detection pixels 90X3 illustrated in FIG. 31 in the (1-9)-th embodiment are dispersively arranged on the light detection substrate 35 illustrated in FIG. 28, in chest imaging, the detection pixels 90X3 in a rectangular area LA1 corresponding to the lung field of the patient P are selected and the dose signals DDS(C) from the selected detection pixels 90X3 are used to determine the start of the emission of X-rays as illustrated in FIG. 32. In contrast, in abdominal imaging, the detection pixels 90X3 in a rectangular area LA2 are selected and the dose signals DDS(C) from the selected detection pixels 90X3 are used to determine the start of the emission of X-rays.

In this case, the gate driving unit 108 has a function of selectively applying the gate pulses to the TFTs 106 of the detection pixels 90X3 in the areas LA1 and LA2. In a case in which the detection pixels 90X3 in the area LA1 are selected in chest imaging, the signal lines 42 in a range RLA1 corresponding to the width of the area LA1 become the detection channels 95. Therefore, control is performed such that the power supply state of the ADCs 77 in charge of the range RLA1 is switched or the ADCs 77 are always in the operating state during the AED operation. The ADCs 77 in charge of the other ranges RLA2 and RLA3 are switched to the non-operating state. In contrast, in a case in which the detection pixels 90X3 in the area LA2 are selected in abdominal imaging, control is performed such that the power supply state of the ADCs 77 in charge of the range RLA2 is switched or the ADCs 77 are always in the operating state during the AED operation. In this case, the ADCs 77 in charge of the ranges RLA1 and RLA3 are switched to the non-operating state.

In FIG. 32, the detection pixel 90X3 illustrated in FIG. 31 in the (1-9)-th embodiment has been described as an example. However, the invention is not limited thereto. In the configuration in which the pixel 40 for obtaining the image signal DIS(C) in the image reading operation is also used as the detection pixel 90 for obtaining the dose signal DDS(C) in the AED operation as in the (1-8)-th embodiment illustrated in FIGS. 25 to 27, in a case in which the function of selectively applying the gate pulses G(R) to the TFTs 44 of the pixels 40 in a specific area is provided in the gate driving unit 50, the same effect as described above can be obtained.

For the detection pixels 90X1 and 90X2 illustrated in FIGS. 29 and 30 in the (1-9)-th embodiment, in a case in which the detection pixels 90X1 and 90X2 are arranged only in the area LA1 in the range RLA1 and are arranged only in the area LA2 in the range RLA2, the same effect as described above can be obtained.

(1-11)-th Embodiment

Figure 34:
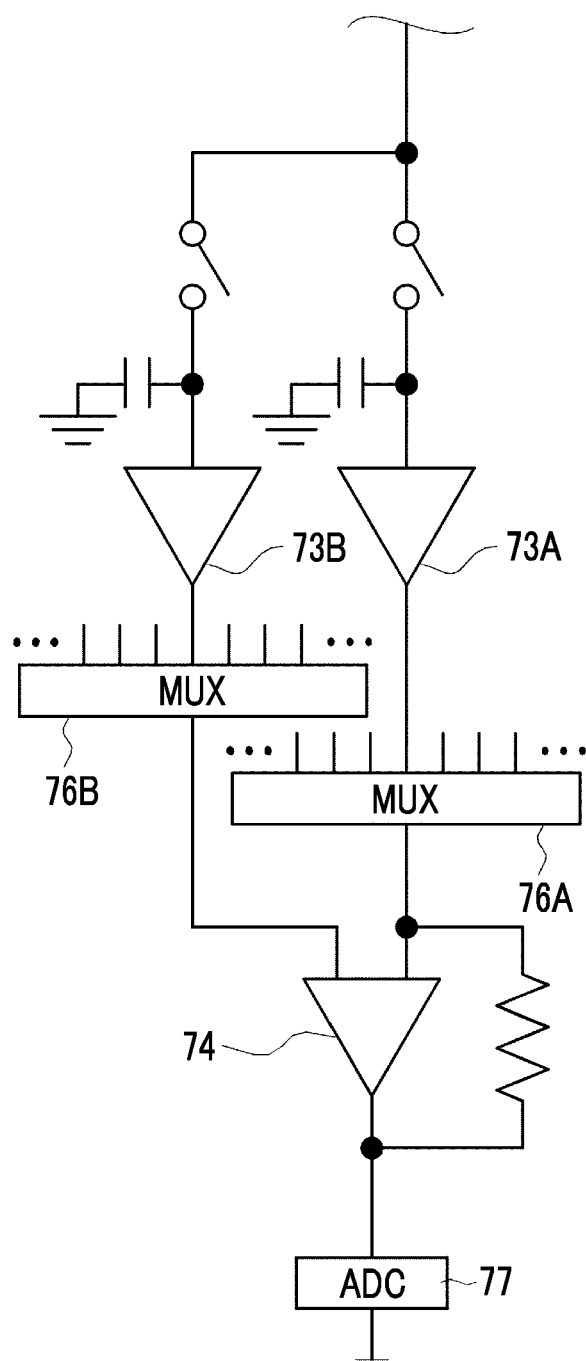
FIG. 34 is a circuit diagram illustrating another example of the connection of the CDS, the MUX, and the ADC.

FIGS. 33 and 34 illustrate a (1-11)-th embodiment. As described above, the dose signal DDS(C) obtained by the AED operation is not used as the image information of the patient P. Therefore, the accuracy required for the image signal DIS(C) output in the image reading operation is not required for the dose signal DDS (C) in the AED operation. In the (1-11)-th embodiment illustrated in FIG. 33, the operation of the CDS 61 in the AED operation is simpler than that in the image reading operation to further reduce the power consumption of the signal processing circuit 51 in the AED operation.

FIG. 33A is a flowchart illustrating the operation of the CDS 61 in the image reading operation which has been described in brief with reference to FIG. 6. That is, the first S/H 73A of the CDS 61 holds a reset noise component (Step ST300). Then, the second S/H 73B holds an analog voltage signal V(C) (Step ST310). Finally, the difference amplifier 74 calculates the difference between the reset noise component and the analog voltage signal V(C) held in the first and second S/Hs 73A and 73B and outputs an analog voltage signal V(C) from which noise has been removed (Step ST320).

In contrast, in the AED operation, the holding of the reset noise component by the first S/H 73A in Step ST300 is skipped and the process starts from the holding of the analog voltage signal V(C) by the second S/H 73B in Step ST310 as illustrated in FIG. 33B. Then, the difference amplifier 74 outputs the analog voltage signal V(C) without calculating the difference between the reset noise component and the analog voltage signal V(C) (Step ST330).

As such, in the AED operation, since the holding of the reset noise component by the first S/H 73A is skipped, the supply of power to the first S/H 73A is not necessary or it is possible to drive the first S/H 73A with power lower than that in the image reading operation. Therefore, it is possible to further reduce the power consumption of the signal processing circuit 51 in the AED operation. In addition, in the AED operation, it is possible to output the analog voltage signal V(C) at a higher speed than that in the image reading operation by a value corresponding to the operation of skipping the holding of the reset noise component by the first S/H 73A.

In the (1-1)-th embodiment, the example in which the difference amplifier 74 is connected to the input terminal of the MUX 76 as illustrated in FIG. 6 has been described. However, the invention is not limited thereto. As illustrated in FIG. 34, two MUXs 76A and 76B may be connected between the first and second S/Hs 73A and 73B and the difference amplifier 74 and the difference amplifier 74 may be connected between the MUXs 76A and 76B and the ADC 77.

In this case, for example, the first and second S/Hs 73A and 73B of a plurality of CDSs 61 corresponding to the columns in the same area AR are connected to the MUXs 76A and 76B, respectively. In the (1-1)-th embodiment, as illustrated in FIG. 6, since the difference amplifier 74 is connected to a stage behind the MUX 76, the difference amplifier 74 is provided for each CDS 61. However, in FIG. 34, since the difference amplifier 74 is connected to a stage behind the MUXs 76A and 76B, the number of difference amplifiers 74 is equal to the number of ADCs 77.

In the configuration illustrated in FIG. 34, as illustrated in FIG. 33B, the holding of the reset noise component by the first S/H 73A in the AED operation is skipped. Therefore, it is possible to reduce power consumption. In this case, it is possible to reduce the supply of power to the MUX 76A in addition to the first S/H 73A. In addition, the number of difference amplifiers 74 is reduced to reduce the supply of power to the difference amplifier 74. Therefore, it is possible to further reduce the power consumption of the signal processing circuit 51 in the AED operation.

(1-12)-th Embodiment

Figure 35:
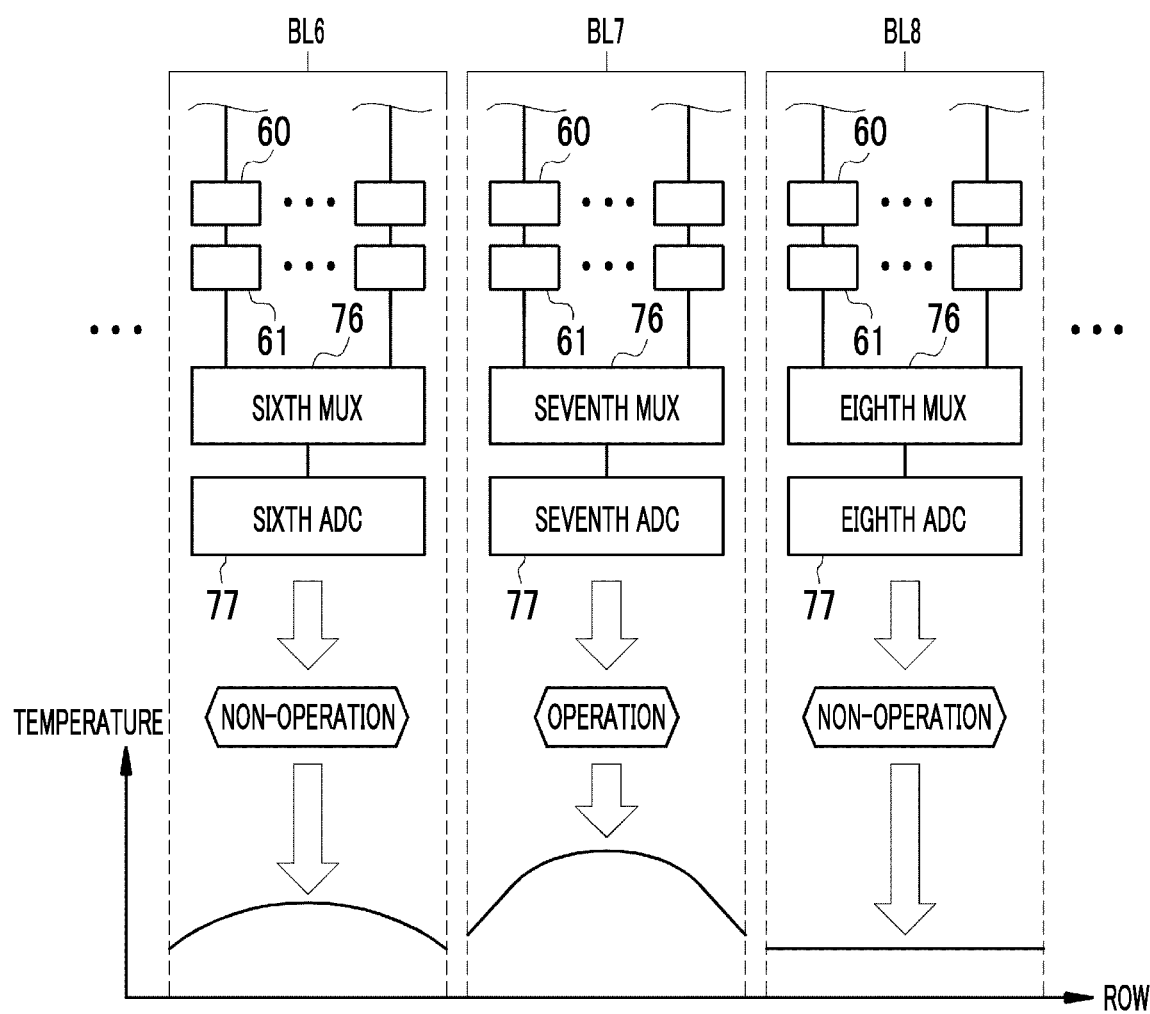
FIG. 35 is a graph illustrating a temperature distribution in a column direction of a signal processing circuit.
Figure 36:
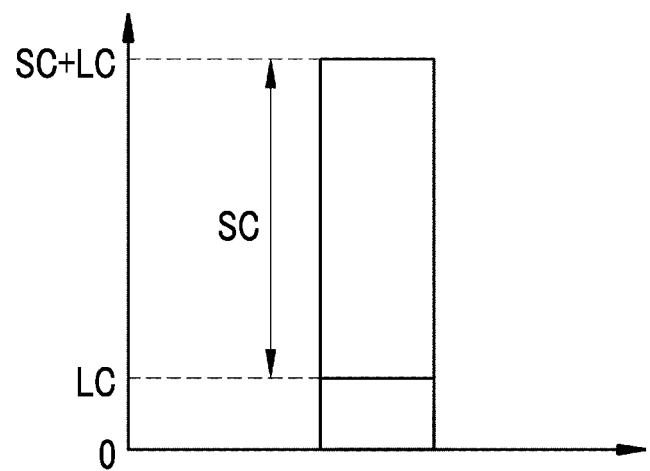
FIG. 36 is a graph illustrating a charge component of a detection channel.
Figure 37:
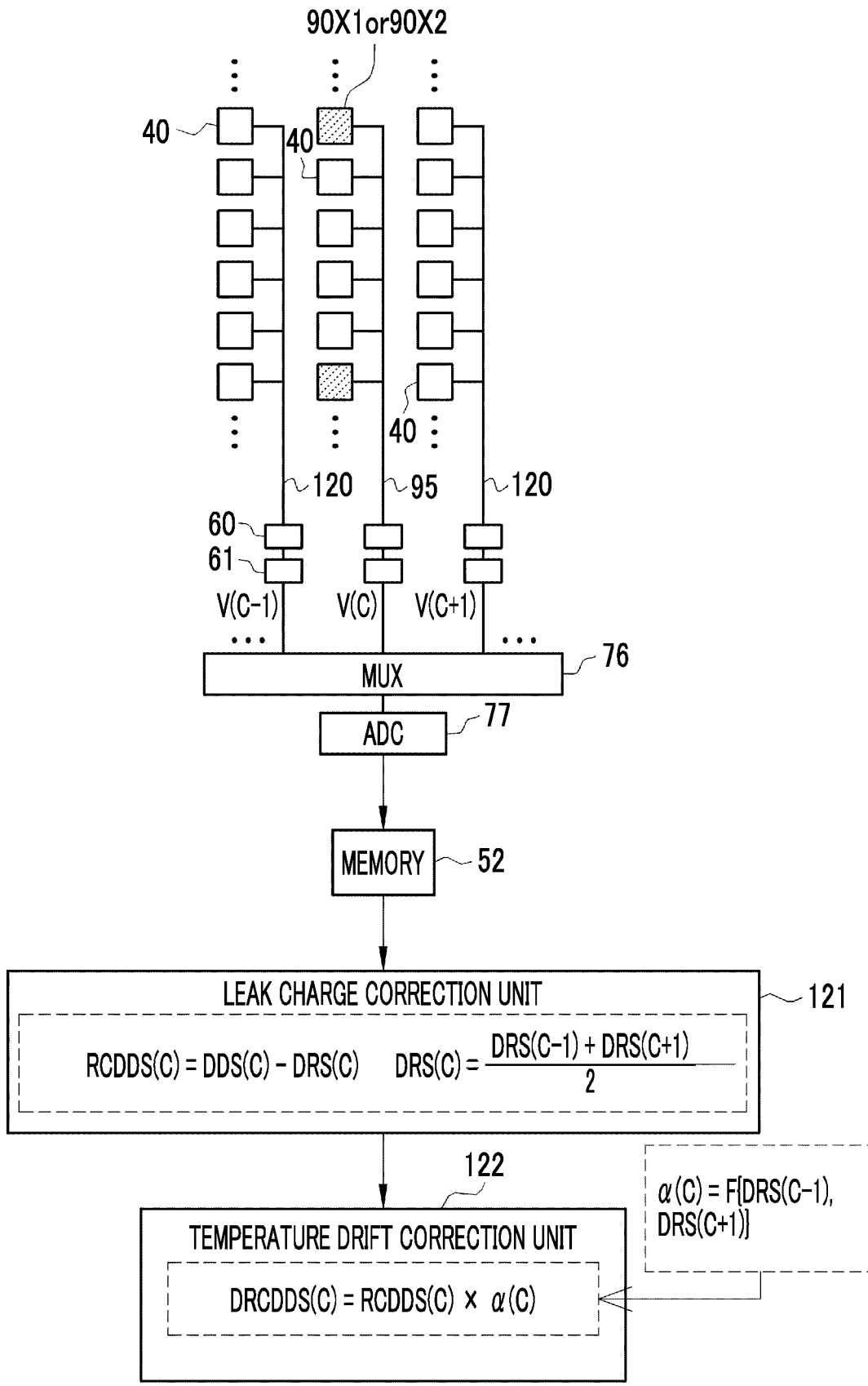
FIG. 37 is a diagram illustrating a (1-12)-th embodiment in which leak charge correction and temperature drift correction are performed.

FIGS. 35 to 37 illustrate a (1-12)-th embodiment. Here, for example, FIG. 35 illustrates a temperature distribution in the column direction of the block BL7 in a case in which the sixth and eighth ADCs 77 adjacent to the seventh ADC 77 illustrated in FIG. 18 in the (1-2)-th embodiment is in the non-operating state for a relatively long time, the power supply state is switched at different timings, and the seven the seventh ADC 77 is in the operating state. That is, the temperature distribution has a mountain shape in which the temperature drops at both ends due to the influence of the adjacent blocks BL6 and BL8 in the non-operating state and the temperature in a central portion is higher than that at both ends. The reason why the temperature distribution of the block BL6 has a gentle mountain shape is that, as illustrated in FIG. 18, the sixth ADC 77 is in the operating state immediately before the seventh ADC 77 changes to the operating state.

In a case in which the block BL is in charge of a large number of columns of the pixels 40, the width of the block BL in the column direction is large. Therefore, for a change in the temperature distribution in the block BL, the central portion is approximately flat and becomes gentle. In contrast, in a case in which the block BL is in charge of a small number of columns of the pixels 40, the width of the block BL in the column direction is small. Therefore, the change in the temperature distribution is steep. In a case in which there is a bias in the temperature distribution in the block BL, a temperature drift occurs in the digital signal DS(C). It is preferable to arrange the detection channel 95 having the detection pixels 90 in a central portion of the area AR in which a temperature gradient is likely to be relatively flat, in order to minimize the influence of the temperature drift.

In the examples illustrated in FIGS. 29 and 30 in the (1-9)-th embodiment, the number of detection pixels 90X1 or 90X2 arranged in one detection channel 95 is less than 1% of the total number of pixels. For example, among 2880 pixels, 12 pixels are the detection pixels. As such, the following relationship is established between the number of pixels 40 and the number of detection pixels 90X1 or 90X2: the number of pixels 40» the number of detection pixels 90X1 or 90X2.

Here, even in a case in which the TFT 44 is in an off state, a very small amount of charge generated in the pixel 40 flows into the signal line 42. The charge is referred to as a leak charge. As schematically illustrated in FIG. 36, in addition to charge SC generated in the detection pixel 90X1 or 90X2, the leak charge LC flows into the detection channel 95 in the examples illustrated in FIGS. 29 and 30. Since the leak charge LC is added to the charge SC generated in the detection pixel 90X1 or 90X2 which is desired to be originally extracted as the dose signal DDS(C), it becomes noise in a case in which the start of the emission of X-rays is determined. In addition, since the number of pixels 40 » the number of detection pixels 90X1 or 90X2 is satisfied, the amount of leak charge LC is not negligible with respect to the amount of charge SC generated in the detection pixel 90X1 or 90X2. As a result, the risk of erroneously determining the start of the emission of X-rays increases. In the (1-12)-th embodiment, correction which removes the influence of the leak charge LC from the dose signal DDS(C) of the detection channel 95 and then removes the influence of the temperature drift is performed.

Specifically, as illustrated in FIG. 37, the columns of only the pixels 40 without including the detection pixel 90X1 or 90X2 are provided adjacent to the detection channel 95 having the detection pixels 90X1 or 90X2 arranged therein such that the detection channel 95 is interposed therebetween. Hereinafter, the signal line 42 corresponding to the column of only the pixels 40 without including the detection pixel 90X1 or 90X2 is referred to as a reference channel 120.

In FIG. 37, the detection channel 95 and the reference channel 120 are connected to the same MUX 76 and the same ADC 77. That is, the detection channel 95 and the reference channel 120 are in the same block BL. In this case, the control unit 54 changes the ADC 77 that is in charge of both the detection channel 95 and the reference channel 120 to the operating state during the AED operation. In a case in which the detection channel 95 and the reference channel 120 are divided into different blocks BL and are connected to different ADCs 77, the control unit 54 changes the ADC 77 that is in charge of the detection channel 95 to the operating state and changes the ADC 77 that is in charge of the reference channel 120 to the operating state.

Then, the ADC 77 outputs the dose signal DDS(C) based on the analog voltage signal V(C) from the detection channel 95 and the dose signals DDS(C−1) and DDS(C+1) based on the analog voltage signals V(C−1) and V(C+1) from the reference channel 120 to the memory 52. Hereinafter, the dose signals DDS(C−1) and DDS(C+1) are referred to as reference signals DRS(C−1) and DRS(C+1), respectively.

A leak charge correction unit 121 accesses the memory 52 and reads the dose signal DDS(C) from the memory 52. The leak charge correction unit 121 is provided in, for example, the control unit 54. The leak charge correction unit 121 performs subtraction represented by the following Expression (1) to obtain a leak charge corrected dose signal RCDDS(C) from the dose signal DDS(C):

$$RCDDS(C)=DDS(C)-DRS(C) \qquad (1)$$

(where DRS(C)={DRS(C−1)+DRS(C+1)}/2). That is, the leak charge corrected dose signal RCDDS(C) is obtained by subtracting DRS(C), which is the average value of two reference signals DRS(C−1) and DRS(C+1) from the reference channels 120 corresponding to two columns, from the dose signal DDS(C) from the detection channel 95.

The reference signals DRS(C−1) and DRS(C+1) are components based on the leak charge LC of the pixels 40 connected to the reference channels 120. It is considered that the average value DRS(C) of the reference signals DRS(C−1) and DRS(C+1) is substantially matched with the component based on the leak charge LC of the pixels 40 connected to the detection channel 95 since the detection channel 95 and the reference channel 120 are adjacent to each other and include almost the same number of pixels 40. Therefore, the subtraction represented by Expression (1) is performed to remove the component of the leak charge LC from the dose signal DDS(C).

A temperature drift correction unit 122 is provided in a stage behind the leak charge correction unit 121. The temperature drift correction unit 122 is provided in, for example, the control unit 54 similarly to the leak charge correction unit 121. The temperature drift correction unit 122 multiplies the leak charge corrected dose signal RCDDS(C) by a correction coefficient α(C) to calculate a temperature drift corrected dose signal DRCDDS(C) as illustrated in the following Expression (2):

$$DRCDDS(C)=RCDDS(C)\times\alpha(C) \qquad (2).$$

The temperature distribution, which is illustrated in FIG. 35, in the signal processing circuit 51 including the detection channel 95 and the reference channel 120 is reflected in the reference signals DRS(C−1) and DRS(C+1). That is, the degree of the temperature drift occurring in the dose signal DDS(C) is known from the reference signals DRS(C−1) and DRS(C+1). The correction coefficient α(C) is calculated from a calculation formula F{DRS(C−1), DRS(C+1)} having the reference signals DRS(C−1) and DRS(C+1) as variables. The correction coefficient α(C) is used such that the value of the leak charge corrected dose signal RCDDS (C) is equal to that in a case in which the leak charge corrected dose signal RCDDS(C) is read in a standard state in which all of the ADCs 77 are in the operating state in the image reading operation and each block BL1-16 is in a thermal equilibrium state. The correction coefficient α(C) is calculated for each detection channel 95. In addition, the correction coefficient α(C) may be calculated from a calculation formula having the average value DRS(C) of the reference signals DRS(C−1) and DRS(C+1) as a variable.

A temperature measurement function of measuring the temperature TP of a central portion of each block BL is provided in some chips CP in advance. In this case, the correction coefficient α(C) is calculated on the basis of the temperature TP acquired by the temperature measurement function (using a calculation formula having the temperature TP as a variable). In a case in which the temperature measurement function is not provided in the chip CP, the temperature measurement function may be separately provided to acquire the temperature TP.

The correction of the temperature drift by the temperature drift correction unit 122 may not be performed in a case in which it is determined that there is no temperature drift in the dose signal DDS(C) such as a case in which the temperature TP is in the standard state. Specifically, a threshold value is set to the temperature TP. In a case in which the temperature TP is equal to or less than the threshold value, the temperature drift is not corrected. In a case in which the temperature TP is greater than the threshold value, the temperature drift is corrected.

In the image reading operation, since all of the ADCs 77 are always in the operating state, the bias in the temperature distribution illustrated in FIG. 35 is less likely to occur. Of course, the temperature drift correction unit 122 may also perform temperature drift correction for the image signal DIS(C).

In a case in which the power supply state of the ADCs 77 is switched in units of the chips CP as in the (1-4)-th embodiment illustrated in FIG. 20, the bias in the temperature distribution illustrated in FIG. 35 does not occur in units of the blocks BL, but occurs in units of the chips CP. In this case, the temperature TP is measured in units of the chips CP and the temperature drift is corrected in units of the chips CP.

In a case in which the power supply state of the ADCs 77 is switched in units of the chips CP, it is preferable to take measures to prevent the temperature distribution from being biased, for example, measures to connect adjacent chips CP with a thermally conducting member, such as a heat sink or a heat pipe.

In FIG. 37, one reference channel 120 is provided on each side of the detection channel 95, that is, a total of two reference channels 120 are provided adjacent to each other with the detection channel 95 interposed therebetween. However, a plurality of reference channels 120 may be provided on each side of the detection channel 95. It is preferable that the number of reference channels 120 provided on each side is equal to or greater than 2, that is, the total number of reference channels 120 is equal to or greater than 4. The reason is that, in a case in which the number of reference channels 120 is small, the number of reference signals is small, and there is a variation in the value of the reference signal value in each reference channel 120, the reliability of the average value DRS(C) of the reference signals subtracted from the dose signal DDS(C) is reduced.

In the case of the detection pixel 90X3 illustrated in FIG. 31 in the (1-9)-th embodiment, the signal line 42 and the detection channel 95 are separately provided and the pixel 40 is not connected to the detection channel 95. Therefore, there is no concern that the leak charge LC of the pixel 40 will flow into the detection channel 95. In a case in which the detection channel 95 is also used as the signal line 42 in FIG. 31 and the TFT 106 is turned off, the charge generated in the detection pixel 90X3 does not flow into the signal line 42. Therefore, in a case in which the TFT 106 is in the off state, the signal line 42 that is also used as the detection channel 95 acts just like the reference channel 120. Therefore, in this case, the digital signal DS(C) read in a state in which the TFT 106 is turned off may be replaced with a reference signal and the reference signal may be subtracted from the dose signal DDS(C) read in a state in which the TFT 106 is turned on. That is, in any case illustrated in FIG. 31, it is not necessary to provide a dedicated reference channel 120.

(1-13)-th Embodiment

In a (1-13)-th embodiment illustrated in FIG. 38, in the AED operation, the control unit 54 switches an interface (hereinafter, referred to as an I/F) that transmits the digital signal DS(C) in a stage behind the ADC 77 to one having a lower power consumption than that in the image reading operation. In this configuration, the power consumption of the signal processing circuit 51 in the AED operation may be reduced.

In FIG. 38, two types of interfaces, that is, a low voltage differential signaling (LVDS) I/F 125 and a CMOS I/F 126 are prepared as the I/F for transmitting the digital signal DS(C) between the ADC 77 and the memory 52. The LVDS I/F 125 has a higher transmission accuracy than the CMOS I/F 126, but has a higher power consumption than the CMOS I/F 126. The control unit 54 controls the operation of a switch 127 to switch the transmission I/Fs.

Figure 38A:
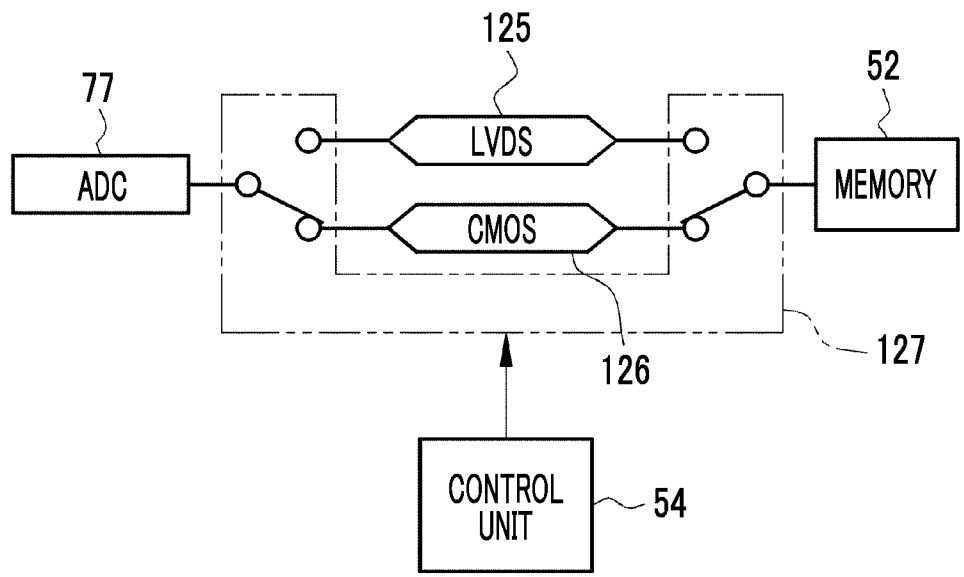
FIG. 38A is a diagram illustrating an AED operation according to a (1-13)-th embodiment in which a digital signal transmission I/F is switched.
Figure 38B:
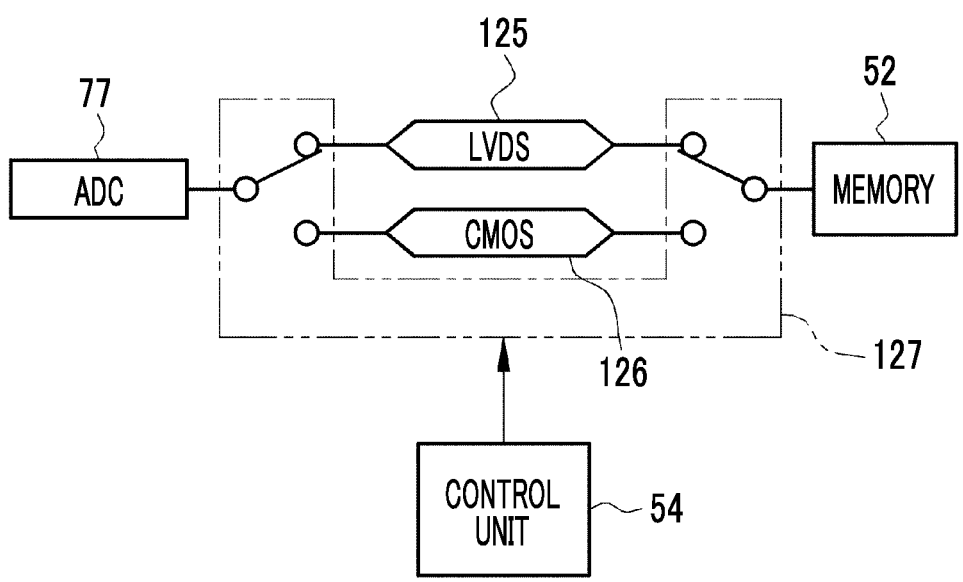
FIG. 38B is a diagram illustrating an image reading operation according to the (1-13)-th embodiment.

FIG. 38A illustrates a case in which the AED operation is performed and FIG. 38B a case in which the image reading operation is performed. That is, the CMOS I/F 126 is selected in the AED operation and the LVDS I/F 125 is selected in the image reading operation.

As such, since the CMOS I/F 126 is selected in the AED operation, it is possible to further reduce the power consumption of the signal processing circuit 51 in the AED operation. The accuracy of the transmission of the dose signal DDS(C) is low. However, since the dose signal DDS(C) is not used as the image information of the patient P, some errors in transmission do not cause a big problem. On the other hand, since the LVDS I/F 125 is selected in the image reading operation, power consumption increases, but it is possible to accurately transmit the image signal DIS(C) to the memory 52.

In addition, only the CMOS I/F 126 may be provided as the transmission I/F for the digital signal DS(C) between the ADC 77 and the memory 52 and the supply voltage to the CMOS I/F 126 may be switched. For example, the supply voltage is 5.0 V in the image reading operation and is 3.3 V in the AED operation. Alternatively, the supply voltage may be 2.5 V in the image reading operation and may be 1.8 V in the AED operation. As the supply voltage becomes higher, the dynamic range becomes wider and the accuracy of transmission becomes higher. However, power consumption becomes higher. Therefore, in the AED operation, the supply voltage is switched to a lower voltage than that in the image reading operation. As a result, it is possible to further reduce the power consumption of the signal processing circuit 51 in the AED operation.

In each of the above-described embodiments, the second state has been described as the non-operating state. As described above, the non-operating state includes the state in which the power PSL_A is supplied, the power-off state in which no power is supplied to the ADC 77, and the state in which the supply of the clock signal to the ADC 77 is stopped. However, the second state is not limited to the non-operating state. For example, the second state may be a state in which the number of pulses per unit time in the clock signal supplied to the ADC 77 is less than that in the first state and the power consumption of the ADC 77 per unit time is less than that in the first state.

2. Second Invention

In a second invention illustrated in FIGS. 39 to 43 which will be described below, the control unit 54 changes at least one of the non-detection CAs 131 (see FIG. 39A) which are the CAs 60 connected to the non-detection channels 130 (see FIG. 39A) as the signal lines 42 other than the detection channels 95 among a plurality of CAs 60 to a power saving state in which power supplied to the non-detection CAs 60 in the AED operation is lower than normal power in the image reading operation. Therefore, the power supplied to the CAs 60 including the non-detection CA 131 in the AED operation is lower than that in the image reading operation.

In the second invention, for example, the X-ray imaging system 10 and the electronic cassette 16 have the same basic configuration as those in the first invention. In addition, the patterns described in the (1-1)-th to (1-7)-th embodiments can be applied to the switching pattern of the power supply state of the ADC 77. Further, the second invention may be combined with other embodiments (the (1-8)-th to (1-13)-th embodiments) of the first invention. Hereinafter, the same components as those in the first invention are denoted by the same reference numerals and the description thereof will not be repeated. The difference from the first invention will be mainly described.

(2-1)-th Embodiment

FIGS. 39 and 40 illustrate a (2-1)-th embodiment. In the (2-1)-th embodiment, for example, a configuration including the detection pixel 90X1 illustrated in FIG. 29 or the detection pixel 90X2 illustrated in FIG. 30 in the (1-9)-th embodiment will be described. However, the configuration is not limited thereto.

Figure 39A:
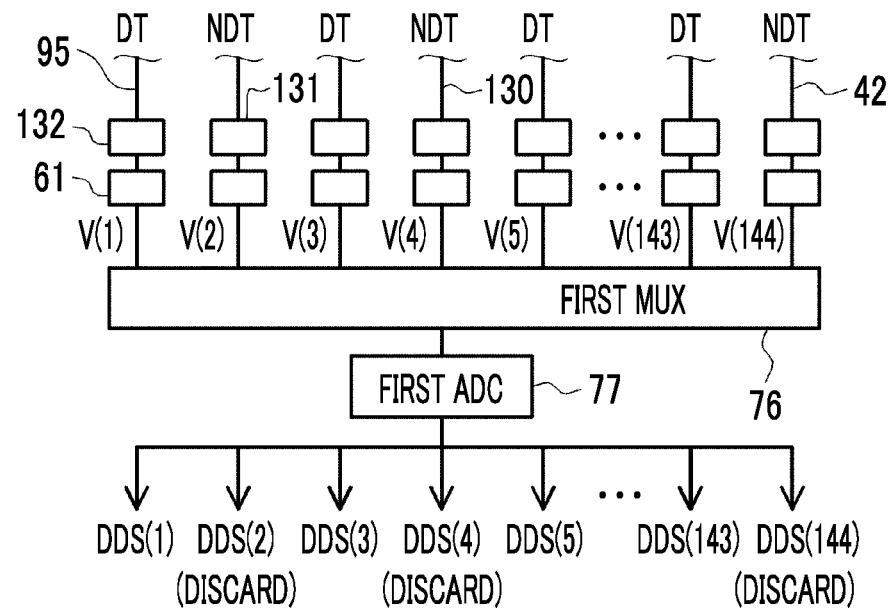
FIG. 39A is a diagram schematically illustrating the configuration of a (2-1)-th embodiment.

In the (2-1)-th embodiment, FIG. 39A illustrates a case in which odd-numbered columns, such as the first, third, fifth, . . . , 143rd columns, are the detection channels 95 and the even-numbered columns, the second, fourth, sixth, . . . , 144th columns, are the non-detection channels 130 for simplicity of explanation. Hereinafter, the CA 60 connected to the detection channel 95 is referred to as a detection CA 132 in order to distinguish the CA 60 from the non-detection CA 131 which is the CA 60 connected to the non-detection channel 130. In addition, alphabets DT above the detection channel 95 indicate that the column is the detection channel 95 and alphabets NDT above the non-detection channel 130 indicate that the column is the non-detection channel 130.

The MUX 76 sequentially selects the analog voltage signals V(C) from a plurality of CAs 60 and outputs the selected analog voltage signal V(C) to the ADC 77 as in each of the above-described embodiments.

Figure 39B:
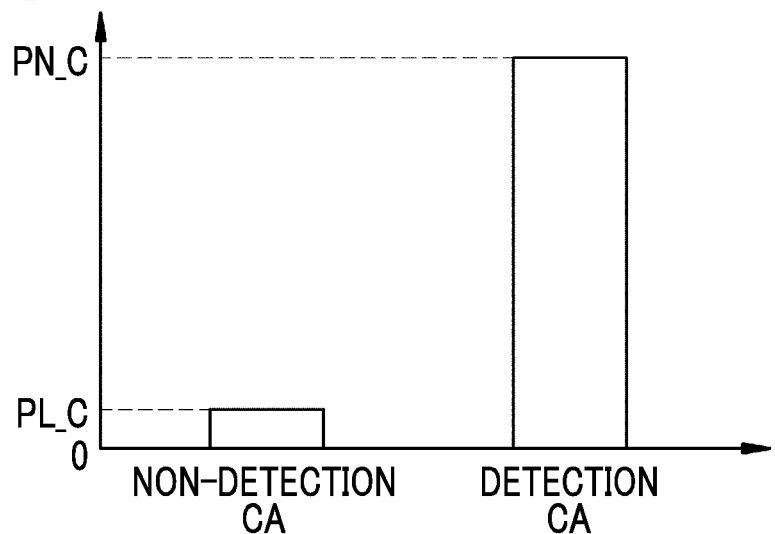
FIG. 39B is a graph illustrating the supply of power to the CA.

In the (2-1)-th embodiment, as illustrated in FIG. 39B, it is assumed that the power P_C supplied to the CA 60 in the AED operation is PN_C in the case of the detection CA 132 and is PL_C lower than PN_C in the case of the non-detection CA 131. The supply power PN_C is power supplied to all of the CAs 60 in the image reading operation and corresponds to normal power. The power PL_C supplied to the non-detection CA 131 is, for example, about $\frac{1}{10}$ of the normal power PN_C. That is, the state of the non-detection CA 131 illustrated in FIG. 39B is a low power state in which the power PL_C that is lower than the normal power PN_C and is greater than 0 is supplied.

As such, since only the power PL_C lower than the normal power PN_C is supplied to the non-detection CA 131, the digital signal DS(C) based on the analog voltage signal V(C) from the non-detection CA 131 has a meaningless value in terms of data. Therefore, as illustrated in FIG. 39A, the control unit 54 discards the digital signal DS(C) based on the analog voltage signal V(C) from the non-detection CA 131, without using it as the dose signal DDS(C).

FIG. 40 is a flowchart illustrating the procedure of the operation of the electronic cassette according to the (2-1)-th embodiment. The flowchart differs from the flowchart illustrated in FIG. 17 in the (1-1)-th embodiment in Step ST1202 and Step ST1802 surrounded by a one-dot chain line. Hereinafter, only the difference will be described.

In Step ST1202, in the AED operation, the power supplied to the detection CA 132 is set to the normal power PN_C and the power supplied to the non-detection CA 131 is set to PL_C lower than PN_C (irradiation start detection step). In Step ST1802, in the image reading operation, the power supplied to all of the CAs 60 is set to the normal power PN_C without distinguishing between the detection CA 132 and the non-detection CA 131 (image reading step).

As such, since the non-detection CA 131 is in the power saving state in which the power supplied to the non-detection CA 131 in the AED operation is lower than the normal power, it is possible to reduce the power consumption of the signal processing circuit 51 in the AED operation. Therefore, similarly to the first invention, the battery 65 lasts longer than that in the related art and thus the number of times the battery 65 is charged is reduced. Therefore, it is possible to improve imaging efficiency.

The non-detection CA 131 that is in the power saving state in the AED operation may be at least one of the non-detection CAs 131. Of course, it is preferable that all of the non-detection CAs 131 are changed to the power saving state in order to obtain the maximum effect.

(2-2)-th Embodiment

Figure 41:
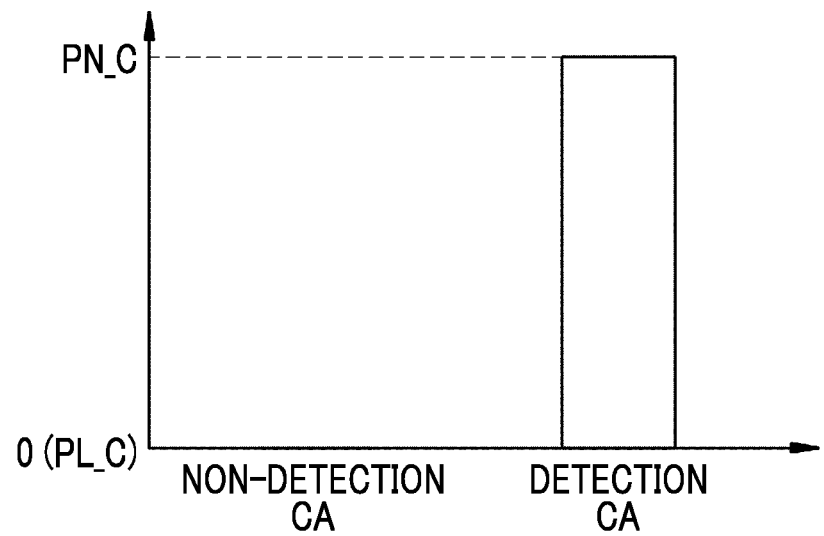
FIG. 41 is a graph illustrating another example of the supply of power to the CA.

FIG. 41 illustrates a (2-2)-th embodiment. In the (2-1)-th embodiment illustrated in FIGS. 39 and 40, the power PL_C supplied to the non-detection CA 131 in the AED operation is a value less than 0. However, in the (2-2)-th embodiment, as illustrated in FIG. 41, the power PL_C supplied to the non-detection CA 131 in the AED operation is 0. That is, the non-detection CA 131 is a power-off state in which the supply of power is stopped.

As such, in a case in which the non-detection CA 131 is in the power-off state, the power supplied to the non-detection CA 131 is 0. Therefore, it is possible to further reduce the power consumption of the non-detection CA 131 as compared to the (2-1)-th embodiment illustrated in FIGS. 39 and 40.

However, in a case in which the non-detection CA 131 is in the power-off state, a virtual short state between two input terminals of the non-detection CA 131 is not maintained and the potential of the input stage of the non-detection CA 131 becomes indefinite. Therefore, the charge of the non-detection channel 130 also becomes unstable, which has a bad influence on the image reading operation later. For this reason, it is preferable to supply the power PL_C that does not cause the potential of the input stage of the non-detection CA 131 to be indefinite to change the non-detection CA 131 to a low power state as in the (2-1)-th embodiment rather than to set the power supplied to the non-detection CA 131 to 0 to change the non-detection CA 131 to the power-off state as in the (2-2)-th embodiment.

In a case in which the non-detection CA 131 is in the power-off state, a measure illustrated in FIG. 42 may be taken in order to prevent a bad influence on the image reading operation. That is, a switch 133 that is turned on and off under the control of the control unit 54 is provided in a stage before the non-detection CA 131. Then, the control unit 54 turns off the switch 133 to disconnect the non-detection CA 131 from the non-detection channel 130 in the AED operation illustrated in FIG. 41A in which no power is supplied. In addition, the control unit 54 applies a reference potential, which is the same as that in a case in which the normal power PN_C is supplied, to the non-detection CA 131. In contrast, the control unit 54 turns on the switch 133 in the image reading operation illustrated in FIG. 41B in which the normal power PN_C is supplied. According to this configuration, it takes a lot of time and effort to provide the switch 133, but the instability of the charge of the non-detection channel 130 caused by the indefinite potential of the input stage of the non-detection CA 131 does not has an influence on the image reading operation.

In this case, similarly to the (2-1)-th embodiment, the non-detection CA 131 that is in the power-off state in the AED operation may be at least one of the non-detection CAs 131. It is preferable that all of the non-detection CAs 131 are in the power-off state in order to reduce power consumption.

(2-3)-th Embodiment

Figure 43:
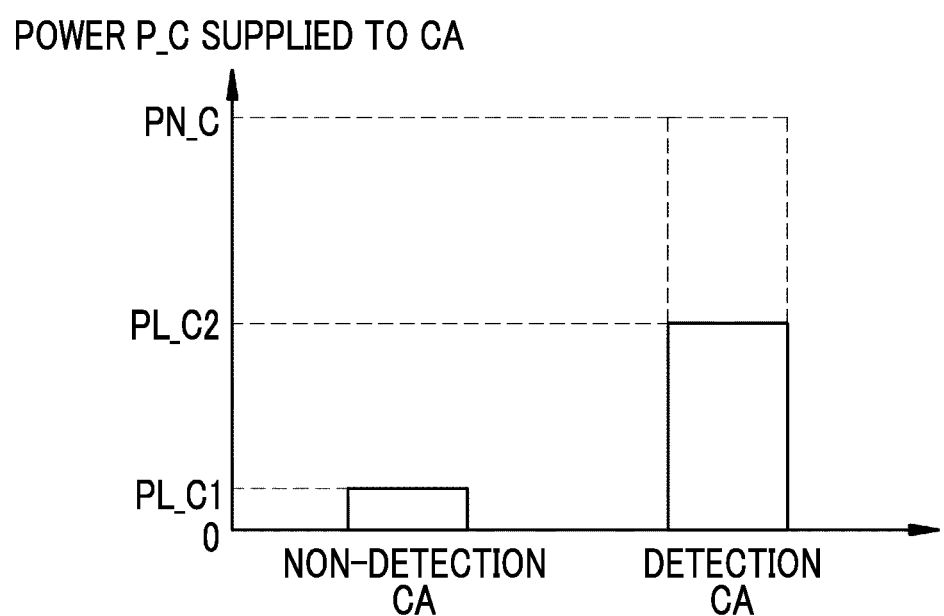
FIG. 43 is a graph illustrating still another example of the supply of power to the CA.

In a (2-3)-th embodiment illustrated in FIG. 43, in addition to the non-detection CA 131, the detection CA 132 is driven in a low power state in which power lower than the normal power PN_C and is greater than 0 is supplied. Specifically, the power supplied to the non-detection CA 131 in the AED operation is PL_C1 that is $\frac{1}{10}$ of the normal power PN_C and the power supplied to the detection CA 132 is PL_C2 that is $\frac{1}{2}$ of the normal power PN_C. The transient response characteristic of the detection CA 132 is reduced in correspondence to $\frac{1}{2}$ of the normal power PN_C. In this case, the operation speed of the ADC 77 is delayed so as to be matched with the reduction in the transient response characteristic. This configuration does not cause any problem because the dose signal DDS(C) that is meaningful in terms of data is obtained. Since the power supplied to the detection CA 132 in addition to the non-detection CA 131 is reduced, it is possible to further reduce the power consumption of the signal processing circuit 51 in the AED operation.

In the (2-3)-th embodiment, similarly to the non-detection CA 131 according to each of the above-described embodiments, the detection CA 132 that is in the low power state in the AED operation may be at least one of the detection CAs 132. It is preferable that all of the detection CAs 132 are in the low power state in order to reduce power consumption.

As described above, each embodiment of the second invention may be combined with each embodiment of the first invention. For example, as illustrated in FIG. 14 of the (1-1)-th embodiment, the control unit 54 may periodically switch the power supply state of the ADC 77 and the MUX 76 which form the block BL from the first state to the second state. In this case, the first state is, for example, the operating state and is a state in which power required to fulfill the functions of each of the MUX 76 and the ADC 77 is supplied to each of the MUX 76 and the ADC 77. In contrast, the second state is, for example, the non-operating state and is a state in which power incapable of fulfilling the functions is supplied to at least one of the MUX 76 or the ADC 77 or a state in which no clock signal is applied to the ADC 77. Further, the second state includes a state in which the number of pulses per unit time in the clock signal applied to the ADC 77 is less than that in the first state.

For example, the switching patterns of power supply to the ADC 77 and the block BL in the second invention and the first invention may be combined as follows. First, in a case in which there are two or more blocks BL including the MUX 76 and the ADC 77 whose power supply state is periodically switched as illustrated in, for example, FIG. 14 of the (1-1)-th embodiment, the control unit 54 may shift the switching timing of the power supply state of at least two of the two or more blocks BL.

In addition, the control unit 54 may shift the switching timing of the power supply state for each of a plurality of groups to which two or more blocks BL belong, as illustrated in, for example, FIG. 14 of the (1-1)-th embodiment. In this case, it is preferable that at least one block BL is disposed between two blocks BL belonging to the same group. Alternatively, as illustrated in, for example, FIG. 18 of the (1-2)-th embodiment, the switching timing of the power supply state of all of the two or more blocks BL may be shifted.

As illustrated in, for example, FIG. 21 of the (1-5)-th embodiment, in a case in which there are a plurality of blocks BL including the MUX 76 to which only the non-detection CA 131 is connected, at least one of the plurality of blocks BL may be always in the second state.

As in the (1-12)-th embodiment illustrated in FIGS. 35 to 37, leak charge correction and temperature drift correction may be performed for the dose signal DDS(C).

In addition, the (1-8)-th embodiment illustrated in FIGS. 25 to 27 in which the detection channel 95 that is the signal line 42 to which the detection pixel 90 used for the AED operation is connected is set, the (1-9)-th embodiment illustrated in FIGS. 28 to 31 in which the detection pixel 90X used only for the AED operation is provided, the (1-10)-th embodiment illustrated in FIG. 32 in which the setting of the detection pixel 90 can be changed, the (1-11)-th embodiment illustrated in FIGS. 33 and 34 in which the operation of the CDS 61 in the AED operation is simplified, and the (1-13)-th embodiment illustrated in FIG. 38 in which the digital signal transmission I/F is switched may be combined with each other.

3. Third Invention

In a third invention illustrated in FIGS. 44 to 49 which will be described below, the control unit 54 selectively outputs the analog voltage signals V(C) from some CAs including the detection CA 132 to the ADC 77, directs the ADC 77 to perform only an AD conversion process for the selectively output analog voltage signal V(C), and reduces the number of pulses per unit time in the clock signal of the ADC 77 in the AED operation to be less than that in the image reading operation.

In the third invention, similarly to the second invention, for example, the X-ray imaging system 10 and the electronic cassette 16 have the same basic configuration as those in the first invention. In addition, the patterns described in the (1-1)-th to (1-7)-th embodiments can be applied to the switching pattern of the power supply state of the ADC 77. Further, the third invention may be combined with other embodiments (the (1-8)-th to (1-13)-th embodiments) of the first invention and the (2-1)-th to (2-3)-th embodiments of the second invention. Hereinafter, the same components as those in the first and second inventions are denoted by the same reference numerals and the description thereof will not be repeated. The difference from the first and second inventions will be mainly described.

(3-1)-th Embodiment

FIGS. 44 to 48 illustrate a (3-1)-th embodiment. In the (3-1)-th embodiment, similarly to the (2-1)-th embodiment, for example, a configuration including the detection pixel 90X1 illustrated in FIG. 29 or the detection pixel 90X2 illustrated in FIG. 30 in the (1-9)-th embodiment will be described. However, the configuration is not limited thereto.

Figure 44:
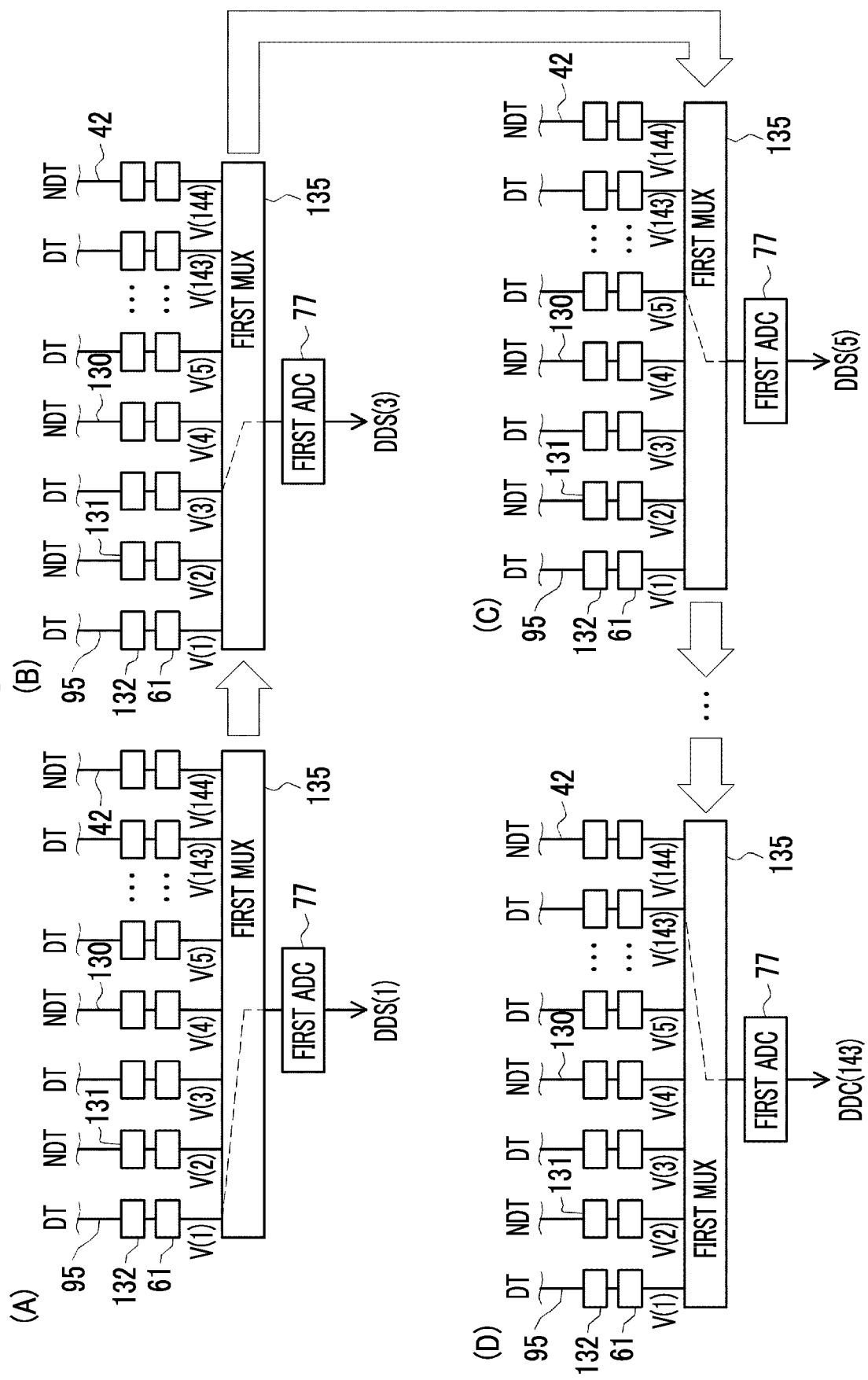
FIG. 44 is a diagram illustrating the procedure of the reading of a dose signal by the first MUX and the first ADC in a (3-1)-th embodiment. (A) of FIG. 44 illustrates an aspect in which a dose signal corresponding to a first column is read, (B) of FIG. 44 illustrates an aspect in which a dose signal corresponding to a third column is read, (C) of FIG. 44 illustrates an aspect in which a dose signal corresponding to a fifth column is read, and (D) of FIG. 44 illustrates an aspect in which a dose signal corresponding to a 143rd column is read.

FIG. 44 illustrates the procedure of reading the dose signals DDS(C) in the area AR1 including the first to 144th columns as in FIG. 9. FIG. 44 illustrates a case in which odd-numbered columns, such as the first, third, fifth, . . . , 143rd columns, are the detection channels 95 and the even-numbered columns, the second, fourth, sixth, . . . , 144th columns, are the non-detection channels 130 as in FIG. 39A.

In this case, the difference from FIG. 39A is that the MUX 76 is changed to a MUX 135. The MUX 76 has only the function of sequentially selecting the columns one by one. In contrast, the MUX 135 has a function of skipping the non-detection channels 130 corresponding to the even-numbered columns and sequentially selecting the analog voltage signals V(C) from the detection CAs 132 of the detection channels 95 corresponding to the odd-numbered columns. That is, the MUX 135 has a function of selecting the analog voltage signal V(C) from some of a plurality of connected CAs 60, in this case, the detection CAs 132 of the detection channels 95. For example, this function can be implemented by providing a switch in a flip-flop circuit of a shift register forming the MUX 135.

In the procedure of reading the dose signal DDS(C), first, as illustrated in (A) of FIG. 44, the first MUX 135 selects an analog voltage signal V(1) corresponding to the first column. Then, the analog voltage signal V(1) is input to the first ADC 77 and the first ADC 77 converts the analog voltage signal V(1) into a dose signal DDS(1). Then, as illustrated in (B) of FIG. 44, an analog voltage signal V(2) corresponding to the second column is skipped and the first MUX 135 selects an analog voltage signal V(3) corresponding to the third column. Then, the analog voltage signal V(3) is input to the first ADC 77 and the first ADC 77 converts the analog voltage signal V(3) into a dose signal DDS(3). Then, as illustrated in (C) of FIG. 44, the first MUX 135 selects an analog voltage signal V(5) corresponding to the fifth column. Then, the analog voltage signal V(5) is input to the first ADC 77 and the first ADC 77 converts the analog voltage signal V(5) into a dose signal DDS(5).

This series of operations are repeated by the first MUX 76 and the first ADC 77. Finally, as illustrated in (D) of FIG. 44, an analog voltage signal V(143) corresponding to the 143rd column is converted into a dose signal DDS(143). Then, the reading of the dose signals DDS(1), DDS(3), DDS(5), . . . , DDS(143) in the area AR1 ends. This holds for each MUX 135 and each ADC 77 in the other areas AR2 to AR16.

As such, while the image signals DIS(C) corresponding to all columns are read in the image reading operation, only the dose signals DDS(C) corresponding to the odd-numbered columns are selectively read in the AED operation. Therefore, in the AED operation, the number of digital signals DS(C) that need to be read at the same time is ½ of that in the image reading operation. In the AED operation, in a case in which the dose signals DDS(C) whose number has been reduced by half are read at the same time as those in the image reading operation that reads the image signals DIS(C) corresponding to all of the columns, it is possible to reduce the operation speed of the ADC 77 by a value corresponding to the reduction in the reading time.

Figure 45:
FIG. 45 is a graph illustrating the number of pulses per unit time in the clock signal of the ADC.

Specifically, as illustrated in FIG. 45, the number of pulses NPU_A per unit time in the clock signal of the ADC 77 is NPUN_A which is the normal number of pulses in the image reading operation and is NPUL_A that is ½ of NPUN_A in the AED operation.

Figure 46:
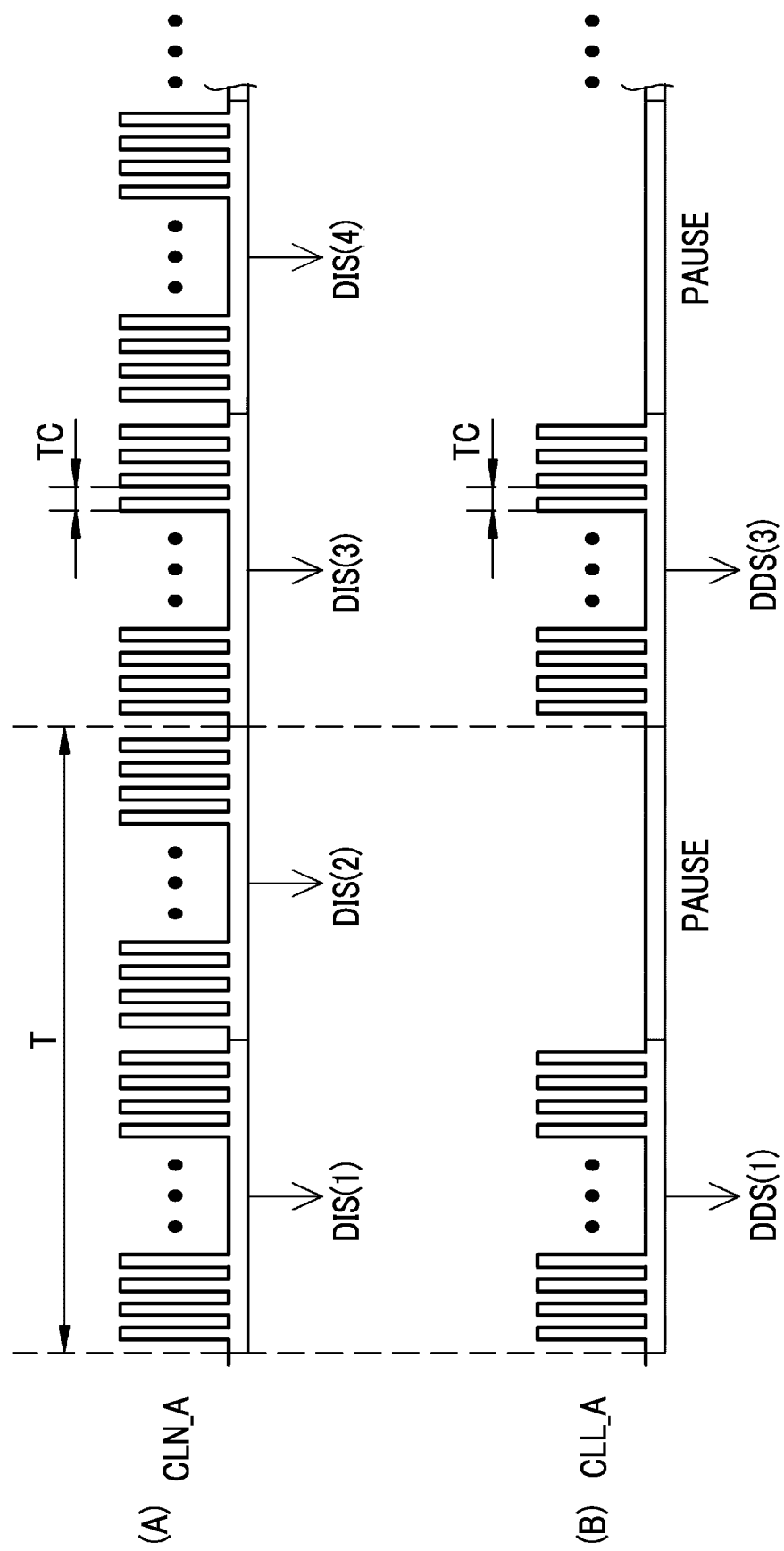
FIG. 46 is a diagram illustrating a first method that reduces the number of pulses per unit time in the clock signal of the ADC in the AED operation to be less than that in the image reading operation. (A) of FIG. 46 illustrates the clock signal in the image reading operation and (B) of FIG. 46 illustrates the clock signal in the AED operation.

There are two methods for setting the number of pulses per unit time in the clock signal of the ADC 77 to NPUL_A that is ½ of NPUN_A in the image reading operation. FIG. 46 illustrates the first method. (A) of FIG. 46 illustrates a clock signal CLN_A in the image reading operation and (B) of FIG. 46 illustrates a clock signal CLL_A in the AED operation.

In FIG. 46, for the period TC of the clock signal, the period of the clock signal CLN_A in the image reading operation is equal to the period of the clock signal CLL_A in the AED operation. The clock signal CLN_A is continuously generated without intermission, regardless of the detection channel 95 and the non-detection channel 130. In contrast, the clock signal CLL_A is generated only in a portion corresponding to the detection channels 95 that correspond to the odd-numbered columns and is not generated in a portion corresponding to the non-detection channels 130 that correspond to the even-numbered columns. That is, the generation of the clock signal CLL_A pauses in the portion.

In the example in FIG. 46, the unit time T is the period required to output the digital signals DS(C) corresponding to two adjacent columns. As described above, since the generation of the clock signal CLL_A pauses in a portion corresponding to the even-numbered non-detection channel 130 of the two adjacent columns, the number of pulses per unit time T is ½ of that in the clock signal CLN_A.

Figure 47:
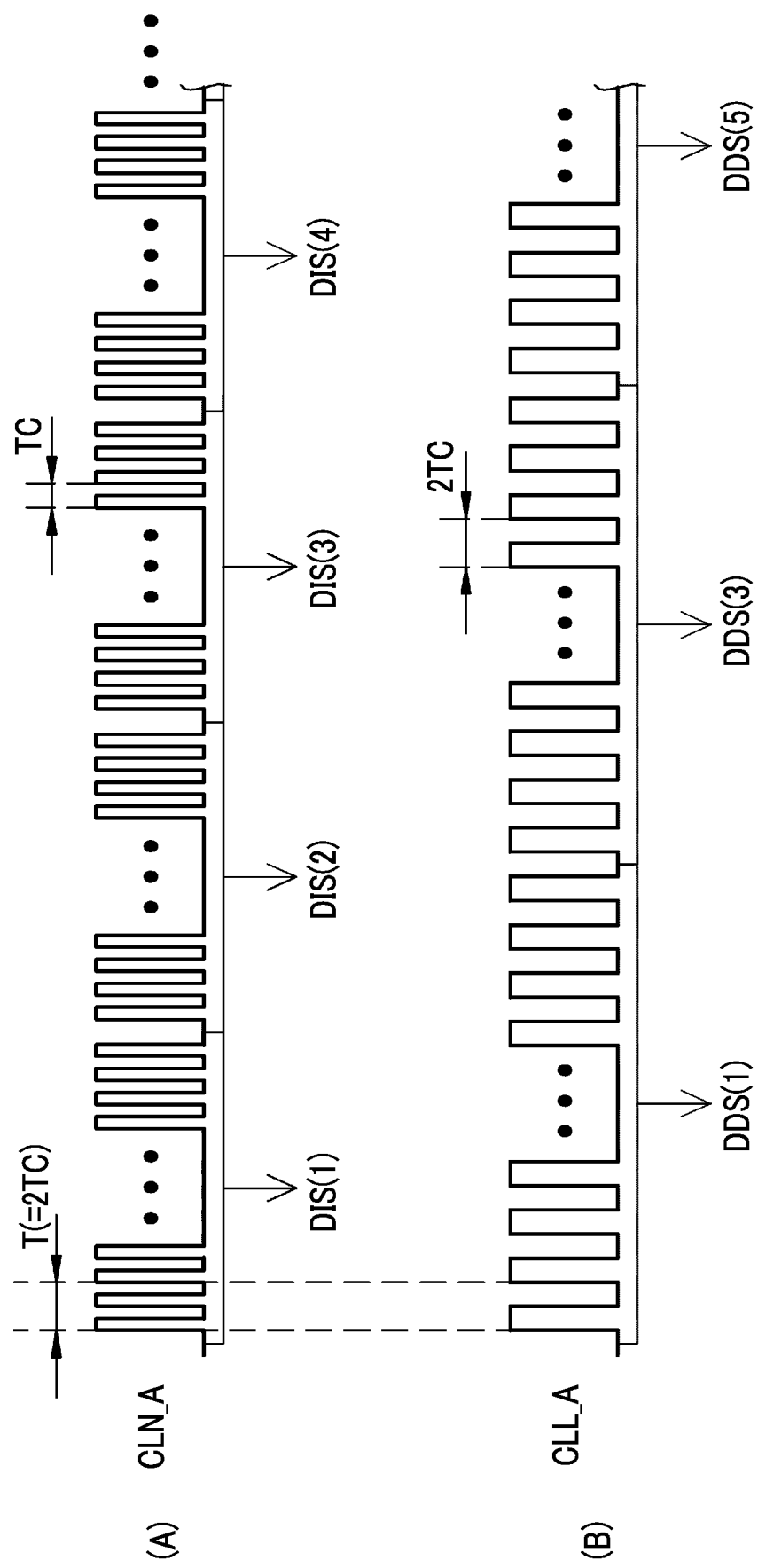
FIG. 47 is a diagram illustrating a second method that reduces the number of pulses per unit time in the clock signal of the ADC in the AED operation to be less than that in the image reading operation. (A) of FIG. 47 illustrates the clock signal in the image reading operation and (B) of FIG. 47 illustrates the clock signal in the AED operation.

FIG. 47 illustrates the second method for setting the number of pulses per unit time in the clock signal of the ADC 77 to NPUL_A that is ½ of NPUN_A in the image reading operation. Similarly to FIG. 46, (A) of FIG. 47 illustrates a clock signal CLN_A in the image reading operation and (B) of FIG. 47 illustrates a clock signal CLL_A in the AED operation. The clock signal CLN_A in the image reading operation is exactly the same as that in FIG. 46. In contrast, the pause period illustrated in (B) FIG. 46 is not provided in the clock signal CLL_A in the AED operation and the period of the clock signal CLL_A is 2TC that is twice as long as the period TC of the clock signal CLN_A.

In the example illustrated in FIG. 47, the unit time T is the period 2TC of the clock signal CLL_A. In the period 2TC, while the number of pulses in the clock signal CLN_A is two, the number of pulses in the clock signal CLL_A is one. Therefore, the number of pulses per unit time T in the clock signal CLN_A is ½ of that in the clock signal CLN_A, similarly to FIG. 46.

Figure 48:
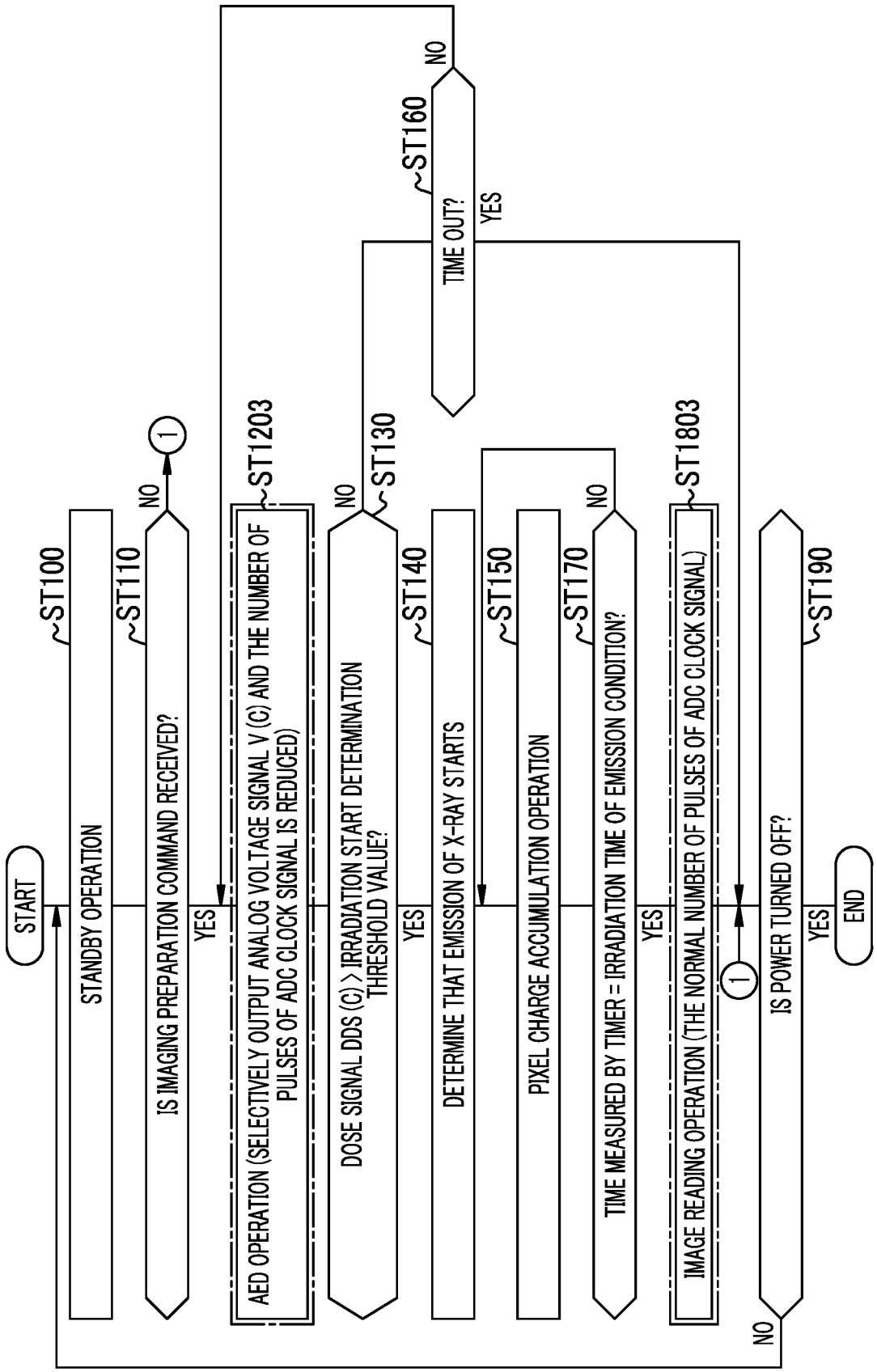
FIG. 48 is a flowchart illustrating the procedure of the operation of an electronic cassette according to the (3-1)-th embodiment.

FIG. 48 is a flowchart illustrating the procedure of the operation of the electronic cassette according to the (3-1)-th embodiment. The flowchart differs from the flowchart illustrated in FIG. 17 in the (1-1)-th embodiment in Steps ST1203 and ST1803 surrounded by a one-dot chain line. Hereinafter, only the difference will be described.

In Step ST1203, in the AED operation, the analog voltage signals V(C) from the detection CAs 132 are selectively output to the ADC 77 and the ADC 77 performs only the AD conversion process for the selectively output analog voltage signal V(C). Then, the number of pulses per unit time T in the clock signal of the ADC 77 is reduced to be less than that in the image reading operation (irradiation start detection step). In Step ST1803, in the image reading operation, the number of pulses per unit time T in the clock signal of the ADC 77 is set to the normal number of pulses (NPUN_A) (image reading step).

As such, since the number of pulses per unit time T in the clock signal of the ADC 77 in the AED operation is less than that in the image reading operation, it is possible to reduce the consumption of power required for driving the ADC 77 in the AED operation and thus to reduce the power consumption of the signal processing circuit 51 in the AED operation. Therefore, similarly to the first and second inventions, the battery 65 lasts longer than that in the related art. As a result, the number of times the battery 65 is charged is reduced and thus it is possible to improve imaging efficiency.

In FIG. 44, for convenience of explanation, half of the columns in one area AR are set as the detection channels 95. However, as described in the (1-8)-th embodiment, the detection channels 95 may be set by any method.

(3-2)-th Embodiment

FIG. 49 illustrates a (3-2)-th embodiment. In the (3-1)-th embodiment, the MUX 135 having a function of selecting the analog voltage signals V(C) from some of a plurality of connected CAs 60 is used. However, in a case in which the MUX 135 having the above-mentioned function is not present as a general-purpose product, it takes a lot of time and effort to implement the function and it costs to implement the function. For example, the MUX 76 that has only the function of sequentially selecting the columns one by one is modified into the MUX 135 or the MUX 135 with the above functions is custom-made. Therefore, in the (3-2)-th embodiment illustrated in FIG. 49, the analog voltage signals V(C) from some CAs are selectively output to the ADC 77 while a general MUX 76 is used.

FIG. 49 illustrates a circuit configuration of the detection channel 95 in the (3-2)-th embodiment. The detection channel 95 is divided into a first path 140 that is connected to the MUX 76 and a second path 141 that is connected to the ADC 77 without passing through the MUX 76 in a stage behind the CDS 61. The first path 140 is a path that outputs the analog voltage signal V(C) from the detection CA 132 to the ADC 77 through the MUX 76. In contrast, the second path 141 is a path that outputs the analog voltage signal V(C) to the ADC 77 without passing through the MUX 76.

A switch 142 is connected to the detection channel 95, the first path 140, and the second path 141. The control unit 54 controls the driving of the switch 142 to switch the path connected to the detection channel 95 between the first path 140 and the second path 141.

FIG. 49A illustrates a case in which the AED operation is performed and FIG. 49B illustrates a case in which the image reading operation is performed. That is, the second path 141 is selected by the switch 142 in the AED operation and the first path 140 is selected by the switch 142 in the image reading operation.

As such, the detection channel 95 is divided into the first path 140 that outputs the analog voltage signal V(C) from the detection CA 132 to the ADC 77 through the MUX 76 and the second path 141 that outputs the analog voltage signal V(C) from the detection CA 132 to the ADC 77 without passing through the MUX 76. Therefore, in the AED operation, the switch 142 is controlled such that the second path 141 is selected. Therefore, it is not necessary to prepare the special MUX 135 described in the (3-1)-th embodiment illustrated in FIG. 44 and it is possible to save time and costs.

As described above, each embodiment of the third invention may be combined with each embodiment of the first invention and the second invention. For example, as in the second invention, the first invention may be applied such that the control unit 54 periodically switches the power supply state of the ADC 77 and the MUX 76 which form the block BL between the first state and the second state, as illustrated in FIG. 14 in the (1-1)-th embodiment. The first state and the second state are defined as described at the end of the second invention.

As in the second invention, the switching patterns of power supply to the ADC 77 and the block BL in the third invention and the first invention may be combined as follows. First, in a case in which there are two or more blocks BL including the MUX 76 and the ADC 77 whose power supply state is periodically switched as illustrated in, for example, FIG. 14 of the (1-1)-th embodiment, the control unit 54 may shift the switching timing of the power supply state of at least two of the two or more blocks BL.

In addition, the control unit 54 may shift the switching timing of the power supply state for each of a plurality of groups to which two or more blocks BL belong, as illustrated in, for example, FIG. 14 of the (1-1)-th embodiment. In this case, it is preferable that at least one block BL is disposed between two blocks BL belonging to the same group. Alternatively, as illustrated in, for example, FIG. 18 of the (1-2)-th embodiment, the switching timing of the power supply state of all of the two or more blocks BL may be shifted.

For example, as illustrated in FIG. 21 of the (1-5)-th embodiment, in a case in which there are a plurality of blocks BL including the MUX 76 to which some CAs are not connected, control may be performed such that at least one of the blocks BL is always in the second state.

As in the (1-12)-th embodiment illustrated in FIGS. 35 to 37, leak charge correction and temperature drift correction may be performed for the dose signal DDS(C).

For example, in a case in which the (1-12)-th embodiment illustrated in FIGS. 35 to 37 is applied to the configuration of the (3-1)-th embodiment illustrated in FIG. 44, some CAs that selectively output the analog voltage signal V(C) to the ADC 77 are the detection CA 132 connected to the detection channel 95 illustrated in FIG. 44 and the CA 60 connected to the reference channel 120 illustrated in FIG. 37. That is, in the (3-1)-th and (3-2)-th embodiments, only the detection CA 132 has described as some CAs that selectively output the analog voltage signal V(C) to the ADC 77. However, the invention is not limited thereto. The CA 60 connected to the reference channel 120 is also included.

In addition, the (1-8)-th embodiment illustrated in FIGS. 25 to 27 in which the detection channel 95 that is the signal line 42 to which the detection pixel 90 used for the AED operation is connected is set, the (1-9)-th embodiment illustrated in FIGS. 28 to 31 in which the detection pixel 90X used only for the AED operation is provided, the (1-10)-th embodiment illustrated in FIG. 32 in which the setting of the detection pixel 90 can be changed, the (1-11)-th embodiment illustrated in FIGS. 33 and 34 in which the operation of the CDS 61 in the AED operation is simplified, and the (1-13)-th embodiment illustrated in FIG. 38 in which the digital signal transmission I/F is switched may be combined with each other.

Further, the (2-1)-th to (2-3)-th embodiments of the second invention illustrated in FIGS. 39 to 43 may be applied to change at least one of the non-selected CAs other than some CAs that selectively output the analog voltage signal V(C) to the ADC 77 to the power saving state in which power supplied to the non-selected CAs in the AED operation is lower than normal power in the image reading operation.

Here, the non-selected CA is the non-detection CA 131 in a case in which the (1-12)-th embodiment illustrated in FIGS. 35 to 37 is not applied and is the non-detection CA 131 other than the CA 60 connected to the reference channel 120 in a case in which the (1-12)-th embodiment is applied.

In a case in which the (2-3)-th embodiment is applied, not only the non-detection CA 131 but also at least one of the detection CAs 132 (including the CA 60 connected to the reference channel 120 in a case in which the (1-12)-th embodiment is applied) is driven in a low power state in which power lower than the normal power PN_C and is greater than 0 is supplied. Therefore, it is possible to further reduce the power consumption of the signal processing circuit 51 in the AED operation.

4. Fourth Invention

An object of a fourth invention illustrated in FIGS. 50 to 58 which will be described below is to solve the problems occurring in a case in which the AED operation is performed while the power supply state of a plurality of ADCs 77 and a plurality of blocks BL1 to BL16 according to the first invention is switched. In the fourth invention, the control unit 54 switches each of the plurality of blocks BL1 to BL16 from the second state to the first state a predetermined time, which is required to stably operate, for example, the ADC 77 forming the block BL, before the start timing of charge reading in the AED operation.

In the fourth invention, similarly to the second and third inventions, for example, the X-ray imaging system 10 and the electronic cassette 16 have the same basic configuration as those in the first invention. In addition, the patterns described in the (1-1)-th to (1-7)-th embodiments can be applied to the switching pattern of the power supply state of the ADC 77. Further, the fourth invention may be combined with other embodiments (the (1-8)-th to (1-13)-th embodiments) of the first invention, the (2-1)-th to (2-3)-th embodiments of the second invention, and the (3-1)-th and (3-2)-th embodiments of the third invention. Hereinafter, the same components as those in the first to third inventions are denoted by the same reference numerals and the description thereof will not be repeated. The difference from the first to third inventions will be mainly described.

(4-1)-th Embodiment

Figure 50A:
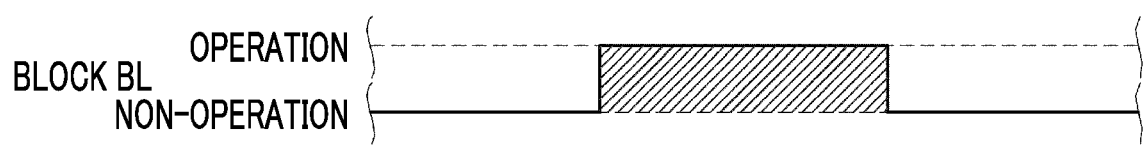
FIG. 50A is a diagram illustrating the power supply state of a block in a case in which the reading of charge starts immediately after the block is switched from a non-operating state to an operating state.
Figure 50B:
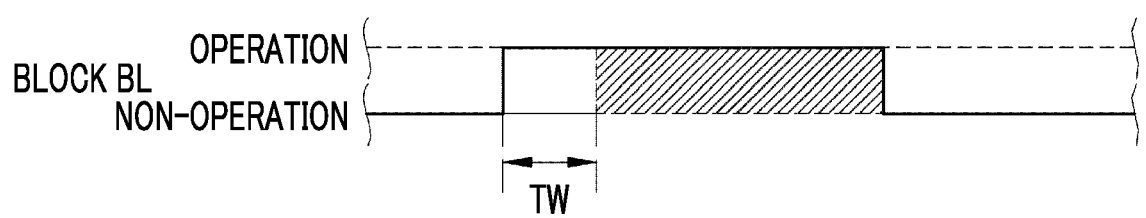
FIG. 50B is a diagram illustrating the power supply state of a block in a case in which the block is switched from the non-operating state to the operating state a predetermined time before the timing when the reading of charge starts.
Figure 51:
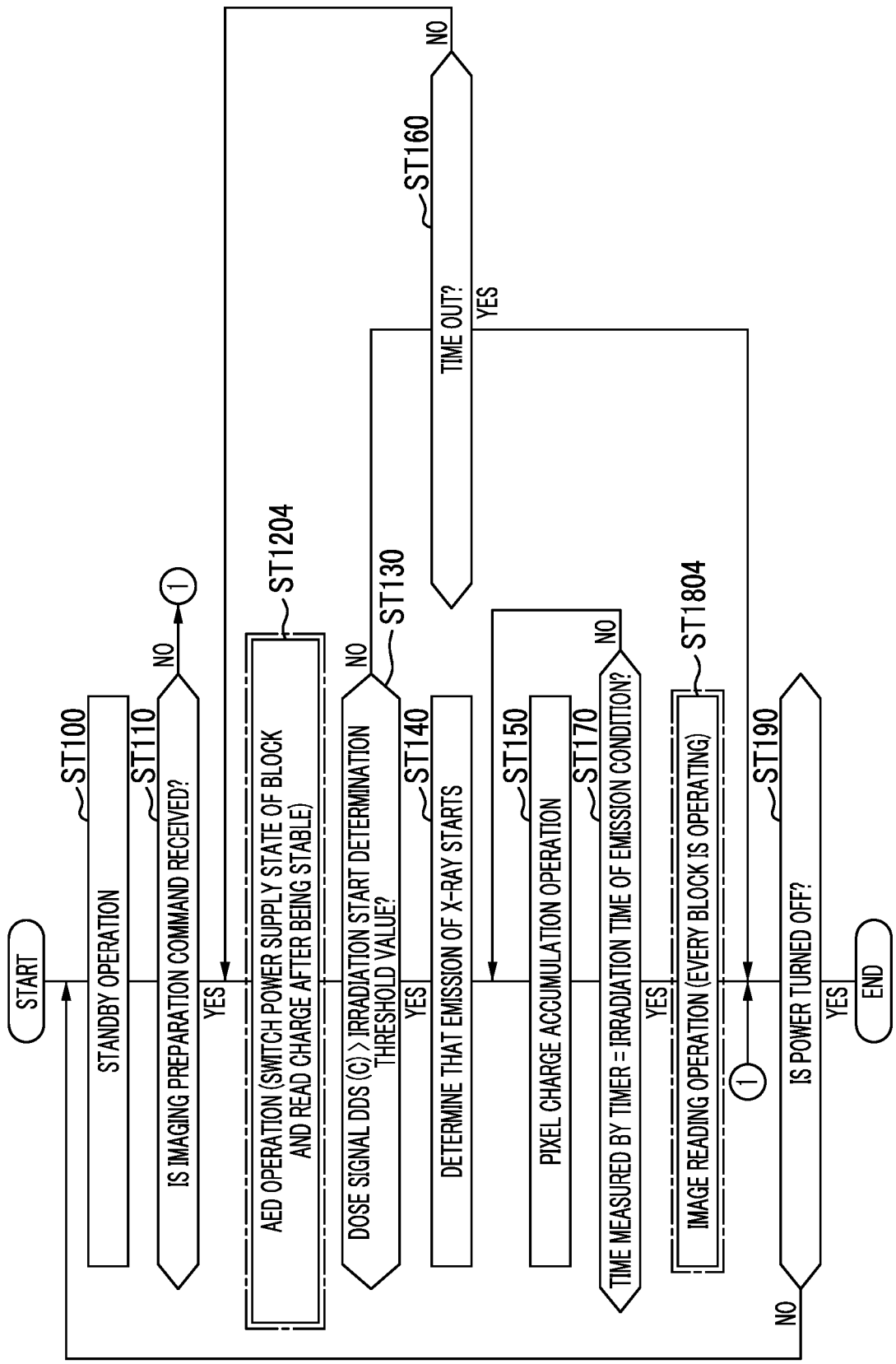
FIG. 51 is a flowchart illustrating the procedure of the operation of an electronic cassette according to a (4-1)-th embodiment.

FIGS. 50 and 51 illustrate a (4-1)-th embodiment. In the (4-1)-th embodiment, similarly to the (2-1)-th and (3-1)-th embodiments, for example, a configuration including the detection pixel 90X1 illustrated in FIG. 29 or the detection pixel 90X2 illustrated in FIG. 30 in the (1-9)-th embodiment will be described. However, the configuration is not limited thereto.

FIG. 50 illustrates the power supply state of a certain block BL. A hatched portion is the period for which charge that is the source of the dose signal DDS(C) is read. Specifically, for the period, a series of operations in which the CA 60 reads charge through the signal line 42, the MUX 76 sequentially selects the CA 60 and outputs the analog voltage signal V(C) based on the charge to the ADC 77, and the ADC 77 converts the analog voltage signal V(C) into the dose signal DDS(C) and outputs the dose signal DDS(C) is performed.

Here, the operation of the block BL becomes unstable due to, for example, the influence of temperature drift immediately after the block BL is switched from the non-operating state which is the second state to the operating state which is the first state. The reliability of the dose signal DDS(C) output while the operation is unstable is significantly reduced. Therefore, there is a concern that the reliability of the determination of whether the emission of X-rays has been started will not be maintained.

FIG. 50A illustrates an example in which the reading of charge starts immediately after the block BL is switched from the non-operating state to the operating state. As such, in a case in which there is not enough time between the switching of the block BL from the non-operating state to the operating state and the timing when the reading of charge starts, the risk that the start of the emission of X-rays will be erroneously determined increases according to the dose signal DDS(C) output while the operation of the block BL is unstable.

Therefore, as illustrated in FIG. 50B, the block BL is switched from the non-operating state to the operating state a time TW before the timing when the reading of charge starts. The time TW is the time required to stably operate the block BL.

FIG. 51 is a flowchart illustrating the procedure of the operation of the electronic cassette according to the (4-1)-th embodiment. The flowchart differs from the flowchart illustrated in FIG. 17 of the (1-1)-th embodiment in Steps ST1204 and ST1804 surrounded by a one-dot chain line. Hereinafter, only the difference will be described.

In Step ST1204, in the AED operation, the control unit 54 switches the power supply state of the block BL. Then, the block BL is switched from the non-operating state to the operating state the time TW before the timing when the reading of charge starts (irradiation start detection step). Further, in Step ST1804, in the image reading operation, all of the blocks BL are switched to the operating state (image reading step).

Then, as illustrated in FIG. 50A, the dose signal DDS(C) is not output while the operation of the block BL is unstable and it is possible to reduce the concern that the start of the emission of X-rays will be erroneously determined.

Figure 52:
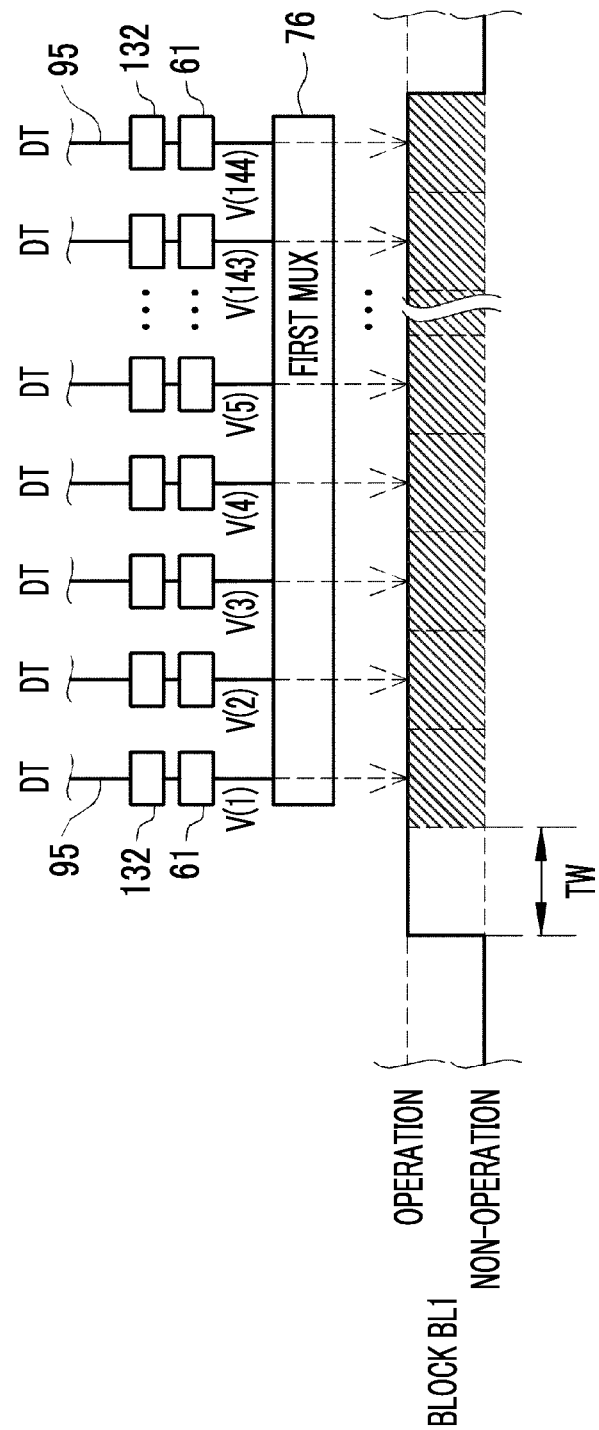
FIG. 52 is a diagram illustrating in detail the period for which charge is read in a case in which the signal lines in all of the areas that the blocks are in charge of are the detection channels.
Figure 53:
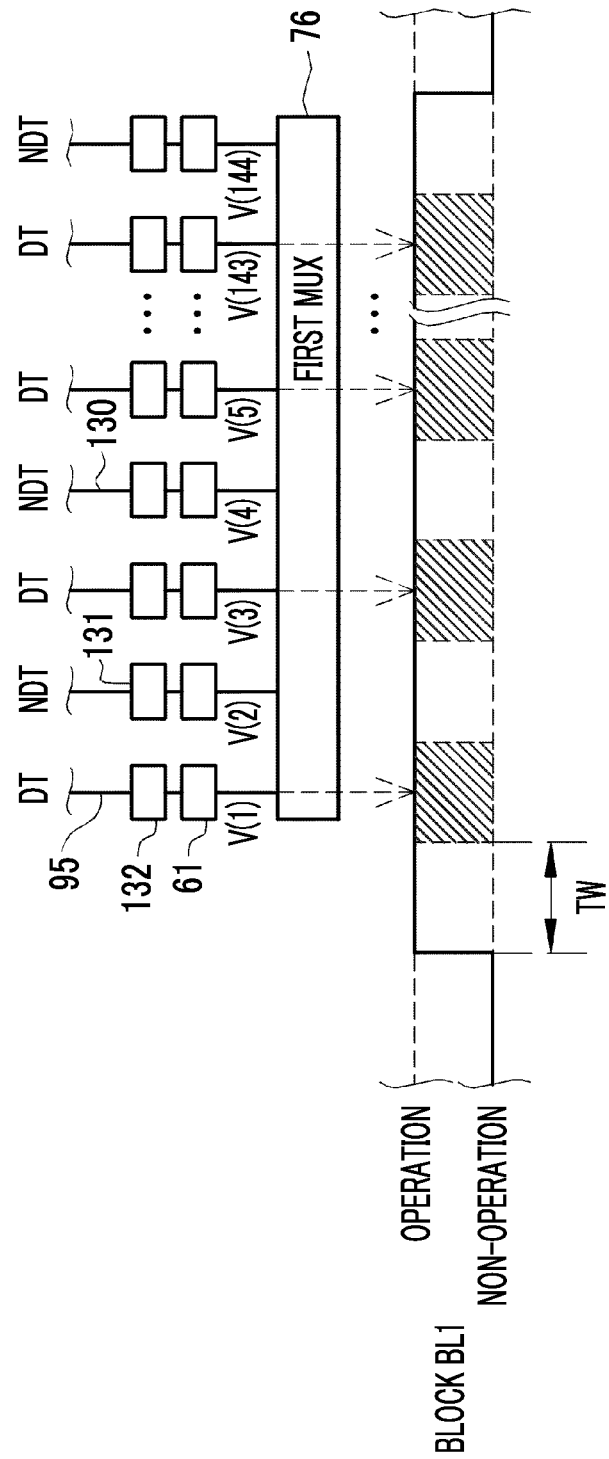
FIG. 53 is a diagram illustrating in detail the period for which charge is read in a case in the odd-numbered columns are the detection channels and the MUX is a general MUX having only a function of sequentially selecting the detection channels one by one.
Figure 54:
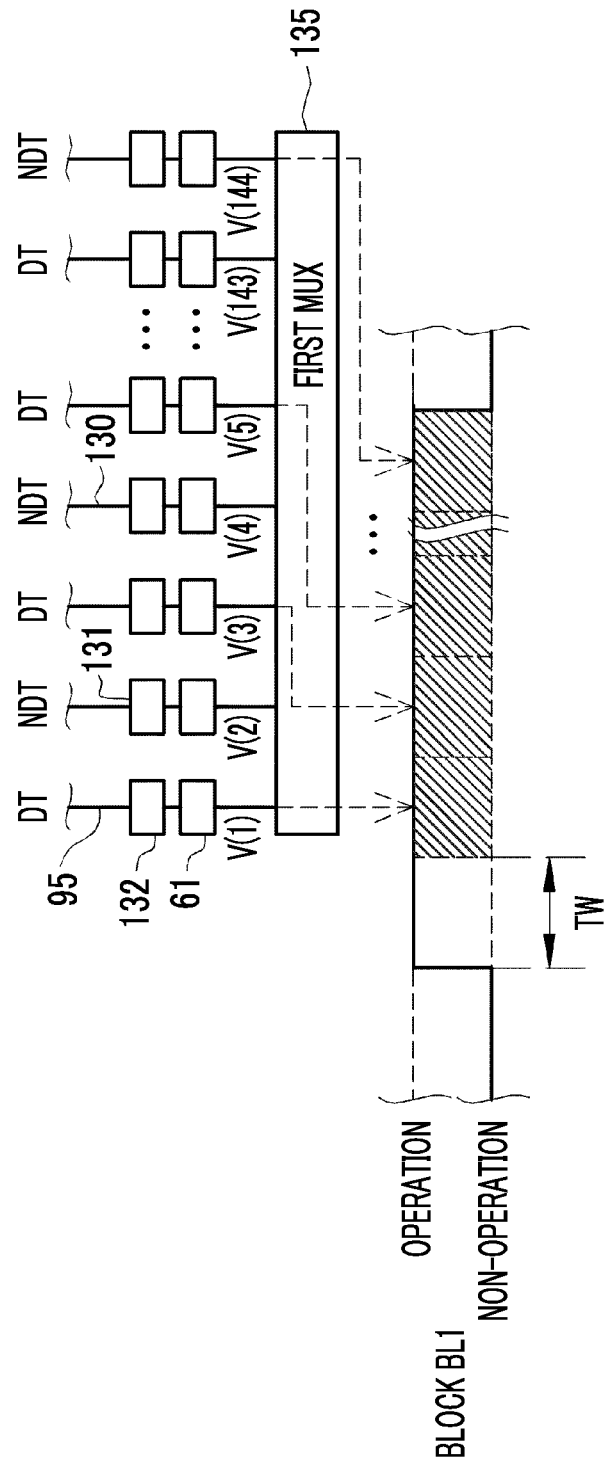
FIG. 54 is a diagram illustrating in detail the period for which charge is read in a case in the odd-numbered columns are the detection channels and the MUX has a function of selecting only the analog voltage signal from the detection CA of the detection channel.

There are three variations illustrated in FIGS. 52 to 54 in the period for which charge is read. The period is hatched in FIGS. 52 to 54. FIGS. 52 to 54 illustrate the block BL1 that is in charge of the area AR1 corresponding to the first to 144th columns, similarly to FIGS. 9 and 44.

First, FIG. 52 illustrates a case in which all of the signal lines 42 in the area AR1 that the blocks BL1 is in charge of are the detection channels 95, as represented by alphabets DT (see FIG. 44). In this case, the period for which charge is read is the period for which the dose signals DDS(1) to DDS(144) based on the analog voltage signals V(1) to V(144) from the detection CAs 132 of the detection channels 95 are output.

FIG. 53 illustrates a case in which the odd-numbered columns are the detection channels 95 and the MUX is not the MUX 135 having a function of selecting the analog voltage signals V(C) from the detection CAs 132 of the detection channels 95, but is the general MUX 76 having only the function of sequentially selecting the columns one by one, similarly to the (3-1)-th embodiment illustrated in FIG. 44. In this case, the period for which charge is read is the period for which the dose signals DDS(1), DDS(3), DDS(5), . . . , DDS(144) based on the analog voltage signals V(1), V(3), V(5), . . . , V(143) from the detection CAs 132 of the detection channels 95 corresponding to the odd-numbered columns are output. That is, in this case, the period for which charge is read is intermittent.

FIG. 54 illustrates a case in which the odd-numbered columns are the detection channels 95 as in FIG. 52 and the MUX is not the MUX 76, but is the MUX 135. In this case, the period for which charge is read is the sum of the periods for which the dose signals DDS(1), DDS(3), DDS(5), . . . , DDS(144) based on the analog voltage signals V(1), V(3), V(5), . . . , V(143) from the detection CAs 132 of the detection channels 95 corresponding to the odd-numbered columns are output. Since the period for which charge is read is not intermittent unlike FIG. 53, the simple appearance is the same as that in FIG. 52. However, while the MUX 76 sequentially selects the analog voltage signals V(C) corresponding to the columns one by one in FIG. 52, the MUX 135 selects the analog voltage signal V(C) for every other column in FIG. 54.

(4-2)-th Embodiment

Figure 55:
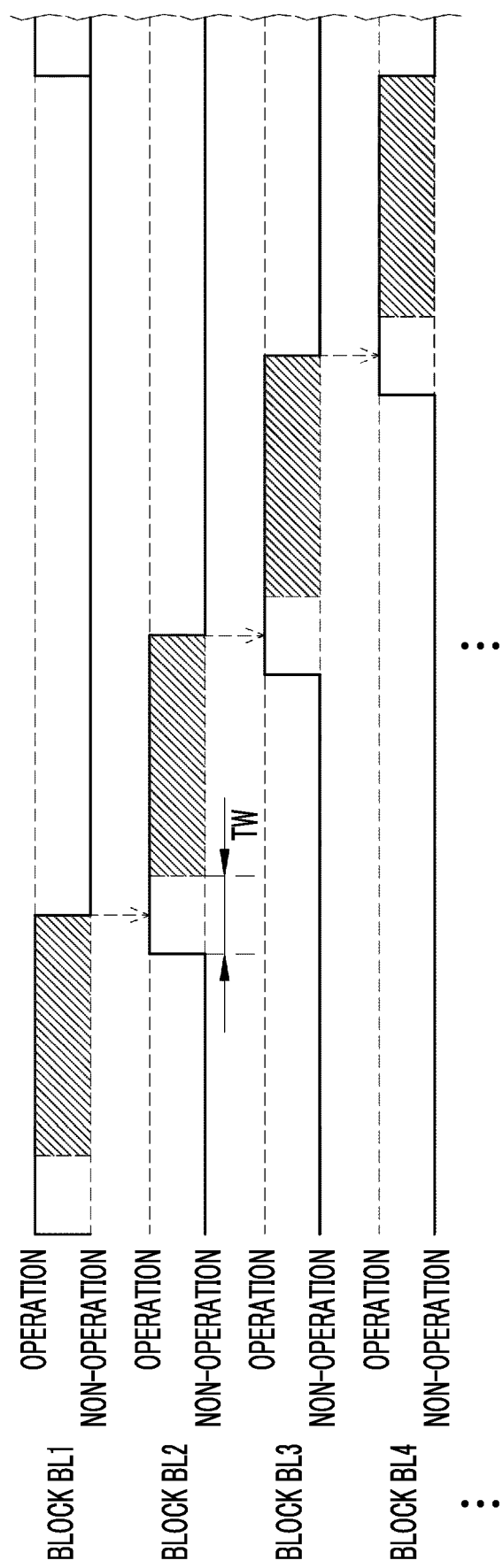
FIG. 55 is a diagram illustrating an example in which each block is switched from the operating state to the non-operating state before the reading of charge in each block starts.
Figure 56:
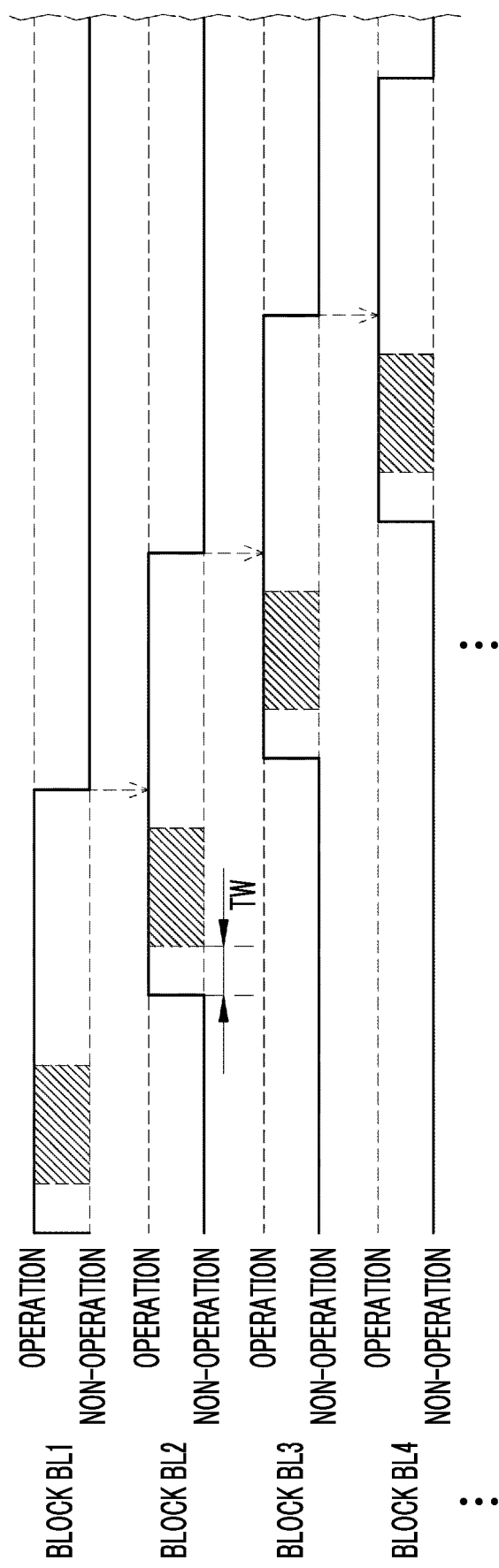
FIG. 56 is a diagram illustrating an example in which each block is switched from the operating state to the non-operating state after the reading of charge in each block ends.
Figure 57:
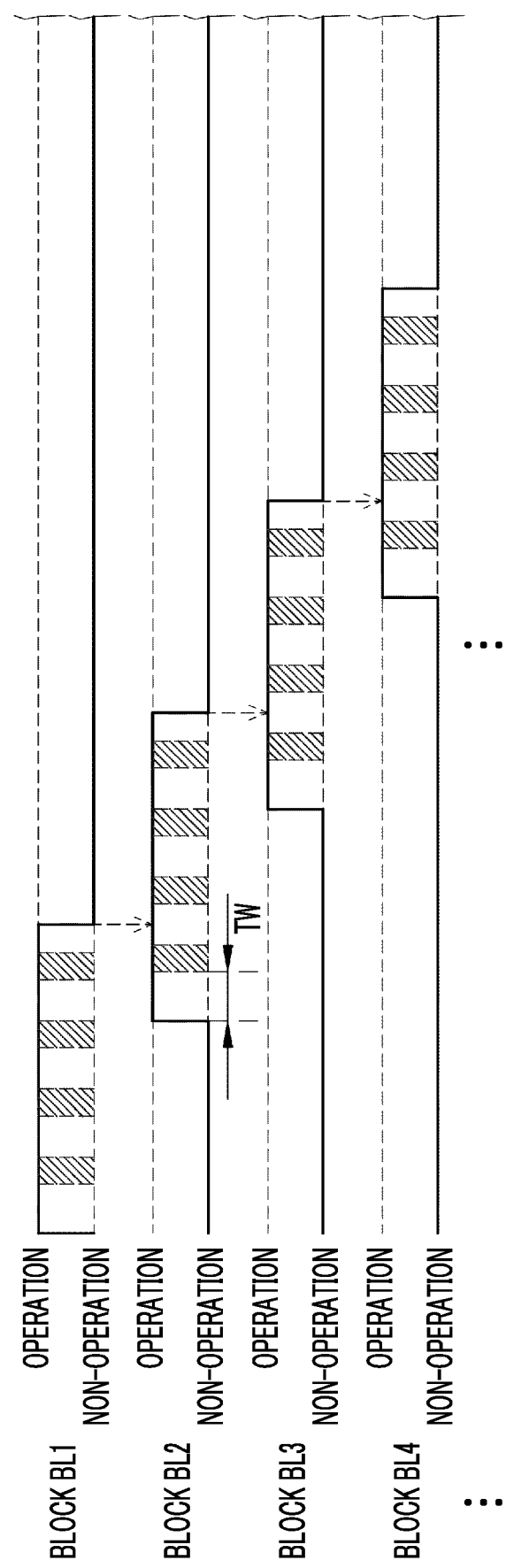
FIG. 57 is a diagram illustrating an example in which each block is switched from the operating state to the non-operating state between the intermittent periods for which charge is read in each block.

FIGS. 55 to 57 illustrate a (4-2)-th embodiment. In the (4-1)-th embodiment, the timing when the block BL is switched from the non-operating state to the operating state with respect to the timing when the reading of charge starts is defined. However, in the (4-2)-th embodiment, the timing when the block BL is switched from the operating state to the non-operating state is defined.

In a case in which a certain block BL is switched from the operating state to the non-operating state and charge is being read in another block BL, there is a concern that, for example, switching noise generated by the switching of the block BL from the operating state to the non-operating state will be mixed with charge in another block BL. Therefore, in the (4-2)-th embodiment, a certain block BL is switched from the operating state to the non-operating state at a timing that does not overlap the timing when charge is read in another block BL.

FIGS. 55 to 57 illustrate a case in which the power supply state of each of the blocks BL1 to BL16 (the block BL5 and the subsequent blocks are not illustrated) is periodically switched and the timing when the power supply state of each of the blocks BL1 to BL16 is switched is shifted, similarly to FIG. 14 of the (1-1)-th embodiment or FIG. 18 of the (1-2)-th embodiment. FIGS. 55 and 56 illustrate a case in which the period for which charge is read is a variation of FIG. 52 or FIG. 54 and FIG. 57 illustrates a case in which the period for which charge is read is a variation of FIG. 53.

FIG. 55 illustrates an example in which each of the blocks BL1 to BL16 is switched from the operating state to the non-operating state at the timing before reading of charge from the detection CAs 132 in each of the blocks BL1 to BL16 starts, specifically, for the time TW, as represented by a dashed arrow. Specifically, in FIG. 55, the control unit 54 switches the block BL1 from the operating state to the non-operating state while the block BL2 is operating and switches the block BL2 from the operating state to the non-operating state while the block BL3 is operating. In addition, the control unit 54 switches the block BL3 from the operating state to the non-operating state while the block BL4 is operating.

FIG. 56 illustrates an example in which each of the blocks BL1 to BL16 is switched from the operating state to the non-operating state at the timing after the reading of charge from the detection CAs 132 in each of the blocks BL1 to BL16 ends. Specifically, in FIG. 56, the control unit 54 switches the block BL1 from the operating state to the non-operating state after the reading of charge in the block BL2 ends and switches the block BL2 from the operating state to the non-operating state after the reading of charge in the block BL3 ends. In addition, the control unit 54 switches the block BL3 from the operating state to the non-operating state after the reading of charge in the block BL4 ends.

FIG. 57 illustrates an example in which each of the blocks BL1 to BL16 is switched from the operating state to the non-operating state between the intermittent periods for which charge is read in the blocks BL1 to BL16. Specifically, in FIG. 57, the control unit 54 switches the block BL1 from the operating state to the non-operating state between the intermittent periods for which charge is read in the block BL2 and switches the block BL2 from the operating state to the non-operating state between the intermittent periods for which charge is read in the block BL3. Then, the control unit 54 switches the block BL3 from the operating state to the non-operating state between the intermittent periods for which charge is read in the block BL4.

As such, in a case in which the block BL is switched from the operating state to the non-operating state at a timing that does not overlap the timing when charge is read in another block BL, there is no concern that, for example, switching noise generated by the switching of the block BL from the operating state to the non-operating state will be mixed with charge in another block BL.

Among the examples illustrated in FIGS. 55 to 57, the example illustrated in FIG. 55 in which each of the blocks BL1 to BL16 is switched from the operating state to the non-operating state before the reading of charge in each of the blocks BL1 to BL16 starts is most preferable in terms of power saving.

(4-3)-th Embodiment

Figure 58:
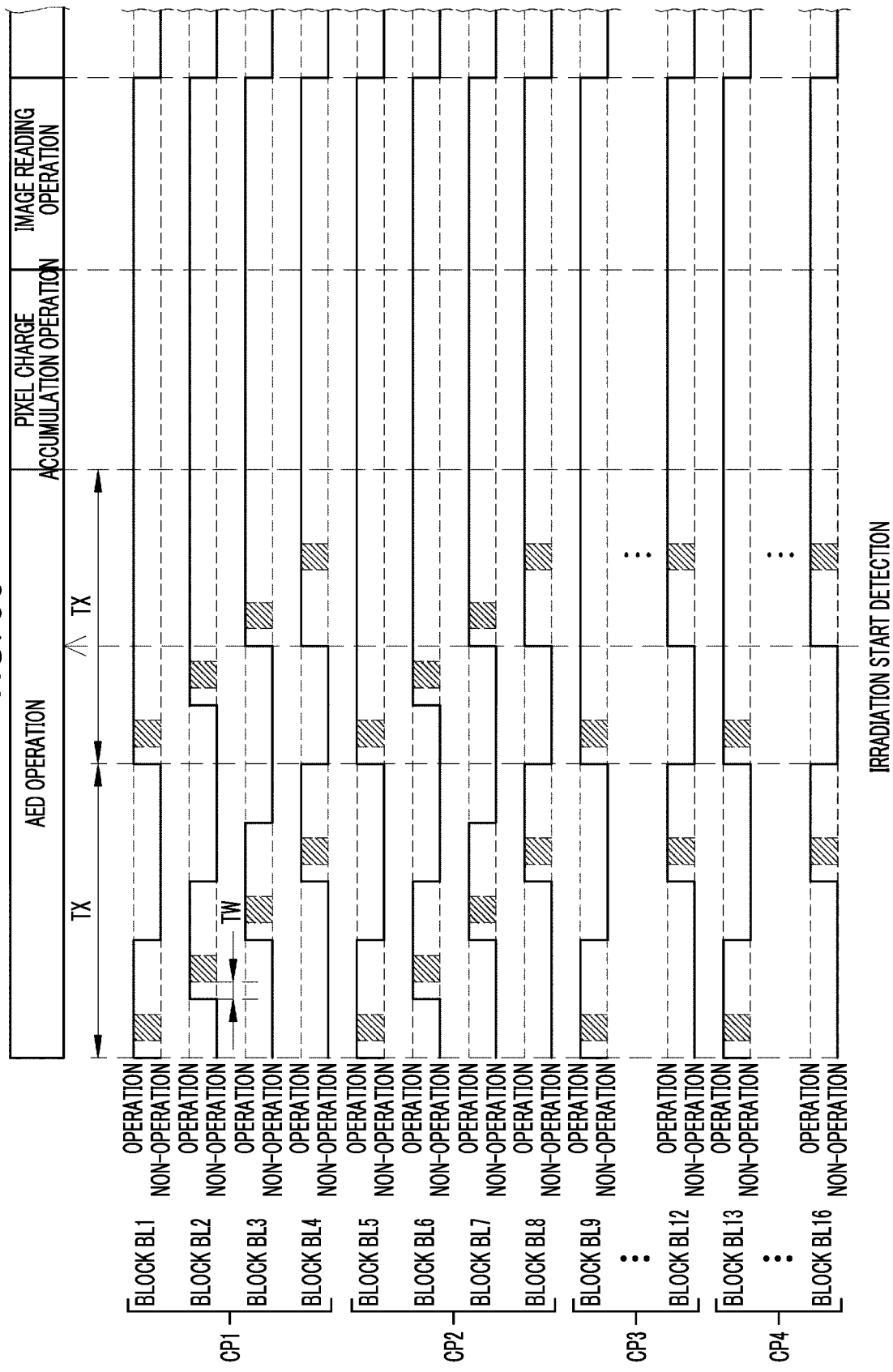
FIG. 58 is a diagram illustrating a (4-3)-th embodiment in which all of the blocks are changed to the operating state until the image reading operation starts after the start of the emission of X-rays is detected in the AED operation.

FIG. 58 illustrates a (4-3)-th embodiment. As illustrated in FIG. 35 of the (1-12)-th embodiment, in a case in which the power supply state of each block BL is switched in the AED operation, the temperature distribution in the block BL is biased. In a case in which the bias of the temperature distribution is not removed until the image reading operation for obtaining the X-ray image provided for diagnosis, a temperature drift occurs in the image signal DIS(C) and the quality of the X-ray image is degraded. Therefore, in the (4-3)-th embodiment, the control unit 54 switches all of the blocks BL to the operating state until the image reading operation starts after the start of the emission of X-rays is detected in the AED operation.

In FIG. 58, all of the blocks BL1 to BL16 are switched to the operating state at the timing when the start of the emission of X-rays is detected in the AED operation. Specifically, in FIG. 58, the control unit 54 switches the blocks BL (blocks BL3, BL4, BL7, BL8, BL11, BL12, BL15, and BL16) in the non-operating state in a case in which the start of the emission of X-rays is detected to the operating state. In contrast, the control unit 54 maintains the blocks BL (for example, the blocks BL1 and BL2 other than the above) in the operating state in a case in which the start of the emission of X-rays is detected in the operating state.

In FIG. 58, since all of the blocks BL1 to BL16 are switched to the operating state at the timing when the start of the emission of X-rays is detected in the AED operation, all of the blocks BL1 to BL16 are switched to the operating state for a reading period TX of the dose signal DDS(C) where one cycle of the switching of all of the blocks BL1 to BL16 ends after the start of the emission of X-rays is detected.

As such, since all of the blocks BL are switched to the operating state until the image reading operation starts after the start of the emission of X-rays is detected in the AED operation, it is highly possible that the bias of the temperature distribution in the block BL caused by the switching of the power supply state of each block BL in the AED operation has been removed in the image reading operation. Therefore, a temperature drift does not occur in the image signal DIS(C) due to the bias of the temperature distribution in the block BL and it is possible to obtain a high-quality X-ray image.

In addition, since all of the blocks BL1 to BL16 are switched to the operating state for the reading period TX of the dose signal DDS(C) where one cycle of the switching of all of the blocks BL1 to BL16 ends after the start of the emission of X-rays is detected, it is possible to secure the time sufficient to remove the bias of the temperature distribution in the block BL until the image reading operation starts.

Further, all of the blocks BL1 to BL16 may be switched to the operating state at any timing of the period from the detection of the start of the emission of X-rays in the AED operation to the start of the image reading operation. However, it is preferable that all of the blocks BL1 to BL16 are switched to the operating state at the timing when the start of the emission of X-rays is detected in the AED operation as illustrated in FIG. 58, in order to reliably remove the bias of the temperature distribution in the block BL. The operating state, the non-operating state, the first state, and the second state are defined as described at the end of the second invention.

The time TW required to stably operate the block BL may be substantially equal to or longer than the time required to prepare for the operation of the CA 60, the CDS 61, the MUX 76, and the ADC 77 forming the block BL. The fourth invention also includes the case in which the time TW required to stably operate the block BL is substantially equal to the time required to prepare for the operation of the CA 60, the CDS 61, the MUX 76, and the ADC 77 forming the block BL. That is, the fourth invention also includes a case in which the reading of charge starts immediately after the CA 60, the CDS 61, the MUX 76, and the ADC 77 forming the block BL are ready for operation.

In addition, power supplied to each component of the block BL for the time TW may be changed depending on the temperature of the block BL. For example, in a case in which the temperature of the block BL before the time TW is significantly lower than a target temperature, the control unit 54 supplies relatively high power to each component of the block BL such that the temperature reaches the target temperature in a short time. In contrast, in a case in which the temperature of the block BL before the time TW is lower than the target temperature, but is relatively close to the target temperature and relatively high power is supplied to each component of the block BL, there is a concern that the temperature will exceed the target temperature. Therefore, the control unit 54 operates each component of the block BL with relatively low power.

As described above, each embodiment of the fourth invention may be combined with each embodiment of the first invention, the second invention, and the third invention. For example, as in the second and third inventions, the first invention may be applied such that the control unit 54 periodically switches the power supply state of the ADC 77 and the MUX 76 which form the block BL between the first state and the second state, as illustrated in FIG. 14 in the (1-1)-th embodiment.

As in the second and third inventions, the switching patterns of power supply to the ADC 77 and the block BL in the fourth invention and the first invention may be combined as follows. First, in a case in which there are two or more blocks BL including the MUX 76 and the ADC 77 whose power supply state is periodically switched as illustrated in, for example, FIG. 14 of the (1-1)-th embodiment, the control unit 54 may shift the switching timing of the power supply state of at least two of the two or more blocks BL.

In addition, the control unit 54 may shift the switching timing of the power supply state for each of a plurality of groups to which two or more blocks BL belong, as illustrated in, for example, FIG. 14 of the (1-1)-th embodiment. In this case, it is preferable that at least one block BL is disposed between two blocks BL belonging to the same group. Alternatively, as illustrated in, for example, FIG. 18 of the (1-2)-th embodiment, the switching timing of the power supply state of all of the two or more blocks BL may be shifted.

As illustrated in, for example, FIG. 21 of the (1-5)-th embodiment, in a case in which there are a plurality of blocks BL including the MUX 76 to which only the non-detection CA 131 is connected, at least one of the plurality of blocks BL may be always in the second state.

As in the (1-12)-th embodiment illustrated in FIGS. 35 to 37, leak charge correction and temperature drift correction may be performed for the dose signal DDS(C).

In addition, the (1-8)-th embodiment illustrated in FIGS. 25 to 27 in which the detection channel 95 that is the signal line 42 to which the detection pixel 90 used for the AED operation is connected is set, the (1-9)-th embodiment illustrated in FIGS. 28 to 31 in which the detection pixel 90X used only for the AED operation is provided, the (1-10)-th embodiment illustrated in FIG. 32 in which the setting of the detection pixel 90 can be changed, the (1-11)-th embodiment illustrated in FIGS. 33 and 34 in which the operation of the CDS 61 in the AED operation is simplified, and the (1-13)-th embodiment illustrated in FIG. 38 in which the digital signal transmission I/F is switched may be combined with each other.

Further, the (2-1)-th to (2-3)-th embodiments of the second invention illustrated in FIGS. 39 to 43 may be applied to change at least one of the non-selected CAs other than some CAs that selectively output the analog voltage signal V(C) to the ADC 77 to the power saving state in which power supplied to the non-selected CAs in the AED operation is lower than normal power in the image reading operation.

In addition, the (3-1)-th and (3-2)-th embodiments illustrated in FIGS. 44 to 49 in which the number of pulses per unit time in the clock signal of the ADC 77 is less than that in the image reading operation may be applied.

5. Fifth Invention

In a fifth invention illustrated in FIGS. 59 and 60 which will be described below, the control unit 54 reduces the power supplied to the CA 60 in the AED operation to be lower than that in the image reading operation. In the second invention, at least one of the non-detection CAs 131 is changed to the power saving state in which power supplied to the non-detection CA in the AED operation is lower than the normal power in the image reading operation. However, the fifth invention differs from the second invention in that power supplied to the CAs 60 in the AED operation is lower than that in the image reading operation, without distinguishing between the detection CA 132 and the non-detection CA 131.

In the fifth invention, similarly to the second to fourth inventions, for example, the X-ray imaging system 10 and the electronic cassette 16 have the same basic configuration as those in the first invention. Hereinafter, the same components as those in the first to fourth inventions are denoted by the same reference numerals and the description thereof will not be repeated. The difference from the first to fourth inventions will be mainly described.

Figure 59:
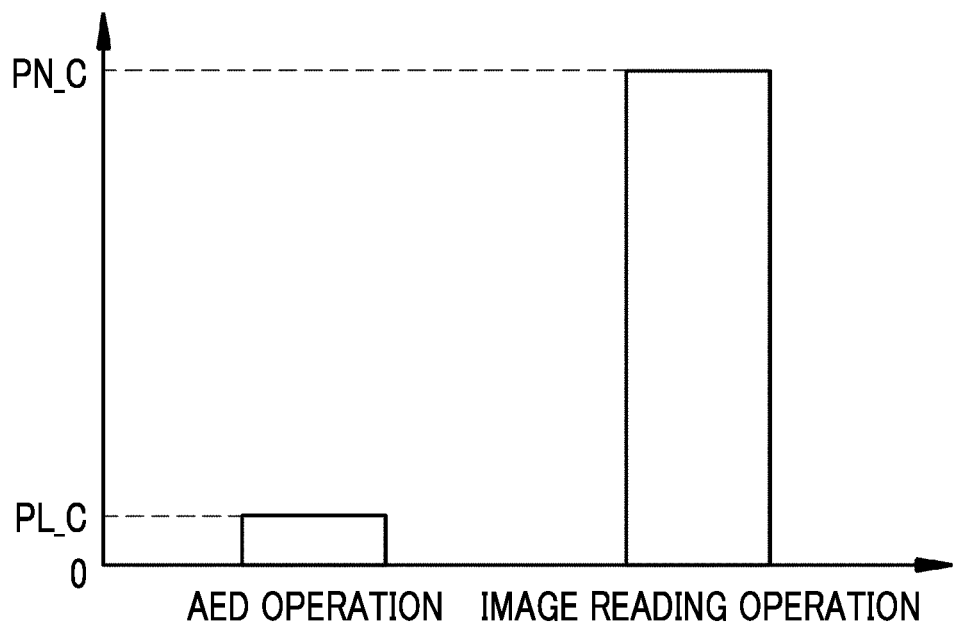
FIG. 59 is a graph illustrating the supply of power to the CA.

As illustrated in FIG. 59, the control unit 54 sets the power P_C supplied to all of the CAs 60 in the image reading operation to normal power PN_C and sets the power P_C supplied to all of the CAs 60 in the AED operation to PL_C that is lower than PN_C.

Figure 60:
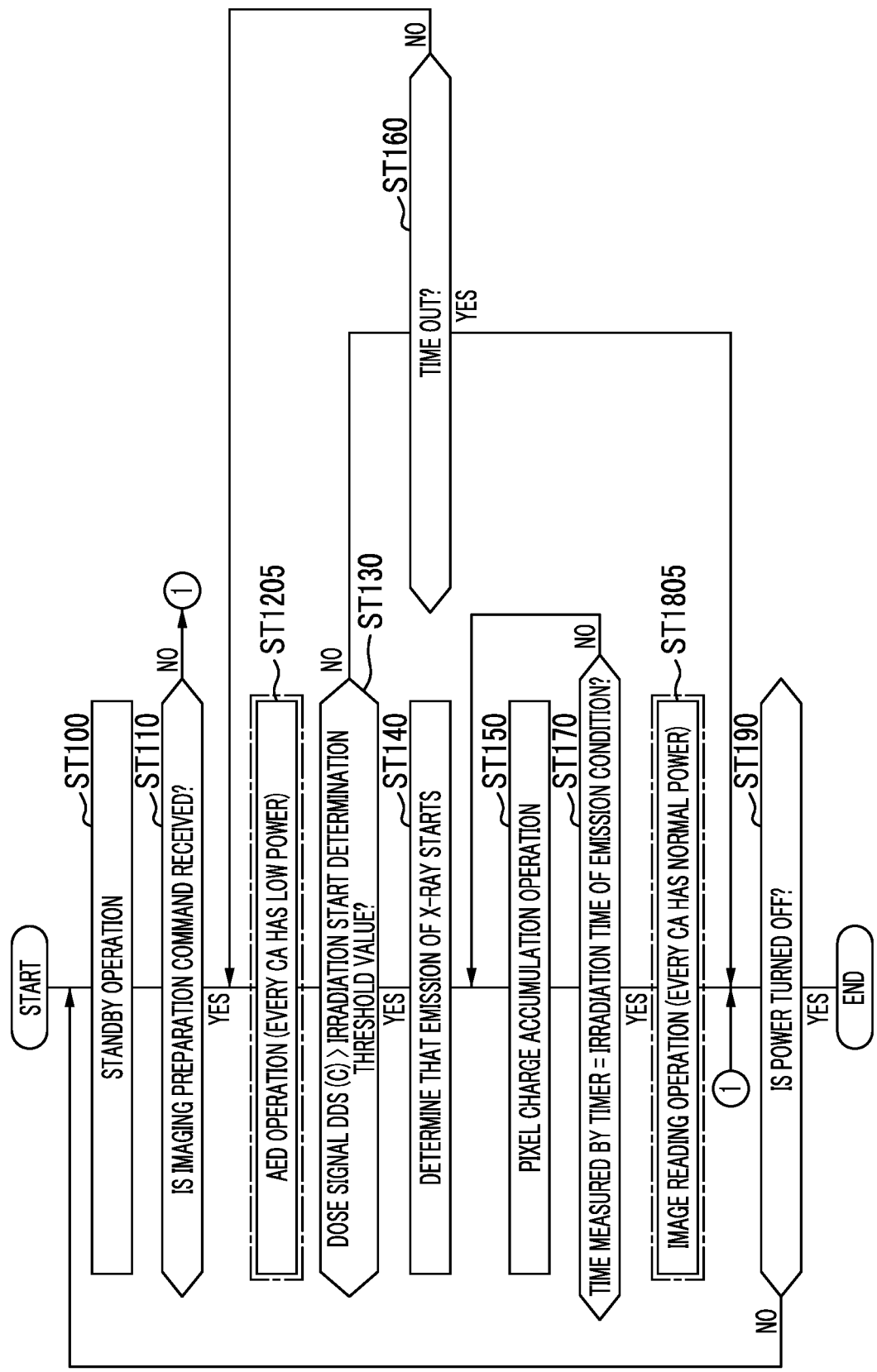
FIG. 60 is a flowchart illustrating the procedure of the operation of an electronic cassette according to a fifth invention.

FIG. 60 is a flowchart illustrating the procedure of the operation of the electronic cassette according to the fifth invention. The flowchart differs from the flowchart illustrated in FIG. 17 of the (1-1)-th embodiment in Steps ST1205 and ST1805 surrounded by a one-dot chain line. Hereinafter, only the difference will be described.

In Step ST1205, in the AED operation, all of the CAs 60 are driven with the low supply power PL_C. In contrast, in the image reading operation of Step ST1805, all of the CAs 60 are driven with the normal power PN_C.

As such, since the power supplied to the CA 60 in the AED operation is lower than that in the image reading operation, it is possible to reduce the power consumption of the signal processing circuit 51 in the AED operation. Therefore, as in the first to third inventions, the battery 65 lasts longer than that in the related art. As a result, the number of times the battery 65 is charged is reduced and thus it is possible to improve imaging efficiency.

It is possible to understand a radiographic image detection device described in the following Supplementary Note 1 and a method for operating a radiographic image detection device described in the following Supplementary Note 2 from the above description.

[Supplementary Note 1]

There is provided a radiographic image detection device comprising: a sensor panel in which pixels that are sensitive to radiation which has been emitted from a radiation generation apparatus and transmitted through a subject and accumulate charge are two-dimensionally arranged and a plurality of signal lines for reading the charge are arranged; a signal processing circuit that reads an analog voltage signal corresponding to the charge from the pixel through the signal line to perform signal processing; a plurality of charge amplifiers which are included in the signal processing circuit and each of which is provided for each signal line, is connected to one end of the signal line, and converts the charge from the pixel into the analog voltage signal; a multiplexer that is included in the signal processing circuit, has a plurality of input terminals to which the plurality of charge amplifiers are connected, sequentially selects the analog voltage signals from the plurality of charge amplifiers, and outputs the selected analog voltage signal; an AD converter that is included in the signal processing circuit, is connected to a stage behind the multiplexer, and perform an AD conversion process of converting the analog voltage signal output from the multiplexer into a digital signal corresponding to a voltage value; and a control unit that controls the signal processing circuit such that an irradiation start detection operation and an image reading operation are performed. The irradiation start detection operation reads the charge from the pixel through the signal line from before start of the emission of the radiation and detects the start of the emission of the radiation on the basis of the digital signal corresponding to the read charge. The image reading operation reads the charge from the pixel through the signal line after a pixel charge accumulation period for which the charge is accumulated in the pixel elapses from the start of the emission of the radiation and outputs a radiographic image which is indicated by the digital signal corresponding to the read charge and is provided for diagnosis. The control unit reduces power supplied to all of the charge amplifiers in the irradiation start detection operation to be lower than that in the image reading operation.

[Supplementary Note 2]

There is provided a method for operating a radiographic image detection device comprising a sensor panel in which pixels that are sensitive to radiation which has been emitted from a radiation generation apparatus and transmitted through a subject and accumulate charge are two-dimensionally arranged and a plurality of signal lines for reading the charge are arranged, a signal processing circuit that reads an analog voltage signal corresponding to the charge from the pixel through the signal line to perform signal processing, a plurality of charge amplifiers which are included in the signal processing circuit and each of which is provided for each signal line, is connected to one end of the signal line, and converts the charge from the pixel into the analog voltage signal, a multiplexer that is included in the signal processing circuit, has a plurality of input terminals to which the plurality of charge amplifiers are connected, sequentially selects the analog voltage signals from the plurality of charge amplifiers, and outputs the selected analog voltage signal, an AD converter that is included in the signal processing circuit, is connected to a stage behind the multiplexer, and perform an AD conversion process of converting the analog voltage signal output from the multiplexer into a digital signal corresponding to a voltage value, and a control unit that controls the signal processing circuit. The method comprises: an irradiation start detection step of performing an irradiation start detection operation that reads the charge from the pixel through the signal line from before start of the emission of the radiation and detects the start of the emission of the radiation on the basis of the digital signal corresponding to the read charge; and an image reading step of performing an image reading operation that reads the charge from the pixel through the signal line after a pixel charge accumulation period for which the charge is accumulated in the pixel elapses from the start of the emission of the radiation and outputs a radiographic image which is indicated by the digital signal corresponding to the read charge and is provided for diagnosis. Power supplied to all of the charge amplifiers in the irradiation start detection step is lower than that in the image reading operation.

The irradiation start detection step and the image reading step described in Supplementary Note 2 correspond to Step ST1205 and Step ST1805 illustrated in FIG. 60, respectively.

6. Sixth Invention

In a sixth invention illustrated in FIGS. 61 and 62 which will be described below, the control unit 54 reduces the number of pulses per unit time in the clock signal of the ADC 77 in the AED operation to be less than that in the image reading operation. In the third invention, the number of pulses per unit time in the clock signal of the ADC 77 in the AED operation is reduced to be less than that in the image reading operation by selectively outputting the analog voltage signals V(C) from some CAs including the detection CA 132 to the ADC 77 and causing the ADC 77 to perform only the AD conversion process for the selectively output analog voltage signals V(C). In contrast, the sixth invention differs from the third invention in that the number of pulses per unit time in the clock signal of the ADC 77 in the AED operation is reduced to be less than that in the image reading operation by causing the ADC 77 to perform the AD conversion process for the analog voltage signals V(C) from all of the CAs 60, without distinguishing between the detection CA 132 and the non-detection CA 131, as in the image reading operation.

In the sixth invention, similarly to the second to fifth inventions, for example, the X-ray imaging system 10 and the electronic cassette 16 have the same basic configuration as those in the first invention. Hereinafter, the same components as those in the first to fifth inventions are denoted by the same reference numerals and the description thereof will not be repeated. The difference from the first to fourth inventions will be mainly described.

Figure 61:
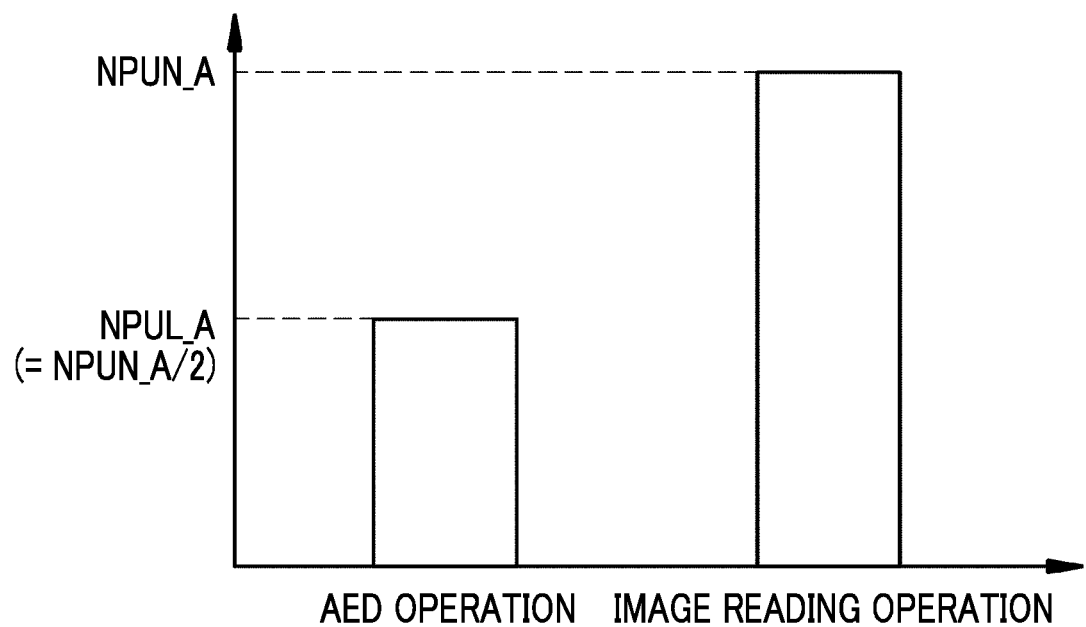
FIG. 61 is a graph illustrating the number of pulses per unit time in the clock signal of the ADC.

As illustrated in FIG. 61, the control unit 54 sets the number of pulses NPU_A per unit time in the clock signals of all of the ADCs 77 to NPUN_A which is the normal number of pulses in the image reading operation and sets the number of pulses NPU_A to NPUL_A that is ½ of NPUN_A in the AED operation.

Figure 62:
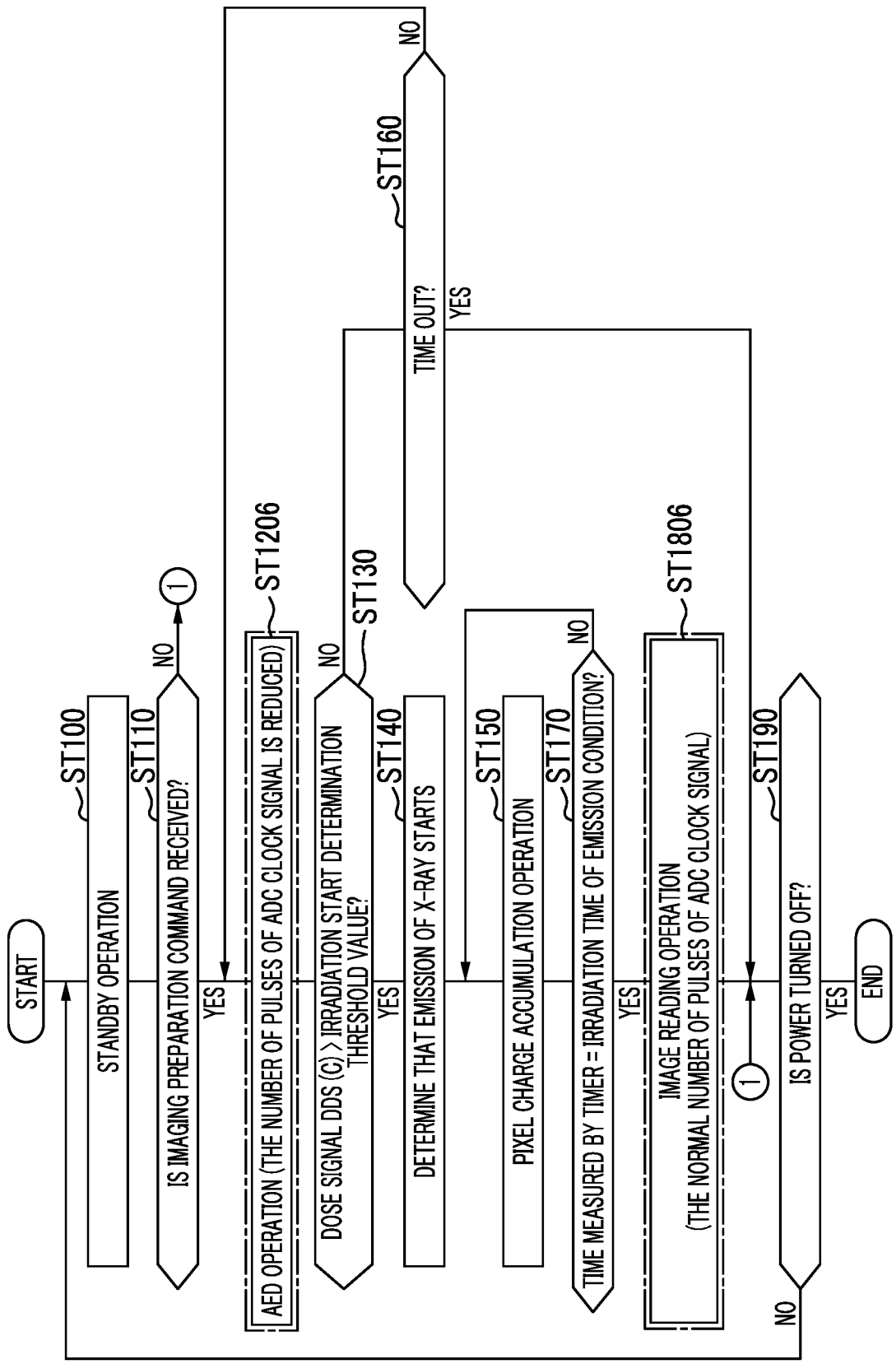
FIG. 62 is a flowchart illustrating the procedure of the operation of an electronic cassette according to a sixth invention.

FIG. 62 is a flowchart illustrating the procedure of the operation of the electronic cassette according to the sixth invention. The flowchart differs from the flowchart illustrated in FIG. 17 of the (1-1)-th embodiment in Steps ST1206 and ST1806 surrounded by a one-dot chain line. Hereinafter, only the difference will be described.

In Step ST1206, in the AED operation, the clock signal in which the number of pulses NPUL_A is ½ of the normal number of pulses NPUN_A is applied to all of the ADCs 77. In contrast, in the image reading operation of Step ST1806, the normal clock signal with the number of pulses NPUN_A is applied to all of the ADCs 77.

As such, since the number of pulses per unit time in the clock signal of the ADC 77 in the AED operation is less than that in the image reading operation, it is possible to reduce the power consumption of the signal processing circuit 51 in the AED operation. Therefore, as in the first to third inventions and the fifth invention, the battery 65 lasts longer than that in the related art. As a result, the number of times the battery 65 is charged is reduced and thus it is possible to improve imaging efficiency.

It is possible to understand a radiographic image detection device described in the following Supplementary Note 3 and a method for operating a radiographic image detection device described in the following Supplementary Note 4 from the above description.

[Supplementary Note 3]

There is provided a radiographic image detection device comprising: a sensor panel in which pixels that are sensitive to radiation which has been emitted from a radiation generation apparatus and transmitted through a subject and accumulate charge are two-dimensionally arranged and a plurality of signal lines for reading the charge are arranged; a signal processing circuit that reads an analog voltage signal corresponding to the charge from the pixel through the signal line to perform signal processing; a plurality of AD converters that are included in the signal processing circuit, perform an AD conversion process of converting the analog voltage signal into a digital signal corresponding to a voltage value, and share the AD conversion process performed for each of the signal lines; and a control unit that controls the signal processing circuit such that an irradiation start detection operation and an image reading operation are performed. The irradiation start detection operation reads the charge from the pixel through the signal line from before start of the emission of the radiation and detects the start of the emission of the radiation on the basis of the digital signal corresponding to the read charge. The image reading operation reads the charge from the pixel through the signal line after a pixel charge accumulation period for which the charge is accumulated in the pixel elapses from the start of the emission of the radiation and outputs a radiographic image which is indicated by the digital signal corresponding to the read charge and is provided for diagnosis. In the irradiation start detection operation, for all of the AD converters, the control unit reduces the number of pulses per unit time in a clock signal which defines the operation timing of the AD converter to be less than that in the image reading operation.

[Supplementary Note 4]

There is provided a method for operating a radiographic image detection device comprising a sensor panel in which pixels that are sensitive to radiation which has been emitted from a radiation generation apparatus and transmitted through a subject and accumulate charge are two-dimensionally arranged and a plurality of signal lines for reading the charge are arranged, a signal processing circuit that reads an analog voltage signal corresponding to the charge from the pixel through the signal line to perform signal processing, a plurality of AD converters that are included in the signal processing circuit, perform an AD conversion process of converting the analog voltage signal into a digital signal corresponding to a voltage value, and share the AD conversion process performed for each of the signal lines, and a control unit that controls the signal processing circuit. The method comprises: an irradiation start detection step of performing an irradiation start detection operation that reads the charge from the pixel through the signal line before the start of the emission of the radiation and detects the start of the emission of the radiation on the basis of the digital signal corresponding to the read charge; and an image reading step of performing an image reading operation that reads the charge from the pixel through the signal line after a pixel charge accumulation period for which the charge is accumulated in the pixel elapses from the start of the emission of the radiation and outputs a radiographic image which is indicated by the digital signal corresponding to the read charge and is provided for diagnosis. In the irradiation start detection step, for all of the AD converters, the number of pulses per unit time in a clock signal which defines the operation timing of the AD converter is less than that in the image reading operation.

The irradiation start detection step and the image reading step described in Supplementary Note 4 correspond to Step ST1206 and Step ST1806 illustrated in FIG. 62, respectively.

7. Seventh Invention

A seventh invention illustrated in FIGS. 63 and 64 which will be described below is a modification example of the circuit configuration. In the seventh invention, similarly to the second to sixth inventions, for example, the X-ray imaging system 10 and the electronic cassette 16 have the same basic configuration as those in the first invention. Hereinafter, the same components as those in the first to sixth inventions are denoted by the same reference numerals and the description thereof will not be repeated. The difference from the first to fourth inventions will be mainly described.

Figure 63:
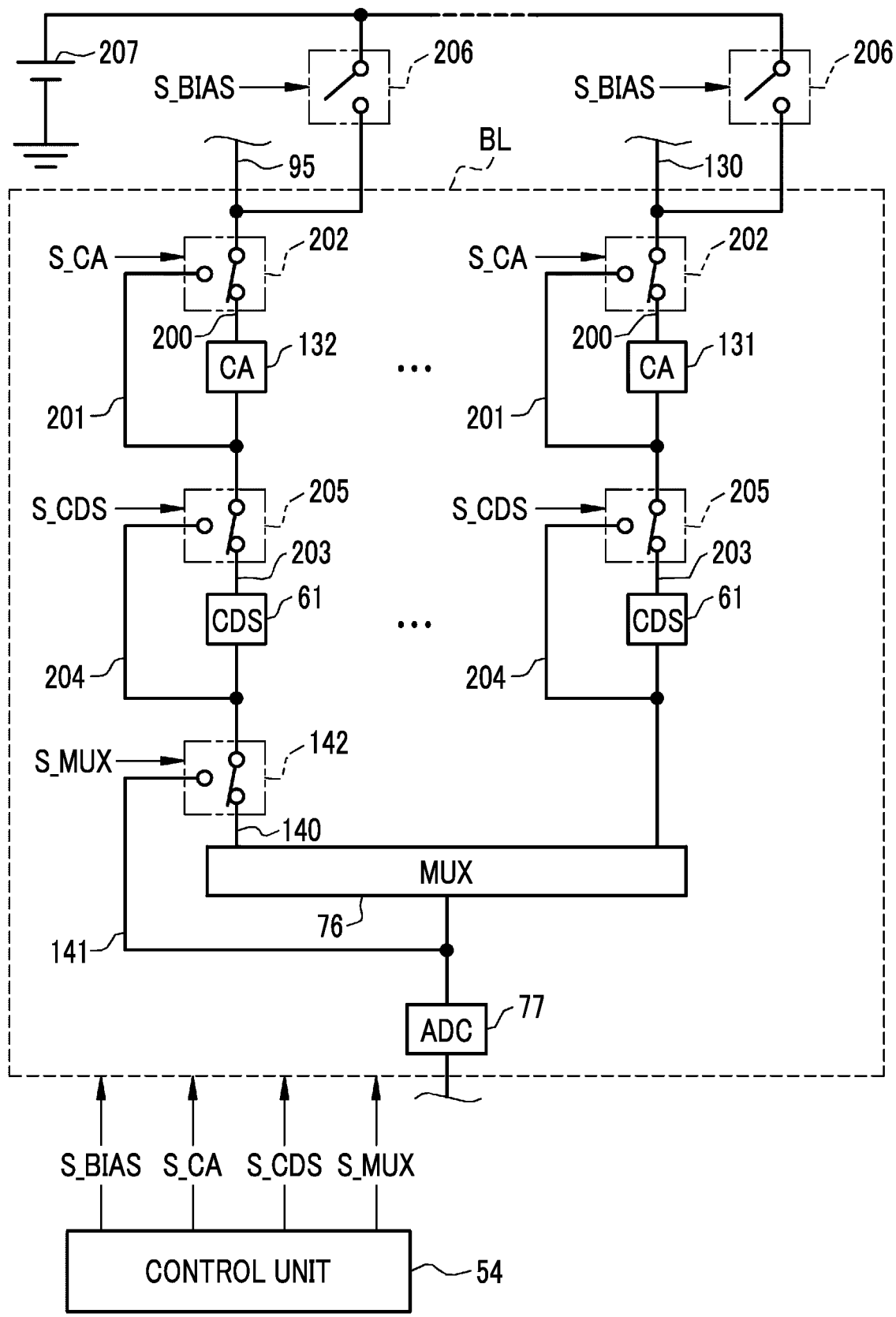
FIG. 63 is a diagram illustrating the circuit configuration of a block and the periphery thereof and a state in the image reading operation in a seventh invention.
Figure 64:
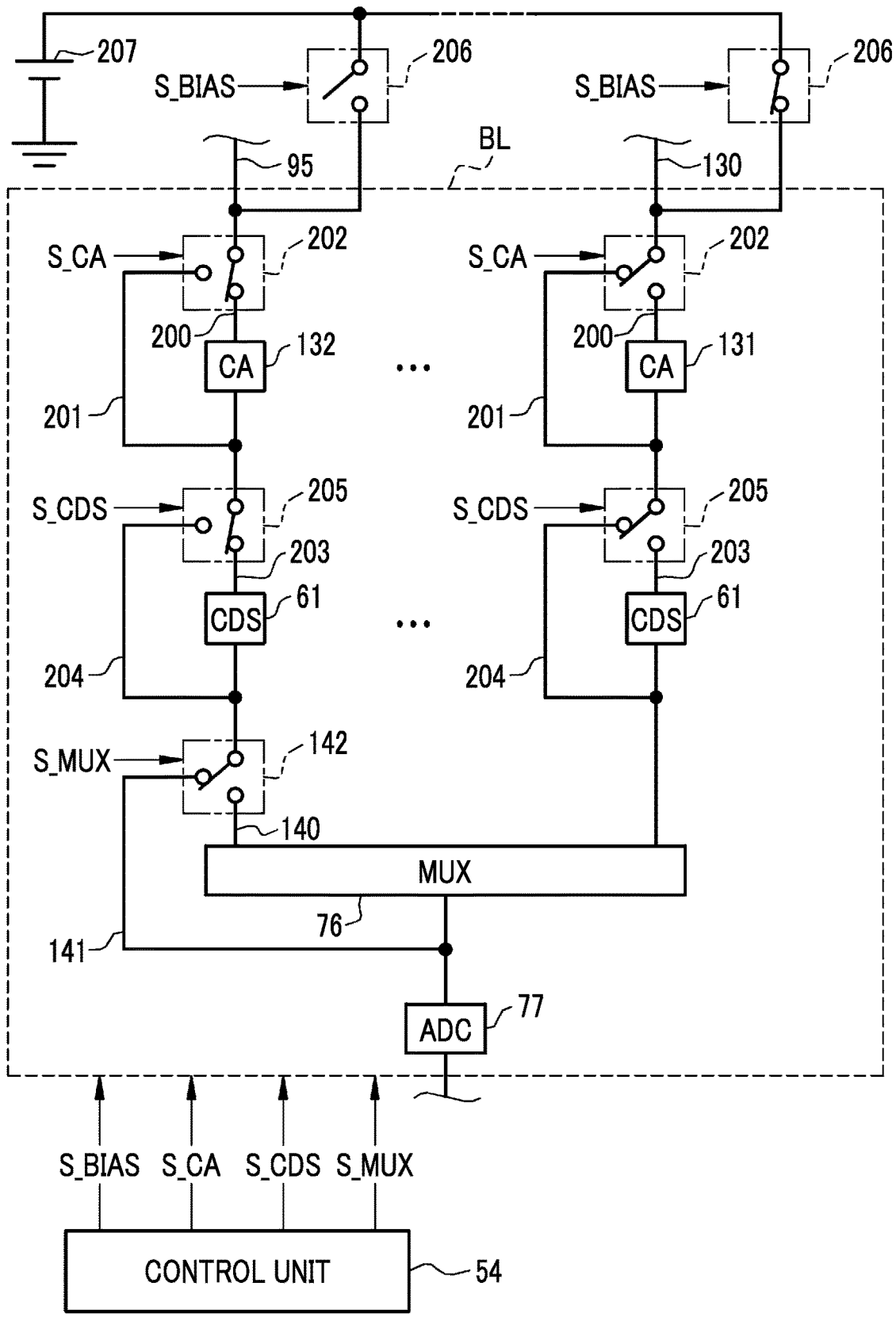
FIG. 64 is a diagram illustrating the circuit configuration of the block and the periphery thereof and a state in the AED operation in the seventh invention.

FIGS. 63 and 64 illustrate the circuit configuration of one block BL and the periphery thereof in the seventh invention. In the block BL, the detection channel 95 and the non-detection channel 130 are mixed as in the (2-1)-th embodiment illustrated in FIG. 39. As in the (3-2)-th embodiment illustrated in FIG. 49, the detection channel 95 is divided into the first path 140 and the second path 141 in the stage behind the CDS 61 and the switch 142 is connected to the detection channel 95. The switch 142 switches the path connected to the detection channel 95 to the first path 140 or the second path 141 in response to a driving control signal S_MUX input from the control unit 54.

Each of the detection channel 95 and the non-detection channel 130 is divided into a first path 200 and a second path 201 in a stage before the detection CA 132 and the non-detection CA 131. The first paths 200 are connected to the detection CA 132 and the non-detection CA 131. The second paths 201 are connected to the CDSs 61 without passing through the detection CA 132 and the non-detection CA 131, respectively. The first paths 200 are for inputting charge to the detection CA 132 and the non-detection CA 131. The second paths 201 are for outputting charge to the MUX 76 without passing through the detection CA 132 and the non-detection CA 131.

A switch 202 is connected to the detection channel 95 or the non-detection channel 130, the first path 200, and the second path 201. The switch 202 switches the path connected to the detection channel 95 or the non-detection channel 130 to the first path 200 or the second path 201 in response to a driving control signal S_CA input from the control unit 54.

Similarly, each of the detection channel 95 and the non-detection channel 130 is divided into a first path 203 and a second path 204 in the stage before the CDS 61 and a switch 205 is connected to each of the detection channel 95 and the non-detection channel 130. The switch 205 switches the path connected to the detection channel 95 or the non-detection channel 130 to the first path 203 or the second path 204 in response to a driving control signal S_CDS input from the control unit 54.

A bias power supply 207 is connected to the detection channel 95 and the non-detection channel 130 through switches 206. The switch 206 is turned on and off in response to a driving control signal S_BIAS input from the control unit 54.

The control unit 54 outputs the driving control signals S_MUX, S_CA, and S_CDS to the switches 142, 202, and 205 of the channels 95 and 130 (each signal line 42), respectively. Therefore, the control unit 54 can individually control the driving of each of the switches 142, 202, 205. For example, the control unit 54 controls the switches 202 and 205 of the detection channel 95 such that they are connected to the first paths 200 and 203 and controls the switches 202 and 205 of the non-detection channel 130 such that they are connected to the second paths 201 and 204. Similarly, for example, the control unit 54 can individually output the driving control signal S_BIAS to the switches 206 such that the detection channel 95 is turned off and the non-detection channel 130 is turned on.

FIG. 63 illustrates a case in which the image reading operation is performed. That is, the first paths 140, 200, and 203 in each of the channels 95 and 130 are selected by the switches 142, 202, and 205, respectively. In addition, each switch 206 is in an off state.

In contrast, in the AED operation, for example, the state illustrated in FIG. 64 is obtained. That is, in the detection channel 95, the second path 141 is selected by the switch 142 and the first paths 200 and 203 are selected by the switches 202 and 205, respectively. The switch 206 is still in the off state. This state is the same as that illustrated in FIG. 49A of the (3-2)-th embodiment. Therefore, as described in the (3-2)-th embodiment, the analog voltage signal V(C) from the detection CA 132 is directly output to the ADC 77 without passing through the MUX 76.

In contrast, in the non-detection channel 130, the second paths 201 and 204 are selected by the switches 202 and 205, respectively. In addition, the switch 206 is in an on state. In this case, the charge of the non-detection channel 130 is directly output to the MUX 76 without passing through the non-detection CA 131 and the CDS 61. A bias voltage is applied from the bias power supply 207 to the non-detection channel 130 through the switch 206.

In this case, the non-detection CA 131 is in a power-off state in which the supply power PL_C is 0, as in the (2-2)-th embodiment illustrated in FIG. 41. The CDS 61 of the non-detection channel 130 is also in the power-off state.

In a case in which the non-detection CA 131 is in the power-off state, as described in the (2-2)-th embodiment, the virtual short state between two input terminals of the non-detection CA 131 is not maintained and the potential of the input stage of the non-detection CA 131 becomes indefinite. Then, the charge of the non-detection channel 130 also becomes unstable, which has a bad influence on the image reading operation later. Therefore, in the seventh invention, the switch 206 is turned on to apply the bias voltage from the bias power supply 207 to the non-detection channel 130. Then, it is possible to solve the problem that the charge of the non-detection channel 130 becomes unstable, which has a bad influence on the image reading operation later.

In addition, the non-detection CA 131 may not be in the power-off state, but the supply power PL_C that does not cause the potential of the input stage to be indefinite may be supplied to change the non-detection CA 131 to the low power state as in the (2-1)-th embodiment.

As in the (2-3)-th embodiment illustrated in FIG. 43, in addition to the non-detection CA 131, the detection CA 132 may be driven in the low power state in which power lower than the normal power PN_C and is greater than 0 is supplied. However, in this case, as illustrated in FIG. 64, in the AED operation, in the detection channel 95, the second path 141 is selected by the switch 142, the first paths 200 and 203 are selected by the switches 202 and 205, respectively, and the switch 206 is turned off.

In a case in which the detection CA 132 is driven in the low power state, the detection performance of the detection CA 132 is degraded. As a result, there is a concern that the S/N ratio of the dose signal DDS(C) will be reduced. For this reason, it is preferable that the number of gate lines 41 to which the gate pulses G(R) are applied at the same time by the gate driving unit 50 is increased to increase the amount of charge added in the detection channel 95, thereby improving the S/N ratio of the dose signal DDS(C).

The control unit 54 may not output the driving control signals S_MUX, S_CA, S_CDS, and S_BIAS to the switches 142, 202, 205, and 206 of the channels 95 and 130 (each signal line 42), respectively, but may uniformly output the driving control signals S_MUX, S_CA, S_CDS, S_BIAS in units of the blocks BL. For example, as in the (1-5)-th embodiment, in the blocks BL in which the ADC 77 is always in the non-operating state, the switches 142, 202, and 205 are uniformly connected to the second paths 141, 201, and 204, respectively, and the switch 206 is uniformly turned on.

The switch 206 and the bias power supply 207 may be provided in the block BL or the signal processing circuit 51.

The detection CA 132 is switched to the power-off state and the switch 206 is turned on to apply the bias voltage from the bias power supply 207 to the detection channel 95 such that the switches 202 and 205 of the detection channel 95 are connected to the second paths 201 and 204, respectively. Then, the ADC 77 converts a variation in the load of the bias power supply 207 caused by a current flowing to the pixel 40 in a case in which X-rays are emitted into the digital signal DS(C). The digital signal DS(C) is used as the dose signal DDS(C). In a case in which a variation in the dose signal DS(C) is out of a predetermined range, it may be determined that the emission of X-rays has started.

Similarly, the non-detection CA 131 is switched to the power-off state and the switch 206 is turned on to apply the bias voltage from the bias power supply 207 to the non-detection channel 130 such that the switches 202 and 205 of the non-detection channel 130 are connected to the second paths 201 and 204, respectively. Then, the ADC 77 converts a variation in the load of the bias power supply 207 caused by a current flowing to the pixel 40 in a case in which X-rays are emitted into the digital signal DS(C). The digital signal DS(C) is used as the dose signal DDS(C). In a case in which a variation in the dose signal DS(C) is out of a predetermined range, it may be determined that the emission of X-rays has started.

Alternatively, it may be determined whether the emission of X-rays has started on the basis of both the dose signal DDS(C) which has been output from the detection channel 95 and indicates a variation in the load of the bias power supply 207 and the dose signal DDS(C) which has been output from the non-detection channel 130 and indicates a variation in the load of the bias power supply 207. Specifically, the difference or ratio between the dose signals DDS (C) may be calculated and it may be determined whether the emission of X-rays has started on the basis of the calculated difference or ratio. In this case, since an impact or a noise component, such as vibration noise and electromagnetic noise, applied to the electronic cassette 16 is canceled, it is possible to reduce a concern that the start of the emission of X-rays will be erroneously determined due to the noise component.

The detection CA 132 or the non-detection CA 131 may not be changed to the power-off state, but the power PL_C that does not cause the potential of the input stage of the detection CA 132 or the non-detection CA 131 to be indefinite may be supplied to change the detection CA 132 or the non-detection CA 131 to the low power state as in the (2-1)-th embodiment.

The power supply for acquiring the dose signal DDS(C) indicating a load variation is not limited to the bias power supply 207. Any power supply, such as a power supply for the ADC 77, the CA 60, or the CDS 61, may be used as long as it is turned on during the AED operation.

However, in a case in which whether the emission of X-rays has started is determined on the basis of the dose signal DDS(C) indicating a variation in the load of the power supply, the variation in the load of the power supply is small. Therefore, the S/N ratio of the dose signal DDS(C) is reduced and there is a concern that the X-ray emission start detection performance will be degraded.

For this reason, it is preferable that the number of gate lines 41 to which the gate pulses G(R) are applied at the same time by the gate driving unit 50 is increased to increase the amount of charge added in the detection channel 95 or the non-detection channel 130, thereby improving the S/N ratio of the dose signal DDS(C). Alternatively, the dose signals DDS(C) between adjacent channels may be added or added and averaged to improve the S/N ratio of the dose signal DDS(C). In addition, the method which increases the number of gate lines 41 to which the gate pulses G(R) are applied at the same time by the gate driving unit 50 to increase the amount of charge added in each channel and the method which adds or adds and averages the dose signals DDS(C) between adjacent channels may be combined to improve the S/N ratio of the dose signal DDS(C).

The seventh invention may be combined with each embodiment of the first invention, the second invention, the third invention, and the fourth invention. For example, as in the second to fourth inventions, the first invention may be applied such that the control unit 54 periodically switches the power supply state of the ADC 77 and the MUX 76 which form the block BL between the first state and the second state, as illustrated in FIG. 14 in the (1-1)-th embodiment.

As in the second and fourth inventions, the switching patterns of power supply to the ADC 77 and the block BL in the seventh invention and the first invention may be combined as follows. First, in a case in which there are two or more blocks BL including the MUX 76 and the ADC 77 whose power supply state is periodically switched as illustrated in, for example, FIG. 14 of the (1-1)-th embodiment, the control unit 54 may shift the switching timing of the power supply state of at least two of the two or more blocks BL.

In addition, the control unit 54 may shift the switching timing of the power supply state for each of a plurality of groups to which two or more blocks BL belong, as illustrated in, for example, FIG. 14 of the (1-1)-th embodiment. In this case, it is preferable that at least one block BL is disposed between two blocks BL belonging to the same group. Alternatively, as illustrated in, for example, FIG. 18 of the (1-2)-th embodiment, the switching timing of the power supply state of all of the two or more blocks BL may be shifted.

As illustrated in, for example, FIG. 21 of the (1-5)-th embodiment, in a case in which there are a plurality of blocks BL including the MUX 76 to which only the non-detection CA 131 is connected, at least one of the plurality of blocks BL may be always in the second state.

As in the (1-12)-th embodiment illustrated in FIGS. 35 to 37, leak charge correction and temperature drift correction may be performed for the dose signal DDS(C).

In addition, the (1-8)-th embodiment illustrated in FIGS. 25 to 27 in which the detection channel 95 that is the signal line 42 to which the detection pixel 90 used for the AED operation is connected is set, the (1-9)-th embodiment illustrated in FIGS. 28 to 31 in which the detection pixel 90X used only for the AED operation is provided, the (1-10)-th embodiment illustrated in FIG. 32 in which the setting of the detection pixel 90 can be changed, the (1-11)-th embodiment illustrated in FIGS. 33 and 34 in which the operation of the CDS 61 in the AED operation is simplified, and the (1-13)-th embodiment illustrated in FIG. 38 in which the digital signal transmission I/F is switched may be combined with each other.

Further, the (2-1)-th to (2-3)-th embodiments of the second invention illustrated in FIGS. 39 to 43 may be applied to change at least one of the non-selected CAs other than some CAs that selectively output the analog voltage signal V(C) to the ADC 77 to the power saving state in which power supplied to the non-selected CAs in the AED operation is lower than normal power in the image reading operation.

In addition, the (3-1)-th and (3-2)-th embodiments illustrated in FIGS. 44 to 49 in which the number of pulses per unit time in the clock signal of the ADC 77 is less than that in the image reading operation may be applied.

Further, the (4-1)-th to (4-3)-th embodiments illustrated in FIGS. 50 to 58 may be applied in which each of the plurality of blocks BL1 to BL16 is switched from the second state to the first state a predetermined time, which is required to stably operate, for example, the ADC 77 forming the block BL, before the start timing of charge reading in the AED operation.

In each embodiment of the first to seventh inventions, the electronic cassette 16 is given as an example of the radiographic image detection device. However, the invention is not limited thereto. The invention can also be applied to a stationary radiographic image detection device that is fixed to the upright imaging table 18 or the decubitus imaging table 19.

In each embodiment of the first to seventh inventions, for example, the following various processors can be used as the hardware structure of processing units performing various processes, such as the control unit 54, the leak charge correction unit 121, and the temperature drift correction unit 122.

The various processors include, for example, a CPU, a programmable logic device (PLD), and a dedicated electric circuit. The CPU is a general-purpose processor that executes software (program) to function as various processing units as is well known. The PLD is a processor such as a field programmable gate array (FPGA) whose circuit configuration can be changed after manufacture. The dedicated electric circuit is a processor such as an application specific integrated circuit (ASIC) which has a dedicated circuit configuration designed to perform a specific process.

One processing unit may be configured by one of the various processors or a combination of two or more processors of the same type or different types (for example, a combination of a plurality of FPGAs and a combination of a CPU and an FPGA). In addition, a plurality of processing units may be configured by one processor. A first example of the configuration in which a plurality of processing units are configured by one processor is an aspect in which one processor is configured by a combination of one or more CPUs and software and functions as a plurality of processing units. A second example of the configuration is an aspect in which a processor that implements the functions of the entire system including a plurality of processing units using one IC chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, is used as the hardware structure of the various processors.

The invention is not limited to X-rays and can also be applied to a case in which other types of radiation including γ-rays are used.

The conjunction "or" described in the specification is not an expression intended to be a limited interpretation, such as any one of a plurality of options connected by the conjunction, and is an expression including combinations of the plurality of options, depending on the context. For example, a sentence "an option A or an option B is performed" should be interpreted as having the following three meanings, depending on the context: "the option A is performed"; "the option B is performed"; and "the option A and the option B are performed".

The invention is not limited to each embodiment of the first to seventh inventions and may have various configurations as long as it does not depart from the scope and spirit of the invention. In addition, the invention may include a storage medium storing a program in addition to the program.

EXPLANATION OF REFERENCES

- 10: X-ray imaging system
- 11: X-ray generation apparatus
- 12: X-ray imaging apparatus
- 13: X-ray source
- 14: radiation source control device
- 15: irradiation switch
- 16: electronic cassette (radiographic image detection device)
- 17: console
- 18: upright imaging table
- 19: decubitus imaging table
- 20: display
- 21: input device
- 22, 23: wireless communication unit
- 25: menu and condition table
- 30: sensor panel
- 31: circuit unit
- 32: housing
- 32A: front surface
- 33: transmission plate
- 34: scintillator
- 35: light detection substrate
- 40: pixel
- 41, 107: gate line
- 42: signal line
- 43, 105: photoelectric conversion unit
- 44, 106: TFT
- 50, 108: gate driving unit
- 51: signal processing circuit
- 52: memory
- 53: power supply unit
- 54: control unit
- 60: charge amplifier (CA)
- 61: correlated double sampling circuit (CDS)
- 62: multiplexer (MUX) unit
- 63: AD converter (ADC) unit
- 65: battery
- 66: wired communication unit
- 70: operational amplifier
- 71: capacitor
- 72: amplifier reset switch
- 73A: first sample-and-hold circuit (first S/H)
- 73B: second sample-and-hold circuit (second S/H)
- 74: difference amplifier
- 75: (first to twelfth) gate driving circuit
- 76, 76A, 76B, 135: (first to sixteenth) MUX
- 77: (first to sixteenth) ADC
- 90, 90X, 90X1 to 90X3: detection pixel
- 95: detection channel
- 100: short-circuit line
- 120: reference channel
- 121: leak charge correction unit
- 122: temperature drift correction unit
- 125: LVDS interface (I/F)
- 126: CMOS interface (I/F)
- 127: switch
- 130: non-detection channel
- 131: non-detection CA
- 132: detection CA
- 133: switch
- 140, 200, 203: first path
- 141, 201, 204: second path
- 142, 202, 205, 206: switch
- 207: bias power supply
- G(R): gate pulse
- V(C): analog voltage signal
- DS(C): digital signal
- DIS(C): image signal
- DDS(C): dose signal
- RCDDS(C): leak charge corrected dose signal
- DRCDDS(C): temperature drift corrected dose signal
- AR1 to AR16: area
- BL1 to BL16: block
- CP1 to CP4: chip
- T: unit time
- P_A, PON_A, PSL_A: power supplied to ADC
- ST100 to ST190, ST1202 to ST1206, ST1802 to ST1806, ST300 to ST330: step
- LA1, LA2: area
- RLA1 to RLA3: range
- α(C): correction coefficient
- F{DRS(C−1), DRS(C+1)}: correction coefficient calculation formula
- TP: temperature of central portion of block
- SC: charge generated in detection pixel
- LC: leak charge
- P_C, PN_C, PL_C, PL_C1, PL_C2: power supplied to CA
- DT: alphabets indicating detection channel
- NDT: alphabets indicating non-detection channel
- NPU_A, NPUN_A, NPUL_A: pulse number per unit time in clock signal of ADC
- CLN_A, CLL_A: clock signal of ADC
- TC: period of clock signal
- TW: time required to stably operate block
- TX: reading period of dose signal
- S_MUX, S_CA, S_CDS, S_BIAS: switch driving control signal

What is claimed is:

1. A radiographic image detection device comprising:
a sensor panel in which pixels that are sensitive to radiation which has been emitted from a radiation generation apparatus and transmitted through a subject and accumulate charge are two-dimensionally arranged and a plurality of signal lines for reading the charge are arranged;

a signal processing circuit that reads an analog voltage signal corresponding to the charge from the pixel through the signal line to perform signal processing;

a plurality of charge amplifiers that are included in the signal processing circuit and each of which is provided for each signal line, is connected to one end of the signal line, and converts the charge from the pixel into the analog voltage signal;

a multiplexer that is included in the signal processing circuit, has a plurality of input terminals to which the plurality of charge amplifiers are respectively connected, sequentially selects the analog voltage signals from the plurality of charge amplifiers, and outputs the selected analog voltage signal;

an AD converter that is included in the signal processing circuit, is connected to a stage behind the multiplexer, and performs an AD conversion process of converting the analog voltage signal output from the multiplexer into a digital signal corresponding to a voltage value; and a processor configured to control the signal processing circuit such that an irradiation start detection operation and an image reading operation are performed, wherein the irradiation start detection operation reads the charge through a detection channel which is the signal line connected to a preset detection pixel among the pixels from before start of the emission of the radiation and detects the start of the emission of the radiation on the basis of the digital signal corresponding to the read charge, the image reading operation reads the charge from the pixel through the signal line after a pixel charge accumulation period for which the charge is accumulated in the pixel elapses after the start of the emission of the radiation and outputs a radiographic image which is indicated by the digital signal corresponding to the read charge and is provided for diagnosis, and in a case where power supplied to the charge amplifier during the image reading operation is normal power, in the irradiation start detection operation, the processor causes at least one of non-detection charge amplifiers other than a detection charge amplifier that is the charge amplifier connected to the detection channel, among the plurality of charge amplifiers connected to the multiplexer to be in a power saving state in which the supply power is lower than the normal power, and drives at least one of a plurality of the detection charge amplifiers in a low power state in which power lower than the normal power and greater than 0 is supplied.

2. The radiographic image detection device according to claim 1, wherein the power saving state is the low power state.

3. The radiographic image detection device according to claim 1, wherein the power saving state is a power-off state in which the supply of power is stopped.

4. The radiographic image detection device according to claim 1, wherein the processor causes all of the non-detection charge amplifiers to be in the power saving state during the irradiation start detection operation.

5. The radiographic image detection device according to claim 1, further comprising:

a first path through which the charge is input to the detection charge amplifier;

a second path through which the charge is output to the multiplexer without passing through the charge amplifier; and a switch that selectively switches between the first path and the second path, wherein the processor controls the switch to select the second path for the non-detection charge amplifier in the power saving state.

6. The radiographic image detection device according to claim 5, wherein in a case where the power saving state is a power-off state in which the supply of power is stopped, the control unit applies a bias voltage for stabilizing a potential of an input stage to the non-detection charge amplifier in the power-off state.

7. The radiographic image detection device according to claim 1, further comprising:

a plurality of blocks each of which includes the multiplexer to which at least one of the detection charge amplifiers is connected and the AD converter connected to a stage behind the multiplexer, wherein the processor has a function of switching a power supply state of the block between a first state in which first power is supplied and a second state in which second power lower than the first power per unit time is supplied, and periodically switches the power supply state of at least one of the plurality of blocks during the irradiation start detection operation.

8. The radiographic image detection device according to claim 7, wherein in a case where the number of blocks whose power supply state is periodically switched is two or more, the processor shifts a switching timing of the power supply state of at least two of the two or more blocks.

9. The radiographic image detection device according to claim 8, wherein the two or more blocks are divided into groups, and the processor shifts the switching timing of the power supply state for each group.

10. The radiographic image detection device according to claim 9, wherein at least one block is disposed between two blocks belonging to the same group.

11. The radiographic image detection device according to claim 8, wherein the processor shifts the switching timing of the power supply state of all of the two or more blocks.

12. The radiographic image detection device according to claim 7, wherein the processor causes at least one of the blocks including the multiplexer to which only the non-detection charge amplifier is connected to be in the second state at all the times among the plurality of blocks during the irradiation start detection operation.

13. The radiographic image detection device according to claim 7, wherein the block is provided for each area that is formed by the pixels connected to a plurality of the adjacent signal lines.

14. The radiographic image detection device according to claim 13,
wherein a plurality of chips are provided, and a plurality of the adjacent blocks that are in charge of the areas adjacent to each other are mounted on each of the plurality of chips.

15. The radiographic image detection device according to claim 14,
wherein the processor switches the power supply state of the block in units of the blocks that are in charge of the areas or in units of the plurality of chips.

16. The radiographic image detection device according to claim 7,
wherein the processor corrects a temperature drift of the digital signal which is generated by a bias in a temperature distribution in the signal processing circuit due to the switching of the power supply state of the block.

17. The radiographic image detection device according to claim 1,
wherein the detection pixel is a dedicated pixel which is specialized for the irradiation start detection operation.

18. The radiographic image detection device according to claim 1,
wherein the radiographic image detection device is an electronic cassette that is configured by accommodating the sensor panel and the signal processing circuit in a portable housing and is supplied with power from a battery provided in the housing.

19. A method for operating a radiographic image detection device comprising a sensor panel in which pixels that are sensitive to radiation which has been emitted from a radiation generation apparatus and transmitted through a subject and accumulate charge are two-dimensionally arranged and a plurality of signal lines for reading the charge are arranged, a signal processing circuit that reads an analog voltage signal corresponding to the charge from the pixel through the signal line to perform signal processing, a plurality of charge amplifiers that are included in the signal processing circuit and each of which is provided for each signal line, is connected to one end of the signal line, and converts the charge from the pixel into the analog voltage signal, a multiplexer that is included in the signal processing circuit, has a plurality of input terminals to which the plurality of charge amplifiers are respectively connected, sequentially selects the analog voltage signals from the plurality of charge amplifiers, and outputs the selected analog voltage signal, an AD converter that is included in the signal processing circuit, is connected to a stage behind the multiplexer, and performs an AD conversion process of converting the analog voltage signal output from the multiplexer into a digital signal corresponding to a voltage value, and a processor configured to control the signal processing circuit such that an irradiation start detection operation and an image reading operation are performed, the method comprising:

an irradiation start detection step of performing an irradiation start detection operation that reads the charge through a detection channel which is the signal line connected to a preset detection pixel among the pixels from before start of the emission of the radiation and detects the start of the emission of the radiation on the basis of the digital signal corresponding to the read charge; and an image reading step of performing an image reading operation that reads the charge from the pixel through the signal line after a pixel charge accumulation period for which the charge is accumulated in the pixel elapses from the start of the emission of the radiation and outputs a radiographic image which is indicated by the digital signal corresponding to the read charge and is provided for diagnosis, wherein in a case where power supplied to the charge amplifier during the image reading step is normal power, in the irradiation start detection step, at least one of non-detection charge amplifiers other than a detection charge amplifier that is the charge amplifier connected to the detection channel, among the plurality of charge amplifiers connected to the multiplexer is caused to be in a power saving state in which the supply power is lower than the normal power, and at least one of a plurality of the detection charge amplifiers is driven in a low power state in which power lower than the normal power and greater than 0 is supplied.

* * * * *